United States Patent
Bang et al.

(10) Patent No.: US 10,358,642 B2
(45) Date of Patent: *Jul. 23, 2019

(54) METHOD OF PREPARING NUCLEIC ACID MOLECULES

(71) Applicant: CELEMICS, INC., Seoul (KR)

(72) Inventors: Duhee Bang, Seoul (KR); Hwangbeom Kim, Seoul (KR); Hyojun Han, Seoul (KR)

(73) Assignee: CELEMICS, INC., Seoul (KR)

( * ) Notice: Subject to any disclaimer, the term of this patent is extended or adjusted under 35 U.S.C. 154(b) by 82 days.

This patent is subject to a terminal disclaimer.

(21) Appl. No.: 15/132,245

(22) Filed: Apr. 19, 2016

(65) Prior Publication Data

US 2016/0222380 A1 Aug. 4, 2016

Related U.S. Application Data

(63) Continuation of application No. 14/235,799, filed as application No. PCT/KR2012/006147 on Aug. 1, 2012, now Pat. No. 9,340,826.

(30) Foreign Application Priority Data

Aug. 1, 2011 (KR) .................. 10-2011-0076408

(51) Int. Cl.
  *C12Q 1/68* (2018.01)
  *C12N 15/10* (2006.01)
  *C12Q 1/6806* (2018.01)

(52) U.S. Cl.
  CPC ..... *C12N 15/1093* (2013.01); *C12N 15/1027* (2013.01); *C12N 15/1031* (2013.01); *C12N 15/1065* (2013.01); *C12Q 1/6806* (2013.01)

(58) Field of Classification Search
  None
  See application file for complete search history.

(56) References Cited

U.S. PATENT DOCUMENTS

| | | | |
|---|---|---|---|
| 2007/0269870 A1* | 11/2007 | Church | C12N 15/10 435/91.2 |
| 2010/0016178 A1 | 1/2010 | Sussman et al. | |
| 2010/0069263 A1 | 3/2010 | Shendure et al. | |
| 2014/0045728 A1* | 2/2014 | Church | C40B 50/14 506/26 |

OTHER PUBLICATIONS

Kosuri et al. (Scalable gene synthesis by selective amplification of DNA pools from high-fidelity microchips, Nature Biotechnology vol. 28, pp. 1295-1299 (2010), Nov. 28, 2010).*

(Continued)

*Primary Examiner* — Aaron A Priest
(74) *Attorney, Agent, or Firm* — STIP Law Group, LLC

(57) ABSTRACT

Disclosed is a method of preparing nucleic acid molecules, including: providing a pool of oligonucleotides, each containing restriction enzyme digestion sequences and generic flanking sequences; cleaving the restriction enzyme digestion sequence portions to provide a pool of mixtures comprising the oligonucleotides, each containing the generic flanking sequences at one end, and the oligonucleotides, each containing none of the generic flanking sequences at one end, and; assembling the oligonucleotides using the generic flanking sequences to randomly synthesize nucleic acid fragments.

6 Claims, 9 Drawing Sheets

Specification includes a Sequence Listing.

(56) References Cited

OTHER PUBLICATIONS

Kim et al. (Hierarchical gene synthesis using DNA microchip oligonucleotides, J Biotechnol. Feb. 20, 2011;151(4):319-24. Epub Jan. 13, 2011).*

Yehezkel et al. (De novo DNA synthesis using single molecule PCR, Nucleic Acids Res. Oct. 2008; 36(17): e107. Published online Jul. 30, 2008.*

Matzas et al. (High-fidelity gene synthesis by retrieval of sequence-verified DNA identified using high-throughput pyrosequencing, Nature Biotechnology 28, 1291-1294 (2010), Published online Nov. 28, 2010.*

Kim, H. et al. "'shotgun DNA synthesis' for the high-throughput construction of large DNA molecules", Nucleic Acids Res., Oct. 2012, Vol. 40, No. 18, e140 (Epub. Jun. 16, 2012).

Maeda, N. et al., "Development of a DNA barcode tagging method for monitoring dynamic changes in gene expression by using an ultra high-throughput sequencer", Biotechniques, Jul. 2008, Vol. 45, No. 1, pp. 95-97.

Carr, I. M. et al., "Illuminator, a desktop program for mutation detection using short-read clonal sequencing", Genomics, Oct. 2011, Vol. 98, No. 4, pp. 302-309 (Epub. May 19, 2011).

Sakiyama, T. et al., "An automated system for genome analysis to support microbial whole-genome shotgun sequencing", Biosci. Biotechnol. Biochem., Mar. 2000, Vol. 64; No. 3, pp. 670-673.

Jingdong Tian et al., "Accurate multiplex gene synthesis from programmable DNA microchips", Nature, vol. 432, Dec. 23/30, 2004, pp. 1050-1054.

Hutchison et al., "Cell-free cloning usingΦ29 DNA polymerase", PNAS, Nov. 29, 2005, vol. 102, No. 48, pp. 17332-17336.

Kun Zhang et al., "Sequencing genomes from single cells by polymerase cloning", Nature Biotechnology, vol. 24, No. 6, Jun. 2006, pp. 680-686.

Pere Puigbo et al., "Optimizer: a web server for optimizing the codon usage of DNA sequences", Nucleic Acids Research, 2007, vol. 35, Web Server issue.

Tuval Ben Yehezkel et al., "De novo DNA synthesis using single molecule PCR, Nucleic Acids Research", 2008, vol. 36, No. 17.

John Eid et al., "Real-Time DNA Sequencing from Single Polymerase Molecules", Science. vol. 323, Jan. 2, 2009, pp. 133-138.

Alex Y. Borovkov et al., "High-quality gene assembly directly from unpurified mixtures of microarray-synthesized oligonucleotides", Nucleic Acids Research, 2010, vol. 38, No. 19.

Kim et al., "A Fluorescence Selection Method for Accurate Large-Gene Synthesis", ChemBioChem 2010, 11, pp. 2448-2452.

Sriram Kosuri et al., "Scalable gene synthesis by selective amplification of DNA pools from high-fidelity microchips", Nature Biotechnology, vol. 28, No. 12, Dec. 2010, pp. 1295-1299.

Mark Matzas et al., "High-fidelity gene synthesis by retrieval of sequence-verified DNA identified using high-throughput pyrosequencing", Nature Biotechnology, vol. 28, No. 12, Dec. 2010, pp. 1291-1294.

Kim et al., "Hierarchial gene synthesis using DNA microchip oligonucleotides", Journal of Biotechnology, 151 (2011), pp. 319-324.

Kim et al., (Hierarchical gene synthesis using DNA microchip oligonucleotides, J Biotechnol. Feb. 20, 2011;151(4):319-24. Epub Jan. 13, 2011.

Kosuri et al., (Scalable gene synthesis by selective amplification of DNA pools from high-fidelity microchips, Nature Biotechnology 28, 1295-1299 (2010), Published online Nov. 28, 2010).

* cited by examiner a. Oligo preparation from chip b. Shot-gun DNA assembly c. Tagging barcode sequences and recovery from DNA mixture d. Assembly to a target gene cluster

SEQUENCE LISTING

<160> NUMBER OF SEQ ID NOS: 284

<210> SEQ ID NO 1
<211> LENGTH: 24
<212> TYPE: DNA
<213> ORGANISM: Artificial Sequence
<220> FEATURE:
<223> OTHER INFORMATION: Synthetic nucelotide

<400> SEQUENCE: 1
gcagagtaaa gaccgtgcac ttat                                            24

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
ctatttgatg ttcgtagttc cag                                             23

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
agccttttca aagcgaaag                                                  19

<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4
atctattagg tcatagtagg cag                                             23

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
catgcagagg aaaccataaa                                                 20

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
tgctattctt tctgcctttt cag                                             23

<210> SEQ ID NO 7
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 7
gaatgtttgt tgcgtttcca                                              20

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
tcgagctcaa tagttttttc ag                                           22

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
tttatgattg cattcagcag cag                                          23

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
ttactccatt ttgcactctc ag                                           22

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
attctttggc ctttgttgac ag                                           22

<210> SEQ ID NO 12
<211> LENGTH: 27
<212> TYPE: DNA
<213> ORGANISM: Artificial Sequence
<220> FEATURE:
<223> OTHER INFORMATION: Synthetic primer

<400> SEQUENCE: 12
ttagtttcaa catgtatata cagcagc                                      27

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
atgtgtatat tcgacacttt cagc                                         24
```

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
gtgaatatcc gtctagcaag c                                    21

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
cagttcacgt tcgtcgcaca ccac                                 24

<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
ctattttcag tgtgcctttt                                      19

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tcctaagttg atgaaacttt                                      20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
tatctggtag gaggggtt                                        18

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tagaactggc aatgacgctg                                      20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ttctgtttgt cttaaatgcg                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
taccgttttt aagattgcgt                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ctgaaattca tttatgtttg                                               20

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
ctatggggta ccttttg                                                  18

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
atattcgagc gtatgtatta                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
aagtgattgt ttacagtctc                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
tcatttcgag aaaaggccga                                               20

<210> SEQ ID NO 27

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
gggttctttc ccttattttg                                                 20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
aacgaggata tacaaatata                                                 20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
aagtgttgag agtggtatat                                                 20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
atggagcttt tatgtggtta                                                 20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
aattgtctag tttcgttgtt                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
tgttggttgt tcaatggagt                                                 20

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
```
atacttgttt caattttgtc cagc                                                24

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
tatttttttc caattttta cagc                                                 24

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
atcctctgct attctgttgc                                                     20

<210> SEQ ID NO 36
<211> LENGTH: 63
<212> TYPE: DNA
<213> ORGANISM: Artificial Sequence
<220> FEATURE:
<223> OTHER INFORMATION: Synthetic primer

<400> SEQUENCE: 36
acctgcatcc agctgattgc gcgtatccgt cagcgtcagc gtttgtctgt gtctatctct        60
gtg                                                                       63

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
gggaaagggt ggtgttgtaa                                                     20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
ctaatttgaa tgcagtccgt                                                     20

<210> SEQ ID NO 39
<211> LENGTH: 21
<212> TYPE: DNA
<213> ORGANISM: Artificial Sequence
<220> FEATURE:
<223> OTHER INFORMATION: Synthetic primer

<400> SEQUENCE: 39
acattacctt tggaaaaaac c                                                   21

<210> SEQ ID NO 40

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
catggaacaa agtgatgctt                                              20

<210> SEQ ID NO 41
<211> LENGTH: 19
<212> TYPE: DNA
<213> ORGANISM: Artificial Sequence
<220> FEATURE:
<223> OTHER INFORMATION: Synthetic primer

<400> SEQUENCE: 41
tccagcagct ggaagactt                                               19

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
ttaagtatga ttaatgctgt ca                                           22

<210> SEQ ID NO 43
<211> LENGTH: 23
<212> TYPE: DNA
<213> ORGANISM: Artificial Sequence
<220> FEATURE:
<223> OTHER INFORMATION: Synthetic primer

<400> SEQUENCE: 43
cgatattgtt cataatatgt cag                                          23

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
tctgcgcttc tcttgggaa                                               19

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
ggcgtaaatc ttccagttta                                              20

<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
```
gtggtatgca cgttggtc                                                    18

<210> SEQ ID NO 47
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or t

<400> SEQUENCE: 47
tatgtgagtg atcnccgttt cag                                              23

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
tggtgcagta gaagaccgta                                                  20

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
tttttcgaac agaagcggta                                                  20

<210> SEQ ID NO 50
<211> LENGTH: 21
<212> TYPE: DNA
<213> ORGANISM: Artificial Sequence
<220> FEATURE:
<223> OTHER INFORMATION: Synthetic primer

<400> SEQUENCE: 50
attacttagg gtattgcgtt c                                                21

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
agaccttcag tctttgcgat                                                  20

<210> SEQ ID NO 52
<211> LENGTH: 22
<212> TYPE: DNA
<213> ORGANISM: Artificial Sequence
<220> FEATURE:
<223> OTHER INFORMATION: Synthetic primer

<400> SEQUENCE: 52
cgtttacctg atcaaacaca gc                                               22

<210> SEQ ID NO 53
<211> LENGTH: 18
<212> TYPE: DNA
<213> ORGANISM: Artificial Sequence
<220> FEATURE:
<223> OTHER INFORMATION: Synthetic primer

<400> SEQUENCE: 53
agctgcactt tatagcgg                                                 18

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
atagcgttat taatttctgt cag                                           23

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
atagttattc ggctagtcct                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
tgctctgtta aacgaacgca                                               20

<210> SEQ ID NO 57
<211> LENGTH: 21
<212> TYPE: DNA
<213> ORGANISM: Artificial Sequence
<220> FEATURE:
<223> OTHER INFORMATION: Synthetic primer

<400> SEQUENCE: 57
ttgcgaccag aaatagtggt g                                             21

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
tcatagagga ggtgctatgg                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 59
cggatcgttt attgactgtt                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60
gatatttcgc ggttctgttg                                               20

<210> SEQ ID NO 61
<211> LENGTH: 23
<212> TYPE: DNA
<213> ORGANISM: Artificial Sequence
<220> FEATURE:
<223> OTHER INFORMATION: Synthetic primer

<400> SEQUENCE: 61
aggtaaaggt tacttaaact cag                                           23

<210> SEQ ID NO 62
<211> LENGTH: 20
<212> TYPE: DNA
<213> ORGANISM: Artificial Sequence
<220> FEATURE:
<223> OTHER INFORMATION: Synthetic primer

<400> SEQUENCE: 62
tagtctttgc cggtttatta                                               20

<210> SEQ ID NO 63
<211> LENGTH: 18
<212> TYPE: DNA
<213> ORGANISM: Artificial Sequence
<220> FEATURE:
<223> OTHER INFORMATION: Synthetic primer

<400> SEQUENCE: 63
ttgcaaagat tctacaga                                                 18

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
ctaaactctt tacttcctat                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
agctcgttat tatgtggctt                                               20

<210> SEQ ID NO 66
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 66
ttatgagaaa tgtttcactg                                               20

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
tagaacacta tcaaatctag                                               20

<210> SEQ ID NO 68
<211> LENGTH: 23
<212> TYPE: DNA
<213> ORGANISM: Artificial Sequence
<220> FEATURE:
<223> OTHER INFORMATION: Synthetic primer

<400> SEQUENCE: 68
tttgtaattt gactctgatg cag                                           23

<210> SEQ ID NO 69
<211> LENGTH: 24
<212> TYPE: DNA
<213> ORGANISM: Artificial Sequence
<220> FEATURE:
<223> OTHER INFORMATION: Synthetic primer

<400> SEQUENCE: 69
taggaatctt ttgactttc acag                                           24

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

<400> SEQUENCE: 70
tactgggagc aaacaattct cag                                           23

<210> SEQ ID NO 71
<211> LENGTH: 22
<212> TYPE: DNA
<213> ORGANISM: Artificial Sequence
<220> FEATURE:
<223> OTHER INFORMATION: Synthetic primer

<400> SEQUENCE: 71
ttcgtctgct gttttcactc ag                                            22

<210> SEQ ID NO 72
<211> LENGTH: 24
<212> TYPE: DNA
<213> ORGANISM: Artificial Sequence
<220> FEATURE:
<223> OTHER INFORMATION: Synthetic primer

<400> SEQUENCE: 72
```
ctaactacgt tttcgatcac ttcg    24

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
ttcacggatt ttgtcgaaga c    21

<210> SEQ ID NO 74
<211> LENGTH: 18
<212> TYPE: DNA
<213> ORGANISM: Artificial Sequence
<220> FEATURE:
<223> OTHER INFORMATION: Synthetic primer

<400> SEQUENCE: 74
gtgggatgga agctcctc    18

<210> SEQ ID NO 75
<211> LENGTH: 23
<212> TYPE: DNA
<213> ORGANISM: Artificial Sequence
<220> FEATURE:
<223> OTHER INFORMATION: Synthetic primer

<400> SEQUENCE: 75
tgtattatgt cctttttgcc agc    23

<210> SEQ ID NO 76
<211> LENGTH: 57
<212> TYPE: DNA
<213> ORGANISM: Artificial Sequence
<220> FEATURE:
<223> OTHER INFORMATION: Synthetic primer

<400> SEQUENCE: 76
gctttcagcg agccggtctt cgacaaaatc cgtgaaacct tccacggttt ggttatc    57

<210> SEQ ID NO 77
<211> LENGTH: 18
<212> TYPE: DNA
<213> ORGANISM: Artificial Sequence
<220> FEATURE:
<223> OTHER INFORMATION: Synthetic primer

<400> SEQUENCE: 77
caggtacagc tcacccac    18

<210> SEQ ID NO 78
<211> LENGTH: 20
<212> TYPE: DNA
<213> ORGANISM: Artificial Sequence
<220> FEATURE:
<223> OTHER INFORMATION: Synthetic primer

<400> SEQUENCE: 78
tgttggatat atagggttac    20

<210> SEQ ID NO 79
<211> LENGTH: 20
<212> TYPE: DNA

<213> ORGANISM: Artificial Sequence
<220> FEATURE:
<223> OTHER INFORMATION: Synthetic primer

<400> SEQUENCE: 79
catggggatg atgtgtactt                                               20

<210> SEQ ID NO 80
<211> LENGTH: 20
<212> TYPE: DNA
<213> ORGANISM: Artificial Sequence
<220> FEATURE:
<223> OTHER INFORMATION: Synthetic primer

<400> SEQUENCE: 80
aattcactca gaataatttt                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic primer

<400> SEQUENCE: 81
atttagttgg aattaatctc                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
ctactgttcg ttcccaatta                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
ttggtgtaaa actgggggaa                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer

<400> SEQUENCE: 84
atgtgttata gaagttgttg                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic primer

<400> SEQUENCE: 85
tgacatgtgt tatccctgct                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic primer

<400> SEQUENCE: 86
tttcagaaac ttaaacttac                                                 20

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
ttataagaag taataggaat                                                 20

<210> SEQ ID NO 88
<211> LENGTH: 20
<212> TYPE: DNA
<213> ORGANISM: Artificial Sequence
<220> FEATURE:
<223> OTHER INFORMATION: Synthetic primer

<400> SEQUENCE: 88
tatacaatct attggtaatc                                                 20

<210> SEQ ID NO 89
<211> LENGTH: 20
<212> TYPE: DNA
<213> ORGANISM: Artificial Sequence
<220> FEATURE:
<223> OTHER INFORMATION: Synthetic primer

<400> SEQUENCE: 89
tggaatactt taatcctttc                                                 20

<210> SEQ ID NO 90
<211> LENGTH: 20
<212> TYPE: DNA
<213> ORGANISM: Artificial Sequence
<220> FEATURE:
<223> OTHER INFORMATION: Synthetic primer

<400> SEQUENCE: 90
ttacatgctt tcgacacata                                                 20

<210> SEQ ID NO 91
<211> LENGTH: 20
<212> TYPE: DNA
<213> ORGANISM: Artificial Sequence
<220> FEATURE:
<223> OTHER INFORMATION: Synthetic primer

<400> SEQUENCE: 91
tgtatagtgt gaggatcttt                                                 20

<210> SEQ ID NO 92
<211> LENGTH: 20
<212> TYPE: DNA
<213> ORGANISM: Artificial Sequence
<220> FEATURE:

<223> OTHER INFORMATION: Synthetic primer

<400> SEQUENCE: 92
gttaatttct ggggatacgt                                           20

<210> SEQ ID NO 93
<211> LENGTH: 20
<212> TYPE: DNA
<213> ORGANISM: Artificial Sequence
<220> FEATURE:
<223> OTHER INFORMATION: Synthetic primer

<400> SEQUENCE: 93
taactcacgc ttttataag                                            20

<210> SEQ ID NO 94
<211> LENGTH: 22
<212> TYPE: DNA
<213> ORGANISM: Artificial Sequence
<220> FEATURE:
<223> OTHER INFORMATION: Synthetic primer

<400> SEQUENCE: 94
ttcttgtcac tctctttatc ca                                        22

<210> SEQ ID NO 95
<211> LENGTH: 19
<212> TYPE: DNA
<213> ORGANISM: Artificial Sequence
<220> FEATURE:
<223> OTHER INFORMATION: Synthetic primer

<400> SEQUENCE: 95
tctatcggtt ttcgggttt                                            19

<210> SEQ ID NO 96
<211> LENGTH: 23
<212> TYPE: DNA
<213> ORGANISM: Artificial Sequence
<220> FEATURE:
<223> OTHER INFORMATION: Synthetic primer

<400> SEQUENCE: 96
gaagcacctg tcttatttaa cag                                       23

<210> SEQ ID NO 97
<211> LENGTH: 18
<212> TYPE: DNA
<213> ORGANISM: Artificial Sequence
<220> FEATURE:
<223> OTHER INFORMATION: Synthetic primer

<400> SEQUENCE: 97
tgatcttccc gggtaggc                                             18

<210> SEQ ID NO 98
<211> LENGTH: 21
<212> TYPE: DNA
<213> ORGANISM: Artificial Sequence
<220> FEATURE:
<223> OTHER INFORMATION: Synthetic primer

<400> SEQUENCE: 98
ggtcgttctg cgtgtagata t                                         21

```
<210> SEQ ID NO 99
<211> LENGTH: 21
<212> TYPE: DNA
<213> ORGANISM: Artificial Sequence
<220> FEATURE:
<223> OTHER INFORMATION: Synthetic primer

<400> SEQUENCE: 99
ctgcagcagt ttcgtaactt c                                              21

<210> SEQ ID NO 100
<211> LENGTH: 20
<212> TYPE: DNA
<213> ORGANISM: Artificial Sequence
<220> FEATURE:
<223> OTHER INFORMATION: Synthetic primer

<400> SEQUENCE: 100
tcatcctatt acgatgcccg                                                20

<210> SEQ ID NO 101
<211> LENGTH: 20
<212> TYPE: DNA
<213> ORGANISM: Artificial Sequence
<220> FEATURE:
<223> OTHER INFORMATION: Synthetic primer

<400> SEQUENCE: 101
gcgttggaag cttttttattg                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic primer

<400> SEQUENCE: 102
atttataagg acgggccagc                                                20

<210> SEQ ID NO 103
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t

<400> SEQUENCE: 103
aaacgntccc cgtattggta                                                20

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
taatctgatc gatgctagga                                                20

<210> SEQ ID NO 105
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 105
ttttgattca atcctcctaa                                                    20

<210> SEQ ID NO 106
<211> LENGTH: 22
<212> TYPE: DNA
<213> ORGANISM: Artificial Sequence
<220> FEATURE:
<223> OTHER INFORMATION: Synthetic primer

<400> SEQUENCE: 106
tttcctattt cttcattggc ag                                                 22

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
ttgcgatggt ttactttgat                                                    20

<210> SEQ ID NO 108
<211> LENGTH: 20
<212> TYPE: DNA
<213> ORGANISM: Artificial Sequence
<220> FEATURE:
<223> OTHER INFORMATION: Synthetic primer

<400> SEQUENCE: 108
atcattgcac ttgttgttcg                                                    20

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
ggaaggtttt ttactgattt                                                    20

<210> SEQ ID NO 110
<211> LENGTH: 20
<212> TYPE: DNA
<213> ORGANISM: Artificial Sequence
<220> FEATURE:
<223> OTHER INFORMATION: Synthetic primer

<400> SEQUENCE: 110
ttattcgtgg attggtgttc                                                    20

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111 attttttctag gttctgatta                                                   20
```

<210> SEQ ID NO 112
<211> LENGTH: 19
<212> TYPE: DNA
<213> ORGANISM: Artificial Sequence
<220> FEATURE:
<223> OTHER INFORMATION: Synthetic primer

<400> SEQUENCE: 112
tgatttcacc actaagtct                                                  19

<210> SEQ ID NO 113
<211> LENGTH: 19
<212> TYPE: DNA
<213> ORGANISM: Artificial Sequence
<220> FEATURE:
<223> OTHER INFORMATION: Synthetic primer

<400> SEQUENCE: 113
cctcctttat ttctcgtgc                                                  19

<210> SEQ ID NO 114
<211> LENGTH: 20
<212> TYPE: DNA
<213> ORGANISM: Artificial Sequence
<220> FEATURE:
<223> OTHER INFORMATION: Synthetic primer

<400> SEQUENCE: 114
taaagttatc atgtgctacc                                                 20

<210> SEQ ID NO 115
<211> LENGTH: 20
<212> TYPE: DNA
<213> ORGANISM: Artificial Sequence
<220> FEATURE:
<223> OTHER INFORMATION: Synthetic primer

<400> SEQUENCE: 115
tgtaaaccta tattcatctc                                                 20

<210> SEQ ID NO 116
<211> LENGTH: 23
<212> TYPE: DNA
<213> ORGANISM: Artificial Sequence
<220> FEATURE:
<223> OTHER INFORMATION: Synthetic primer

<400> SEQUENCE: 116
gttcattgca taatgcttct cag                                             23

<210> SEQ ID NO 117
<211> LENGTH: 24
<212> TYPE: DNA
<213> ORGANISM: Artificial Sequence
<220> FEATURE:
<223> OTHER INFORMATION: Synthetic primer

<400> SEQUENCE: 117
ttaaagccct ttacatccag cagc                                            24

<210> SEQ ID NO 118
<211> LENGTH: 21
<212> TYPE: DNA
<213> ORGANISM: Artificial Sequence
<220> FEATURE:

<223> OTHER INFORMATION: Synthetic primer

<400> SEQUENCE: 118
ctaacccgtt ctgcaaggaa g                                                    21

<210> SEQ ID NO 119
<211> LENGTH: 16
<212> TYPE: DNA
<213> ORGANISM: Artificial Sequence
<220> FEATURE:
<223> OTHER INFORMATION: Synthetic primer

<400> SEQUENCE: 119
cggctgctgc tggcgg                                                          16

<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
attgatatgt aagagatttc                                                      20

<210> SEQ ID NO 121
<211> LENGTH: 19
<212> TYPE: DNA
<213> ORGANISM: Artificial Sequence
<220> FEATURE:
<223> OTHER INFORMATION: Synthetic primer

<400> SEQUENCE: 121
aataggtacc attttcgtt                                                       19

<210> SEQ ID NO 122
<211> LENGTH: 23
<212> TYPE: DNA
<213> ORGANISM: Artificial Sequence
<220> FEATURE:
<223> OTHER INFORMATION: Synthetic primer

<400> SEQUENCE: 122
gattactaca ttttctcaa cag                                                   23

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
cttttggggg gggttgggcc                                                      20

<210> SEQ ID NO 124
<211> LENGTH: 17
<212> TYPE: DNA
<213> ORGANISM: Artificial Sequence
<220> FEATURE:
<223> OTHER INFORMATION: Synthetic primer

<400> SEQUENCE: 124
cgtttatggg aaagcgc                                                         17

```
<210> SEQ ID NO 125
<211> LENGTH: 21
<212> TYPE: DNA
<213> ORGANISM: Artificial Sequence
<220> FEATURE:
<223> OTHER INFORMATION: Synthetic primer

<400> SEQUENCE: 125
gctatccttc atgaaaacgt g                                           21

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
aattggttac ctctatcccc                                             20

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
ctcatactgg gatccgattt                                             20

<210> SEQ ID NO 128
<211> LENGTH: 20
<212> TYPE: DNA
<213> ORGANISM: Artificial Sequence
<220> FEATURE:
<223> OTHER INFORMATION: Synthetic primer

<400> SEQUENCE: 128
gcataaagcg ggaggcttct                                             20

<210> SEQ ID NO 129
<211> LENGTH: 19
<212> TYPE: DNA
<213> ORGANISM: Artificial Sequence
<220> FEATURE:
<223> OTHER INFORMATION: Synthetic primer

<400> SEQUENCE: 129
ctgtgtcata gaatagtgc                                              19

<210> SEQ ID NO 130
<211> LENGTH: 20
<212> TYPE: DNA
<213> ORGANISM: Artificial Sequence
<220> FEATURE:
<223> OTHER INFORMATION: Synthetic primer

<400> SEQUENCE: 130
tttcgaccga tttcagtctg                                             20

<210> SEQ ID NO 131
<211> LENGTH: 17
<212> TYPE: DNA
<213> ORGANISM: Artificial Sequence
<220> FEATURE:
<223> OTHER INFORMATION: Synthetic primer
```

<400> SEQUENCE: 131 tttttttgacg gtaatta                                                17

<210> SEQ ID NO 132
<211> LENGTH: 18
<212> TYPE: DNA
<213> ORGANISM: Artificial Sequence
<220> FEATURE:
<223> OTHER INFORMATION: Synthetic primer

<400> SEQUENCE: 132
cttcctgtgg gttttcta                                                18

<210> SEQ ID NO 133
<211> LENGTH: 20
<212> TYPE: DNA
<213> ORGANISM: Artificial Sequence
<220> FEATURE:
<223> OTHER INFORMATION: Synthetic primer

<400> SEQUENCE: 133
ttttacatca ttcgcgtatt                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
tttttgagct acgctttcgg                                              20

<210> SEQ ID NO 135
<211> LENGTH: 17
<212> TYPE: DNA
<213> ORGANISM: Artificial Sequence
<220> FEATURE:
<223> OTHER INFORMATION: Synthetic primer

<400> SEQUENCE: 135
tcaatacatt ctactt                                                  17

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
gtcagtagta taccgttcgt                                              20

<210> SEQ ID NO 137
<211> LENGTH: 20
<212> TYPE: DNA
<213> ORGANISM: Artificial Sequence
<220> FEATURE:
<223> OTHER INFORMATION: Synthetic primer

<400> SEQUENCE: 137
cgatctaaga ttgccttcct                                              20

<210> SEQ ID NO 138
<211> LENGTH: 23

```
<212> TYPE: DNA
<213> ORGANISM: Artificial Sequence
<220> FEATURE:
<223> OTHER INFORMATION: Synthetic primer

<400> SEQUENCE: 138
tctcataatt gggaattgta cag                                             23

<210> SEQ ID NO 139
<211> LENGTH: 23
<212> TYPE: DNA
<213> ORGANISM: Artificial Sequence
<220> FEATURE:
<223> OTHER INFORMATION: Synthetic primer

<400> SEQUENCE: 139
tttatgtttt tgaattagca gca                                             23

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
atcttttatg tactttgtga                                                 20

<210> SEQ ID NO 141
<211> LENGTH: 20
<212> TYPE: DNA
<213> ORGANISM: Artificial Sequence
<220> FEATURE:
<223> OTHER INFORMATION: Synthetic primer

<400> SEQUENCE: 141
tttttcaaca cttttagtgt                                                 20

<210> SEQ ID NO 142
<211> LENGTH: 17
<212> TYPE: DNA
<213> ORGANISM: Artificial Sequence
<220> FEATURE:
<223> OTHER INFORMATION: Synthetic primer

<400> SEQUENCE: 142
taatttcctg tgcaact                                                    17

<210> SEQ ID NO 143
<211> LENGTH: 20
<212> TYPE: DNA
<213> ORGANISM: Artificial Sequence
<220> FEATURE:
<223> OTHER INFORMATION: Synthetic primer

<400> SEQUENCE: 143
tcttgtttat ttctttgggt                                                 20

<210> SEQ ID NO 144
<211> LENGTH: 23
<212> TYPE: DNA
<213> ORGANISM: Artificial Sequence
<220> FEATURE:
<223> OTHER INFORMATION: Synthetic primer

<400> SEQUENCE: 144
```

```
atgtatcctc gctctttaac cag                                          23
```

<210> SEQ ID NO 145
<211> LENGTH: 22
<212> TYPE: DNA
<213> ORGANISM: Artificial Sequence
<220> FEATURE:
<223> OTHER INFORMATION: Synthetic primer

<400> SEQUENCE: 145

```
cacccggttt gattattact ca                                           22
```

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146

```
ggcattctgg cgatggagat                                              20
```

<210> SEQ ID NO 147
<211> LENGTH: 21
<212> TYPE: DNA
<213> ORGANISM: Artificial Sequence
<220> FEATURE:
<223> OTHER INFORMATION: Synthetic primer

<400> SEQUENCE: 147

```
gtcgtagtac tcatacaggc g                                            21
```

<210> SEQ ID NO 148
<211> LENGTH: 21
<212> TYPE: DNA
<213> ORGANISM: Artificial Sequence
<220> FEATURE:
<223> OTHER INFORMATION: Synthetic primer

<400> SEQUENCE: 148

```
ctaacgcatt gtcaggtttc c                                            21
```

<210> SEQ ID NO 149
<211> LENGTH: 22
<212> TYPE: DNA
<213> ORGANISM: Artificial Sequence
<220> FEATURE:
<223> OTHER INFORMATION: Synthetic primer

<400> SEQUENCE: 149

```
actccggata ccagtgtaga ac                                           22
```

<210> SEQ ID NO 150
<211> LENGTH: 53
<212> TYPE: DNA
<213> ORGANISM: Artificial Sequence
<220> FEATURE:
<223> OTHER INFORMATION: Synthetic primer

<400> SEQUENCE: 150

```
gaatcagaaa accagcgtcg cctgtatgag tactacgacg cgttagattc cac         53
```

<210> SEQ ID NO 151
<211> LENGTH: 31
<212> TYPE: DNA
<213> ORGANISM: Artificial Sequence

```
<220> FEATURE:
<223> OTHER INFORMATION: Synthetic primer

<400> SEQUENCE: 151
ttacttccaa cgaccgatgt actgagccgc c                              31

<210> SEQ ID NO 152
<211> LENGTH: 392
<212> TYPE: DNA
<213> ORGANISM: Artificial Sequence
<220> FEATURE:
<223> OTHER INFORMATION: Synthetic nucleotide

<400> SEQUENCE: 152
ctatttgatg ttcgtagttc cagcagcacc gactaatgca ggctggcagt aatgacccaa    60
ttgaagccgc ctaacgggac cactccgatc ggcttcagcg ccactactag cctgaacgct   120
agcggctctt cctcggttaa gaatggtacc atcaagcctt cgaatggtat cttcaaacct   180
tctactcgtg acaccatgga cccgtgctcg ggcaacgccg ctgacggctc cattcgcgta   240
cgttttcgcg gtggcatcga acgttggaaa gagtgtgtaa accaagtgcc ggagcgttgc   300
gacctgtctg gtctgaccac ggacagcacc cgctaccagc tggcttccga acacatgacc   360
ctgcgacctg ctgagccttt tcaaagcgaa ag                                392

<210> SEQ ID NO 153
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 153
atctattagg tcatagtagg cagcagaggg catcttagcg gtcgctcttc tggcttcggc    60
gacgcgagcg cggcttacca ggaacgtctg atgactgtgc cggtagatgt tcatgctgcg   120
ctccaggagc tgtgcctgga acgccgcgtc tctgtgggtt ctgtgatcaa cttcagcgtt   180
caccagatgc tgaagggttt tggcaacggt actcacacta tcaccgcgag cctgcaccgc   240
gaacagaatc tgcagaactc ctctccgtct tgggtcgttt ccctactat cgtgacccat    300 gaaaaccgcg atggctggtc agtggcgcag gcagtggagt ctatcgaggc tagaagacca   360
cacatggcac ctttgctgct gcatgcagag gaaaccataa at                      402

<210> SEQ ID NO 154
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 154
tgctattctt tctgcctttt cagcagcaaa ggtgccatgt gtggctcttc tggcaacggt    60
actcacacta tcaccgcgag cctgcaccgc gaacagaatc tgcagaactc ctctccgtct   120
tgggtcgttt ccctactat cgtgacccat gaaaaccgcg atggctggtc agtggcgcag    180
gcagtggagt ctatcgaggc tggtcgtggc tccgaaaagg aatctgtgac cgcgattgat   240
tccggctcct ccctggtcaa aatgggtctg ttcgatctgc tggtttcctt cgtcgatgcg   300
gatgacgcgc gtatcccttg cttcgacttt ccgctggctg ttattgtgcg cagaagagcg   360
accgctaaga tgccctctgc tgtggaaacg caacaaacat tc                      402
```

<210> SEQ ID NO 155
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 155

```
tcgagctcaa tagttttttc agcagcaccg actaatgcag gctggcgtga tgacgcgcgt    60
atcccttgct tcgactttcc gctggctgtt attgtgcgcg agtgcgatgc aaacctgtct   120
ctcacccttc gcttctcgga ctgcctgttc aacgaggaaa ccatttgtaa tttcacggat   180
gccctcaata tcctgttggc tgaggcagtt atcggtcgtg taactccggt agccgatatc   240
gagctgctgt ctgcagagca gaaacaacag ctggaggaat ggaacaacac cgatggtgaa   300
tatccgtcta gcaagcgtct gcaccacctg attgaagagg tggtggaacc actgcgaaca   360
catgaccctg cgacctgctg ctgctgaatg caatcataaa                         400
```

<210> SEQ ID NO 156
<211> LENGTH: 389
<212> TYPE: DNA
<213> ORGANISM: Artificial Sequence
<220> FEATURE:
<223> OTHER INFORMATION: Synthetic nucleotide

<400> SEQUENCE: 156

```
ttactccatt ttgcactctc agcagcaccg actaatgcag gctggcatga tgacgcgcgt    60
atcccttgct tcgactttcc gctggctgtt attgtgcgcg agtgcgatgc aaacctgtct   120
ctcacccttc gcttctcttc aacgaggaaa ccatttgtaa tttcacggat gccctcaata   180
tcctgttggc tgaggcagtt atcggtcgtg taactccggt agccgatatc gagctgctgt   240
ctgcagagca gaaacaacag ctggaggaat ggaacaacac cgatggtgaa tatccgtcta   300
gcaagcgtct gcaccacctg attgaagagg tggtggaacc actacgaaca catgaccctg   360
cgacctgctg tcaacaaagg ccaaagaat                                     389
```

<210> SEQ ID NO 157
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 157

```
ttagtttcaa catgtatata cagcagcacc gactaatgca ggctggagtg caacgaggaa    60
accatttgta atttcacgga tgccctcaat atcctgttgg ctgaggcagt tatcggtcgt   120
gtaactccgg tagccgatat cgagctgctg tctgcagagc agaaacaaca gctggaggaa   180
tggaacaaca ccgatggtga atatccgtct agcaagcgtc tgcaccacct gattgaagag   240
gtggtggaac gtcacgaaga caaatcgct gtggtgcg acgaacgtga actgacttac     300
ggtgaactca atgcccacgg caactccctg gcgcgttacc tgcacagcat cactgcgaac   360
acatgaccct gcgacctgct gaaagtgtcg aatatacaca t                       401
```

<210> SEQ ID NO 158
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 158

```
ctattttcag tgtgcctttc agcagcaccg actaatgcag gctggagtgg tcacgaagac      60
aaaatcgctg tggtgtgcga cgaacgtgaa ctgacttacg gtgaactcaa tgcccagggc     120
aactccctgg cgcgttacct gcgcagcatt ggtattctgc ctgaacagct ggttgcgctg     180
tttctggaca aatccgaaaa attgatcgta accatcctgg gcgtctggaa atccggtgct     240
gcttacgtgc caattgaccc gacctaccct gacgaacgtg ttcgtttcgt tctggacgac     300
acgaaagccc gtgcgattat cgcttccaat cagcatgttg aacgcctccc actgcgaaca     360
catgaccctg cgacctgctg aaagtttcat caacttagga                            400
```

<210> SEQ ID NO 159
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 159

```
tatctggtag gaggggttca gcagcaaagg tgccatgtgt ggctcttcta attgatcgta      60
accatcctgg gcgtctggaa atccggtgct gcttacgtgc caattgaccc gacctaccct     120
gacgaacgtg ttcgtttcgt tctggacgac acgaaagccc gtgcgattat cgcttccaat     180
cagcatgttg aacgcctcca gcgtgaagta atcggtgatc gcaacctgtg catcatccgt     240
ctcgaaccac tgctggcgag ccttgcgcag gattcttcta aattccctgc ccacaacctg     300
gatgatttgc cgctgaccag ccagcagctg gcgtacgtta cttataccaa gaagagtgac     360
cgctaagatg ccctctgctg cagcgtcatt gccagttcta                            400
```

<210> SEQ ID NO 160
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 160

```
ttctgtttgt cttaaatgcg cagcagaggg catcttagcg gtcgctcttc tagcgtgaag      60
taatcggtga tcgcaacctg tgcatcatcc gtctcgaacc actgctggcg agccttgcgc     120
aggattcttc taaattccct gcccacaacc tggatgattt gccgctgacc agccagcagc     180
tggcgtacgt tacttatacc agcggtacca ccggctttcc gaaaggcatt ttcaaacagc     240
acactaacgt tgttaactcc atcacagacc tgtccgctcg ttacggtgtt gcaggtcaac     300
accatgaagc tatcctgctc ttcagtgctt gcgttttcga accgttcgtt cagaagagcc     360
acacatggca cctttgctgc tgacgcaatc ttaaaaacgg ta                         402
```

<210> SEQ ID NO 161
<211> LENGTH: 383
<212> TYPE: DNA
<213> ORGANISM: Artificial Sequence
<220> FEATURE:
<223> OTHER INFORMATION: Synthetic nucleotide

<400> SEQUENCE: 161

```
ctgaaattca tttatgtttg cagcagcacc gactaatgca ggctggcagt ggttaactcc      60
atcacagacc tgtccgctcg ttacggtgtt gcaggtcaac accatgaagc tatcctgctc     120
```

```
ttcagtgctt gcgttttcga accgttcgtt cgtcagactc tgatggccct ggtgaacggt      180
cacctgctcg ccgtgattaa cgatgtagaa aaatatgacg ctgacaccct cctcccattt      240
atccgccgtc actctatcac ctatctgaac ggtactgcgt cggttctcca agagtatgac      300
ttctctgact gtccgagcct gaaccgtatc atcctctgcg aacacatcga ccctgcgacc      360
tgctgcaaaa aggtaccccca tag                                             383
```

<210> SEQ ID NO 162
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 162

```
atattcgagc gtatgtatta cagcagcacc gactaatgca ggctggcgtc tctatcacct      60
atctgaacgg tactgcgtcg gttctccaag agtatgactt ctctgactgt ccgagcctga     120
accgtatcat cctggtgggc gagaacctga ccgaagcacg ttacctggca ctgcgtcagc     180
gtttcaaaaa tcgtattctg aacgagtacg gtttcaccga gtctgcgttc gtgactgcgc     240
tgaaaatttt cgatccggaa agcacccgca agatacctc cctggggcgt ccggtgcgca     300
atgttaaatg ctatatcttg aaccctagcc tgaaacgcgt gccaattggc atgcgaacac     360
atgaccctgc gacctgctgg agactgtaaa caatcactt                            399
```

<210> SEQ ID NO 163
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 163

```
tcatttcgag aaaaggccga cagcaggtcg cagggtcatg tgttcgcagt ggaacgagta      60
cggtttcacc gagtctgcgt tcgtgactgc gctgaaaatt ttcgatccgg aaagcacccg     120
caaagatacc tccctggggc gtccggtgcg caatgttaaa tgctatatct tgaaccctag     180
cctgaaacgc gtgccaattg gtgctacagg tgagctgcat attggcggcc tgggtatctc     240
caagggttac ttgaatcgtc cggaactgac gccgcaccgc ttcatcccga acccgtttca     300
gaccgattgc gaaaaacagc tgggtatcaa ctctctgatg tacaaaaccg gcactgtcag     360
cctgcattag tcggtgctgc tgcaaaataa gggaaagaac cc                        402
```

<210> SEQ ID NO 164
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 164

```
aacgaggata tacaaatata cagcagcaaa ggtgccatgt gtggctcttc ttgaatcgtc      60
cggaactgac gccgcaccgc ttcatcccga acccgtttca gaccgattgc gaaaaacagc     120
tgggtatcaa ctctctgatg tacaaaaccg gtgatctggc tcgctggctc ccgaacggtg     180
aagttgaata cctgggccgt gcggattcc agatcaaact gcgcggtatt cgtattgagc     240
cgggcgaaat cgagactatg ctggcgatgt atccgcgcgt tcgtacctcc ctggtggttt     300
ccaagaaatt acgtaacggt cctgaagaaa caacgaacga acacctggta gagaagagcg     360
```
accgctaaga tgccctctgc tgatatacca ctctcaacac tt        402

<210> SEQ ID NO 165
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 165
atggagcttt tatgtggtta cagcagagga catcttagcg gtcgctcttc tcggatttcc        60
agatcaaact gcgcggtatt cgtattgagc cgggcgaaat cgagactatg ctggcgatgt        120
atccgcgcgt tcgtacctcc ctggtggttt ccaagaaatt acgtaacggt cctgaagaaa        180
caacgaacga acacctggta ggctactacg tatgcgactc cgcatctgtt ccgaagcgg        240 atctgctgtc cttcctggag aagaagctgc cgcgttatat gattccgact cgtctggtac        300
agctgagcca gatcccggtt aacgtcaacg gtaaagccga tctgcgtgct cagaagagcc        360
acacatggca cctttgctgc tgaacaacga aactagacaa tt        402

<210> SEQ ID NO 166
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 166
tgattatggt ggttgcggtg cagcagcacc gactaatgca ggctggcagt gttcctggag        60
aagaagctgc cgcgttatat gattccgact cgtctggtac agctgagcca gatcccggtt        120
aacgtcaacg gtaaagccga tctgcgtgct ctgccggcgg ttgatatctc caacagcacc        180
gaagttcgtt ctgatctgcg tggtgatacc gaaattgccc tcggcgaaat ctgggcggac        240
gtgctgggcg cgcgtcagcg ttcggttagc cgtaacgata acttttttccg cctcggtggc        300 cactctatca cctgcatcca gctgattgcg cgtatccgtc agcgtcagcg tcactgcgaa        360
cacatgaccc tgcgacctgc tgcagaataa ctaaattagt at        402

<210> SEQ ID NO 167
<211> LENGTH: 439
<212> TYPE: DNA
<213> ORGANISM: Artificial Sequence
<220> FEATURE:
<223> OTHER INFORMATION: Synthetic nucleotide

<400> SEQUENCE: 167 tattttttc caattttta cagcagcacc gactaatgca ggctggcaac ctgcatccag        60
ctgattgcgc gtatccgtca gcgtcagcgt tgtctgtgt ctatctctgt ggaagacgtg        120
tttgctacac gcactcttga gcgtatggcc gacctgttgc aaaacaaaca gcaagagaaa        180
tgcgacaaac cacacgaagc accgactgaa ctgcttgaag aaaacgctgc gactgataac        240
atctacctgg cgaacagcct gcagcaaggt ttcgtctacc attacctgaa aagcatggaa        300
caaagtgatg cttatgtaat gcagagcgtt ctgcgttaca acaccaccct ttcccggatc        360
tgttccagcg tgcctggaaa cacgcgcagc ctgcgaacac atgaccctgc gacctgctgg        420
caacagaata gcagaggat        439

<210> SEQ ID NO 168

<211> LENGTH: 413
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (282)..(282)
<223> OTHER INFORMATION: n is a, c, g, or t

<400> SEQUENCE: 168

```
ctaatttgaa tgcagtccgt cagcagcacc gactaatgca ggctggcagt aagcatggaa    60
caaagtgatg cttatgtaat gcagagcgtt ctgcgttaca acaccaccct ttccccggat   120
ctgttccagc gtgcctggaa acacgcgcag caaagcttcc cggctctgcg tctgcgcttc   180
tcttgggaaa aagaagtctt ccagctgctg gatcaggac cgcctctgg actggcgttt    240
cctctacttc actgatgtgg tggcaggtgc agatccccgt tntcagtcgg gcgaaccagt   300
gacagctggg tatcttcgtt gatgcctcag cgctcagttc ggacagctga cgcagaaggt   360
acactgcgaa cacatgaccc ttcgacctgc ttggtttttt ccaaaggtaa tgt          413
```

<210> SEQ ID NO 169
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 169

```
ttaagtatga ttaatgctgt cagcagcacc gactaatgca ggctggcgtg caaagcttcc    60
cggctctgcg tctgcgcttc tcttgggaaa aagaagtctt ccagctgctg gatcaggacc   120
cgcctctgga ctggcgtttc ctctacttca ctgatgtggc ggctggtgca gtagaagacc   180
gtaaactgga agatttacgc caccaggacc tcaccgagcg ttttaaactg gatgtgggcc   240
gtctgtttcg cgtttacctg atcaaacaca gcgaaaaccg tttcacttgt ctgttctctt   300
gtcacccgct atcctggacg gctggtcctt accgcttctg ttcgaaaacc ctgcgaacac   360
atgaccctgc gacctgctga catattatga acaatatcg                          399
```

<210> SEQ ID NO 170
<211> LENGTH: 401
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t

<400> SEQUENCE: 170

```
gtggtatgca cgttggtcct cagcagcacc gactaatgca ggctggcagt ccaaagcttc    60
ccggctctgc gtctgcgctt ctcttgggaa aaagaagtct tccagctgct ggatcaggac   120
ccgcctctgg actggcgttt cctctacttc actgatgtgg cgctggtgca gtagaagacc   180
gtaaactgga agatttacgc cgccaggacc tcaccgagcg ttttaaactg gatgtgggcc   240
gtctgtttcg cgtttacctg atcaaacaca gcgaaaaccg tttcacttgt ctgttctctt   300
gtcaccacgc tatcctggac ggctggtcct taccgcttct gttcgaaaaa cnctgcgaac   360
```
acatgaccct gcgacctgct gaaacggnga tcactcacat a                401

<210> SEQ ID NO 171
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 171
attacttagg gtattgcgtt cagcagcacc gactaatgca ggctggcagg cgtttacctg    60
atcaaacaca gcgaaaaccg tttcacttgt ctgttctctt gtcaccacgc tatcctggac   120
ggctggtcct taccgcttct gttcgaaaaa gtacacgaaa catacctgca actgctgcac   180
ggcgataacc tgacctcctc tatggatgat ccatacaccc gtacccaacg ctacctgcat   240
gcgcaccgcg aagatcacct cgacttttgg gctggcgtgg tgcagaaaat caacgaacgt   300
tgcgatatga atgctctgtt aaacgaacgc agccgctata agtgcagct cactgcgaac    360 acatgaccct gcgacctgct gatcgcaaag actgaaggtc t                401

<210> SEQ ID NO 172
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 172
atagcgttat taatttctgt cagcagaggg catcttaggg gtcgctcttc taagatcacc    60
tcgacttttg ggctggcgtg gtgcagaaaa tcaacgaacg ttgcgatatg atgctctgtt   120
aaacgaacgc agccgctata agtgcagct ggccgactac gatcaggtac aggaacagcg    180
tcagctgacg atcgctctga gcggtgacgc gtggctggcg gatctgcgcc agacatgcag   240
tgcgcagggc atcacgctgc actctatcct gcaatttgta tggcatgcag ttctgcatgc   300
ctacggtggc ggtactcaca ctatcactgg caccactatt tctggtcgca agaagcgcca   360
cacatggcac ctttgctgct gaggactagc cgaataacta t                 401

<210> SEQ ID NO 173
<211> LENGTH: 390
<212> TYPE: DNA
<213> ORGANISM: Artificial Sequence
<220> FEATURE:
<223> OTHER INFORMATION: Synthetic nucleotide

<400> SEQUENCE: 173
tcatagagga ggtgctatgg cagcaggtcg cagggtcatg tgttcgcagt gctacggtgg    60
cggtactcac actatcactg gcaccactat ttctggtcgc aacctcccga tcctgggtat   120
cgagcgtgcg gtaggcccgt acattaacac cctgccgtta gtgttggacc attctacttt   180
taaagacaag acgatcatgg aagctattga agacgtccaa gcgaaggtga atgttatgaa   240
ctcccgtggt aatgtagaac tgggtcgcct gcacaaaacc gacctgaaac atggcctgtt   300
cgattctctg tttgtgctgg aaaactatcc aaacctggat aaatccagcc tgcattagtc   360
ggtgctgctg aacagtcaat aaacgatccg                         390

<210> SEQ ID NO 174
<211> LENGTH: 401
<212> TYPE: DNA

```
<213> ORGANISM: Artificial Sequence
<220> FEATURE:
<223> OTHER INFORMATION: Synthetic nucleotide

<400> SEQUENCE: 174
gatatttcgc ggttctgttg cagcagcacc gactaatgca ggctggcagt agctattgaa    60
gacgtccaag cgaaggtgaa tgttatgaac tcccgtggta atgtagaact gggtcgcctg   120
cacaaaaccg acctgaaaca tggcctgttc gattctctgt ttgtgctgga aaactatcca   180
aacctggata atcccgtac tctggagcac caaactgaac tgggttactc catcgagggt    240
ggtaccgaaa actgaacta tccgctggcg gtgattgctc gtgaggttga gaccactggc    300
ggctttactg ttagcatctg ctatgcgagc gaactgtttg aagaggtgat cactgcgaac   360
acatgaccct gcgacctgct gagtttaagt aacctttacc t                      401

<210> SEQ ID NO 175
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 175
tagtctttgc cggtttatta cagcagcacc gactaatgca ggctggcagt gaactgaact    60
atccgctggc ggtgattgct cgtgaggttg agaccactgg cggctttact gttagcatct   120
gctatgcgag cgaactgttt gaagaggtga tgatcagcga gcttctccat atggtacagg   180
atacctgat gcaggttgca cgcgggctca acgaacctgt gggctccctg gaatacctgt    240
cttccatcca gttagagcag ctggcagcgt ggaacgccac cgaagcggag ttcccggaca   300
cgaccctgca tgaaatgttc gagaacgaag catctcaaaa gccggataaa acactgcgaa   360
cacatgaccc tgcgacctgc tgtctgtaga atctttgcaa                        400

<210> SEQ ID NO 176
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 176
ctaaactctt tacttcctat cagcagaggg aatcttagcg gtcgctcttc tttagagcag    60
ctggcagcgt ggaacgccac cgaagcggag ttcccggaca cgaccctgca tgaaatgttc   120
gagaacgaag catctcaaaa gccggataaa attgcagtcg tgtacgaaga aacctctctg   180
acctatcgcg agctgaacga acgtgccaat cgcatggcgc accagctgcg ttccgacgtt   240
tctccgaacc cgaacgaagt gatcgcgctg gttatggaca agagtgaaca catgatcgta   300
aatatcttgg ctgtgtggaa atctggtggc gcatacgtgc cgatcgatcc gagaagatcc   360
acacatggca cctttgctgc tgaagccaca taataacgag ct                     402

<210> SEQ ID NO 177
<211> LENGTH: 372
<212> TYPE: DNA
<213> ORGANISM: Artificial Sequence
<220> FEATURE:
<223> OTHER INFORMATION: Synthetic nucleotide

<400> SEQUENCE: 177
ttatgagaaa tgtttcactg cagcagaggg catcttagcg gtcgcggaca agagtgaaca    60
```

```
catgatcgta aatatcttgg ctgtgtggaa atctggtggc gcatacgtgc cgatcgatcc    120
gggctacccg aatgaccgta ttcagtatat cctcgaggac actcaggcgt tggctgttat    180
cgcagattct tgttacctgc ctcgtatcaa aggtatggcc gcgtctggta cgctgctcta    240
cccgtctgtc ctgccggcaa acccagacag caaatggtct gtgtcaaacc cgtcgccgct    300
gtctcgtagc accgacctgg cagaagagcc acacatggca cctttgctgc tgctagattt    360
gatagtgttc ta                                                        372

<210> SEQ ID NO 178
<211> LENGTH: 403
<212> TYPE: DNA
<213> ORGANISM: Artificial Sequence
<220> FEATURE:
<223> OTHER INFORMATION: Synthetic nucleotide

<400> SEQUENCE: 178
tttgtaattt gactctgatg cagcagaggg catcttagcg gtcgctcttc tcgtctggta     60
cgctgctcta cccgtctgtc ctgccggcaa acccagacag caaatggtct gtgtcaaacc    120
cgtcgccgct gtctcgtagc accgacctgg catacatcat ctacacctct ggcaccaccg    180
gccgcccgaa aggcgtgact gtggagcatc acggtgtggt gaacctgcag gtatccctga    240
gcaaagtttt tggtctgcgt gacaccgacg acgaagtcat cctgtctttt tctaactacg    300
ttttcgatca cttcgtagaa cagatgactg atgctatcct gaacgggcag aagaagagcc    360
acacaaggca cctttgctgc tgtgaaaagt caaaagattc cta                      403

<210> SEQ ID NO 179
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 179
tactgggagc aaacaattct cagcagcacc gactaatgca ggctggcagt aggtctgcgt     60
gacaccgacg acgaagtcat cctgtctttt ctaactacgt tttcgatcac ttcgtagaac    120
agatgactga tgctatcctg aacgggcaga cgctgctggt tctgaacgat ggtatgcgtg    180
gtgacaaaga acgcctgtac cgctacatcg aaaagaaccg tgtaacttat ctgtctggta    240
ctccatctgt ggtgtctatg tatgagttca gccgtttcaa agaccacctg cgccgcgtcg    300
attgcgtcgg tgaagctttc agcgagccgg tcttcgacaa aatccgtgaa cactacgaac    360
acatgaccca gcgacctgct gagtgaaaac agcagacgaa                          400

<210> SEQ ID NO 180
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 180
gtgggatgga agctcctcga cagcagaggg catcttagcg gtcgctctct accttccacg     60
gtttggttat caatggttat ggcccaactg aagttagcat cactacccat aagcgtttat    120
acccttcccc agagcgccgc atggataagt cgatcggcca gcaggtccac aactctacta    180
gctacgtact gaatgaagat atgaagcgta ccccgatcgg tgctgtgggt gagctgtacc    240
```

```
tgggcggtga aggtgttgtc cgcggttatc ataatcgtgc ggtgttaccg ccgagcgctt    300
catcccgaac ccgttccagt ctgaggaaga taaacgtgaa ggccgtaaca gaagaaccac    360
acatggcacc tttgctgctg gcaaaaagga cataataca                           399

<210> SEQ ID NO 181
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 181
ttgttggata tatagggtta caaaagaggg catcttagcg gtcgctcttc tcgatcggcc     60
agcaggtcca caactctact agctacgtac tgaatgaaga tatgaagcgt accccgatcg    120
gtgctgtggg tgagctgtac ctgggcggtg aaggtgttgt ccgcggttat cataatcgtg    180
cggatgttac cgccgagcgc ttcatcccga acccgttcca gtctgaggaa gataaacgtg    240
aaggccgtaa cagtcgcctg tacaagacgg gtgatctggt tcgctggatc ccgggtagct    300
ccggcgaagt cgaatacctg ggtcgcaatg acttccaggt taagattcgc gagaagaacc    360
acacatggca cctttgctgc tgaagtacac atcatcccca tg                       402

<210> SEQ ID NO 182
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 182
aattcactca gaataatttt cagcagcaaa ggtgccttgt gtggctctct cggcgaagtc     60
gaatacctgg gtcgcaatga cttccaggtt aagattcgcg gcctccgtat cgagctgggt    120
gaaatcgaag cgatcctgag cagctaccac ggcattaaac agagcgtagt gatcgcaaaa    180
gactgccgtg aggggcaca gaaattcctg gtcggctatt acgttgcaga cgctgccctg    240
ccgtccgcag cgatccgtcg tttcatgcag tcgcgcctcc cgggttacat ggttccgtcc    300
cgtctgatcc tggtttctaa attccctgtt actccgtccg ggaagctgga agaagagcga    360
ccgctaagat gccctctgct ggagattaat tccaactaaa t                        401

<210> SEQ ID NO 183
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 183
ctactgttcg ttcccaatta cagcagaggg catcttagcg gtcgctcttc tcgtctgatc     60
ctggtttcta aattccctgt tactccgtcc gggaagctgg acaccaaagc actgccgccg    120
gcggaggaag aaagcgaaat cgacgttgtt ccaccgcgct ccgaaattga gcgttctctc    180
tgcgacatct gggctgaact gctggaaatg cacccggaag aaatcggcat ttactctgac    240
ttcttctcct tgggcggcga cagcctgaaa tctactaagt tatccttcat gatccatgag    300
tcctttaacc gtgctgtgag cgttagcgcg ttattctgcc atcgcacagt tagaagagcc    360
acacatggca cctttgctgc tgttcccccca gttttacacc aa                      402
```

```
<210> SEQ ID NO 184
<211> LENGTH: 371
<212> TYPE: DNA
<213> ORGANISM: Artificial Sequence
<220> FEATURE:
<223> OTHER INFORMATION: Synthetic nucleotide

<400> SEQUENCE: 184
atgtgttata gaagttgttg cagcagaggg catcttagcg gtcctaagtt atccttcatg      60
atccatgagt cctttaaccg tgctgtgagc gttagcgcgt tattctgcca tcgcacagtt     120
gaagctcaaa ctcacctgat cttgaacgac gcagcagatg tacacgaaat taccccgatc     180
gattgcaacg acacccagat gatcccggtt tcccgtgcac aggaacgtct gctgttcatt     240
catgaattcg aaaacggttc taacgcttac aacattgacg cggctttcga actgccaggt     300
tctgtggacg cgagcctgct agaagagcca cacatggcac ctgtgctgct gagcagggat     360
aacacatgtc a                                                          371

<210> SEQ ID NO 185
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 185
tttcagaaac ttaaacttac cagcagaggg catcttagcg gtcgctcttc tgaagctcaa      60
actcacctga tcttgaacga cgcagcagat gtacacgaaa ttaccccgat cgattgcaac     120
gacacccaga tgatcccggt tcccgtgcaa caggaacgtc tgctgttcat tcatgaattc     180
gaaaacggtt ctaacgctta caacattgac gcggctttcg aactgccagg ttctgtggac     240
gcgagcctgc tggaacaggc ccttcgtggc aacctggcac gtcacgaagc actgcgcacc     300
ctgctggtta agatcacgc cactggtatt tacctgcaga aagtactgaa tagaagagcc      360
acacatggca cctttgctgc tgattcctat tacttcttat aa                        402

<210> SEQ ID NO 186
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 186
tatacaatct attggtaatc cagcagaggg catcttagcg gtcgctcttc taggaacgtc      60
tgctgttcat tcatgaattc gaaaacggtt ctaacgctta caacattgac gcggctttcg     120
aactgccagg ttctgtggac gcgagcctgc tggaacaggc ccttcgtggc aacctggcac     180
gtcacgaagc actgcgcacc ctgctggtta agatcacgc cactggtatt tacctgcaga      240
aagtactgag tccggacgaa gcgcaaggta tgttttctgt taatgtagat actgctaaac     300
aggttgaacg tctggatcag gaaattgctt ctctgtctca gcacgtcttc cagaagagcc     360
acacatggca cctttgctgc tggaaaggat taaagtattc ca                        402

<210> SEQ ID NO 187
<211> LENGTH: 402
<212> TYPE: DNA
<213> ORGANISM: Artificial Sequence
<220> FEATURE:
<223> OTHER INFORMATION: Synthetic nucleotide
```

<400> SEQUENCE: 187

```
ttacatgctt tcgacacata cagcaggtcg cagggtcatg tgttcgcagt gggttgaacg      60
tctggatcag gaaattgctt ctctgtctca gcacgtcttc cgcctggacg acgaactgcc    120
gtgggaggcg cgcatcctga aactggaatc tggcggtctg tacctgatct tggccttcca    180
ccacacctgc ttcgatgcat ggagcctgaa agttttcgaa caggagctgc gcgcgctgta    240
cgcagcgctt cagaaaacga aatctgcagc gaacttaccg gcattaaaag cacagtataa    300
ggaatacgct ctgtaccacc gccgccagct tagcggcgac cgcatgcgta acacagccag    360
cctgcattag tcggtgctgc tgaaagatcc tcacactata ca                       402
```

<210> SEQ ID NO 188
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 188

```
gttaatttct ggggatacgt cagcagaggg catcttagcg gtcgttcttc tgaatacgct      60
ctgtaccacc gccgccagct tagcggcgac cgcatgcgta acctgtccga tttctggtta    120
cgtaaactga tcggtctgga accactgcag ctgatcaccg atcgtccgcg tccggttcag    180
ttcaaatacg acggtgacga tctgagcatc gaactgtcca agaaagagac cgaaaacctg    240
cgcggcgttg caaaacgttg taagtcttcc ttatatgttg tactggtatc tgtttactgt    300
gtcatgctgg caagctacgc caaccagagc gatgttagcg tgggcatccc aagaagacca    360
cacatgtcac ctttgctgct gcttataaaa agcgtgagtt a                        401
```

<210> SEQ ID NO 189
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 189

```
tacctgtgat ctgcgtcgta cagcagaggg catcttagcg gtcgctcttc ttgatcaccg      60
atcgtccgcg tccggttcag ttcaaatacg acggtgacga tctgagcatc gaactgtcca    120
agaaagagac cgaaaacctg cgcggcgttg caaaacgttg taagtcttcc ttatatgttg    180
tactggtatc tgtttactgt gtcatgctgg caagctacgc caaccagagc gatgttagcg    240
tgggcatccc agtatcacac cgtacgcacc cgcagttcca gtctgttatc ggcttttcg     300
ttaacctggt cgttctgcgt gtagatatca gccagtccgc tatttgcggt tagaagagcc    360
acacatggca cctttgctgc tgtcttcatc gataaataca aa                       402
```

<210> SEQ ID NO 190
<211> LENGTH: 397
<212> TYPE: DNA
<213> ORGANISM: Artificial Sequence
<220> FEATURE:
<223> OTHER INFORMATION: Synthetic nucleotide

<400> SEQUENCE: 190

```
gaagcacctg tcttatttaa cagcagcacc gactaatgca ggctggcatg aaaacgttgt      60
aagtcttcct tatatgttct ggtatctgtt tactgtgtca tgctggcaag ctacgccacc    120
agagcgatgt tagcgtgggc atcccagtat cacaccgtac gcacccgcag ttccagtctg    180
```

```
ttatcggctt tttcgttaac ctggtcgttc tgcgtgtaga tatcagccag tccgctattt    240
gcggtttaat ccgtcgcgtc atgaaagaac tggttgacgc gcagctgcac caggatatgc    300
cgttccagga agttacgaaa ctgctgcagg tggataacga tcctagcact gcgaacacat    360
gaccctgcga cctgctgaag cctacccggg aagatca                             397

<210> SEQ ID NO 191
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 191
tcatcctatt acgatgcccg cagcagcaaa ggtgccatgt gtggctcttt atgccgttcc     60
aggaagttac gaaactgctg caggtggata acgatcctag ccgtcacccg ttggttcaga    120
acgtatttaa ctttgagtct cgcgcgaacg gtgaacacga tgcccgctct gaagacgagg    180
gctctcttgc attcaatcag taccgtccgg ttcagccggt tgacagcgtg gccaaattcg    240
atctgaacgc caccgtcacc gaactggaat ccggtctgcg tgttaatttc aactacgcga    300
ccagcttatt caataaatcc accatccagg gcttcctgca cacatatgaa agaagaggac    360
cgctaagatg ccctctgctg caataaaaag cttccaacgc                          400

<210> SEQ ID NO 192
<211> LENGTH: 400
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (395)..(395)
<223> OTHER INFORMATION: n is a, c, g, or t

<400> SEQUENCE: 192
atttataagg acgggccagc cagcagaggg catcttagcg gtcgctcttc tccagcttat     60
tcaataaatc caccatccag ggcttcctgc acacatatga ataccttctg cgtcagctgt    120
ccgaactgag cgctgaaggc atcaacgaag atacccagct gtcactggtt cgcccgactg    180
agaacgggga tctgcacctg ccactggccc agtctccgct cgcgaccact gcagaagaac    240
agaaagttgc ttccctgaac caggcttttcg aacgtgaagc cttcctggcg gcggaaaaaa    300
tcgccgttgt tcaaggggac cgcgctctgt cgtatgccga cctgaacggt cagaaaccac    360
acatggcacc tttgctgctg taccaatacg gggancgttt                          400

<210> SEQ ID NO 193
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 193
taatctgatc gatgctagga cagcaggtcg cagggtcatg tgttcgtagt gcgccgttgt     60
tcaaggggac cgcgctctgt cgtatgccga cctgaacggt caggctaatc aactggcgcg    120
ttatatccag tccgtctcct gcatcggtgc cgacgacggc atcgccctga tgctggaaaa    180
gagcatcgat actatcatct gcattctggc aatctggaaa gcaggcgccg cgtatgtgcc    240
```

```
gctggatccg acctacccac caggccgtgt acaactgatc ctggaggaaa tcaaagcgaa    300
agctgtgctg gtacactctt cccacgcctc taaatgtgaa cgtcacggtg ccactgccag    360
cctgcattag tcggtgctgc tgttaggagg attgaatcaa aa                      402
```

```
<210> SEQ ID NO 194
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 194
tagccctttt cgtatttgca tcagcagcaa aggtgccatg tgtggctctt tcctacccac     60
caggccgtgt acaactgatc ctggatgaaa tcaaagcgaa actgtgctgg tacactcttc    120
cacgcctcta aatgtgaacg tcacggtgcc aaagtcattg cagtagactc tccggctatt    180
gaaacggcag tgagccagca gtctgcagct gatctgccga ccattgctag cctgggtaat    240
ctggcatata tcatctttac tagcggcact tctggcaaac cgaaaggcgt tctggtagag    300
caaaaagccg ttctgctgct gcgcgacgcc ctgcgtgagc gttacttcga agagcgac     360 cgctaagatg ccctctgctg tagactgagt tgaacaacta                          400
```

```
<210> SEQ ID NO 195
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 195
atcattgcac ttgttgttcg cagcagcaaa ggtgccatgt gtggctcttc tatcatcttt     60
actagcggca cttctggcaa accgaaaggc gttctggtag agcaaaaagc cgttctgctg    120
ctgcgcgacg ccctgcgtga gcgttacttc ggtcgtgatt gtaccaaaca tcacggtgtt    180
ctgttcctga gcaactacgt tttcgacttc tccgtagaac agctggttct gtctgtactc    240
tcaggccaca aactgattgt cccgccggcg gagtttgtgg cggatgacga attctatcgt    300
atggcctcta cccacggtct ttcttacctg tctggcaccc cgagcctgct tagaagagcg    360
accgctaaga tgccctctgc tgaaatcagt aaaaaacctt cc                       402
```

```
<210> SEQ ID NO 196
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 196
ttattcgtgg attggtgttc cagcagaggg catcttagcg gtcgctcttc tttcgacttc     60
tccgtagaac agctggttct gtctgtactc tcaggccaca aactgattgt cccgccggcg    120
gagtttgtgg cggatgacga attctatcgt atggcctcta cccacggtct ttcttacctg    180
tctggcaccc cgagcctgct tcaaaaaatc gatctggcac gtctggatca cctgcaggtt    240
gtaaccgcgg cgggtgagga actccacgcg acccagtacg aaaaaatgcg tcgtcgtttt    300
aacggtccaa tctacaacgc ttatggtgtt accgagacaa cggtgtacaa cagaagaacc    360
acacatggca ccttttgctgc tgtaatcaga acctagaaaa at                      402
```

<210> SEQ ID NO 197
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 197

```
tgatttcacc actaagtctc agcaggtcgc agggtcatgt gttcgcagtg acggtccaat      60
ctacaacgct tatggtgtta ccgagacaac ggtgtacaac atcatcgctg aattcaccac     120
caactccatc ttcgaaaacg cattacgcga agtcctgccg ggcacccgtg cgtacgttct     180
gaacgcggcg ctgcagccgg ttccattcga cgctgtgggt gaactgtatc tggccggcga     240
tagcgtaacc cgtggttacc tgaaccagcc gttgctgacc gatcagcgtt tcatccctaa     300
cccgttctgc aaggaagaag acatcgcgat gggtcgtttc gctcgtctgt cacgccagcc     360
tgcattagtc ggtgctgctg gcacgagaaa taaaggagg                            399
```

<210> SEQ ID NO 198
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 198

```
taaagttatc atgtgctacc cagcagcaaa ggtgccatgt gtggctcttc tacaaaaccg      60
gcgacctggt tcgctctcgc ttcaaccgcc agcagcagcc gcagctggaa tacctgggcc     120
gtggcgacct gcagattaaa atgcgtggtt accgcattga aattagcgaa gtacagaacg     180
tgctgacctc ctccccgggc gtacgcgaag gtgcggttgt ggctaaatat gaaaacaacg     240
acacgtatag ccgtactgca cattccttag tcggttatta taccactgat aacgaaacag     300
tttcagaagc tgatatcctc accttcatga aagcgcgtct gccgacctat aagaagagga     360
ccgctaagat gccctctgct ggagatgaat ataggtttac a                         401
```

<210> SEQ ID NO 199
<211> LENGTH: 399
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (394)..(394)
<223> OTHER INFORMATION: n is a, c, g, or t

<400> SEQUENCE: 199

```
gttcattgca taatgcttct cagcagcacc gactaatgca ggctggagtg ttccattcga      60
cgctgtgggt gaactgtatc tggccggcga tagcgtaacc cgtggttacc tgaaccagcc     120
gttgctgacc gatcagcgtt tcataactaa cccgttctgc aaggaagaag acatcgcgat     180
gggtcgtttc gctcgtctgt acaaaaccgg cgacctggtt cgctctcgct tcaaccgcca     240
gcagcagccg cagctggaat acctgggccg tggcgacctg cagattaaaa tgcgtggtta     300
ccgcattgaa attagcgaag tacagaacgt gctgacctcc tcccgggcgc atgcgaacac     360
atgaccctgc gacctgctgc tggatgtaaa gggntttaa                            399
```

<210> SEQ ID NO 200
<211> LENGTH: 401
<212> TYPE: DNA

<213> ORGANISM: Artificial Sequence
<220> FEATURE:
<223> OTHER INFORMATION: Synthetic nucleotide

<400> SEQUENCE: 200

```
attgatatgt aagagatttc cagcagcaaa ggtgccatgt gtggctctta tcgtactgca      60
cattccttag tcggttatta taccactgat aacgaaacag tttcagaagc tgatatcctc     120
accttcatga aagcgcgtct gccgacctat atggtgcctt ctcacctgtg ctgcctggaa     180
ggtgctctgc cagtcactat taacggtaaa ctggacgttc gtcgtctgcc tgaaattatc     240
aacgacagtg cgcaatcctc atattccccg ccgcgcaaca ttatcgaagc gaaaatgtgc     300
cgtttatggg aaagcgcgct gggtatggaa cgctgcggta ttgacgatga cagaagagcg     360
accgctaaga tgccctctgc tgaacgaaaa tggtacctat t                         401
```

<210> SEQ ID NO 201
<211> LENGTH: 398
<212> TYPE: DNA
<213> ORGANISM: Artificial Sequence
<220> FEATURE:
<223> OTHER INFORMATION: Synthetic nucleotide

<400> SEQUENCE: 201

```
gattactaca tttttctcaa cagcagcacc gactaatgca ggctggcagt gaacggtaaa      60
ctggacgttc gtcgtctgcc tgaaattatc aacgacagtg cgaatcctca tattccccgc     120
cgcgcaacat tatcgaagcg aaaatgtgcg tttatgggaa agcgcgctgg gtatggaacg     180
ctgcggtatt gacgatgacc tcttcaagct ggggggggat tctatcacca gtctgcacct     240
cgtcgcacag attcacaatc aggtgggctg taagattacc gtgcgcgata ttttcgaaca     300
ccgtaccgcg cgtgctctcc acgatcacgt tttcatgaag atagcgatc atgcgaacac      360
atgaccctgc gacctgctgg cccaaccccc cccaaaag                             398
```

<210> SEQ ID NO 202
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 202

```
aattggttac ctctatcccc cagcagcaaa ggtgccatgt gtggctcttc taccgtaccg      60
cgcgtgctct ccacgatcac gttttcatga aggatagcga tcgctctaac gtcacccagt     120
tccgtaccga gcaggggccg gtcattggcg aagctccgct gctgccgatc caggattggt     180
tcttgagcaa agctctgcag cacccctatgt actggaacca cacgttctac gtacgtaccc     240
cggaactgga cgttgattcc ctgagtgcgg ccgttcgtga cctgcagcag taccacgacg     300
ttttccgcat gcgcctgaaa cgcgaagaag ttggctttgt acagtccttt gagaagagcg     360
accgctaaga tgccctctgc tgaaatcgga tcccagtatg ag                        402
```

<210> SEQ ID NO 203
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 203

```
gcataaagcg ggaggcttct cagcagaggg catcttagcg gtcgctcttc ttttccgcat      60
```

```
gcgcctgaaa cgcgaagaag ttggctttgt acagtccttt gccgaagact ttccccggc     120 gcagctgcgt gtactgaacg tgaaggacgt ggatggtagc gcggcggtta acgaaatcct    180
ggacggttgg caaagcggct tcaacctgga aaacggtccg atcggctcga tcggttatct    240
gcatggctat gaagaccgct ccgcacgtgt gtggttttct gtacaccaca tggccattga    300
cactgtttcc tggcagatcc tggttcgtga tctgcagact ctgtaccgta aagaagaacc    360
acacatggca cctttgctgc tggcactatt ctatgacaca g                        401
```

<210> SEQ ID NO 204
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 204

```
tttcgaccga tttcagtctg cagcaggtcg cagggttatg tgttcgcagt gcaacctgga     60
aaacggtccg atcggctcga tcggttatct gcatggctat gaagaccgct ccgcacgtgt    120
gtggttttct gtacaccaca tggccattga cactgtttcc tggcagatcc tggttcgtga    180
tctgcagact ctgtaccgta acggttccct gggttccaaa ggttcttcat ttcgccaatg    240
ggccgaggca atccaaaact acaaagcgag cgactcggaa cgtaaccatt ggaacaagct    300
ggttatggaa actgcatcgt cgatcagcgc gctgccgacc tccactggtt ccactaccag    360
cctgcattag tcggtgctgc tgtaattacc gtcaaaaaa                           399
```

<210> SEQ ID NO 205
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 205

```
cttcctgtgg gttttctaca gcagcaaagg tgccatgtgt ggctcttctt ccaaaactac     60
aaagcgagcg actcggaacg taaccattgg aacaagctgg ttatggaaac tgcatcgtcg    120
atcagcgcgc tgccgacctc cactggttct cgcgtacgtc tctcccgttc tctgtctcct    180
gaaaaaactg cttctctgat ccagggtggc atcgatcgtc aggatgtaag cgtatacgat    240
tctctgctga cttctgttgg cctggctttg caacacatcg cgccgactgg cccgtctatg    300
gttacaatcg agggtcacgg ccgcgaagaa gttgaccaga ccctggatga aagagcgac     360 cgctaagatg ccctctgctg aatacgcgaa tgatgtaaaa                          400
```

<210> SEQ ID NO 206
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 206

```
tttttgagct acgctttcgg cagcagcaaa ggtgccatgt gtggctcttc tacttctgtt     60
ggcctggctt tgcaacacat cgcgccgact ggcccgtcta tggttacaat cgagggtcac    120
ggccgcgaag aagttgacca gaccctggat gtttctcgta cgatgggctg gttcactacc    180
atgtatccgt tcgaaatccc gcgtctgtcg acggaaaaca tcgtgcaggg tgttgttgct    240
```

| | |
|---|---|
| gtaagtgaac gcttccgcca agttccggct cgcggtgttg gttatggtac tctgtacggt | 300 |
| tacacccagc accctctgcc gcaggttact gttaactacc tgggccagct gagaaggacc | 360 |
| gctaagatgc cctctgctgc tgaaagtaga atgtattga | 399 |

```
<210> SEQ ID NO 207
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 207
```

| | |
|---|---|
| gtcagtagta taccgttcgt cagcagaggg catcttagcg gtcgctcttc tacacccagc | 60 |
| accctctgcc gcaggttact gttaactacc tgggccagct ggctcgtaaa cagagcaagc | 120 |
| cgaaagaatg ggttctggca gttggtgata acgagttcga gtacggtctg atgacctccc | 180 |
| cggaggataa ggaccgttcg agctccgcag tggatgttac ggccgtctgc atcgacggga | 240 |
| cgatgatcat cgatgtggac tcggcttggt ctttggaaga atctgaacag ttcatctcgt | 300 |
| caattgaaga aggtctgaac aaaatcctgg acggtcgtgc atcccagcag aagaaagcca | 360 |
| cacatggcac ctttgctgct gaggaaggca atcttagatc g | 401 |

```
<210> SEQ ID NO 208
<211> LENGTH: 403
<212> TYPE: DNA
<213> ORGANISM: Artificial Sequence
<220> FEATURE:
<223> OTHER INFORMATION: Synthetic nucleotide

<400> SEQUENCE: 208
```

| | |
|---|---|
| ttctgcagaa cgttttgta acagcagcaa aggtgccatg tgtggctctt ctgctcgtaa | 60 |
| acagagcaag ccgaaagaat gggttctggc agttggtgat aacgagttcg agtacggtct | 120 |
| gatgacctcc ccggaggata aggaccgttc gagctccgca gtggatgtta cggccgtctg | 180 |
| catcgacggg acgatgatca tcgatgtgga ctcggcttgg tctttggaag aatctgaaca | 240 |
| gttcatctcg tcaattgaag aaggtctgaa caaaatcctg gacggtcgtg catcccagca | 300 |
| gactagccgc tttccggatg tgccgcagcc agcagagacc tacaccccat acagaagagt | 360 |
| gaccgctaag atgccctctg ctggatgggc cataataccg tcg | 403 |

```
<210> SEQ ID NO 209
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 209
```

| | |
|---|---|
| atcttttatg tactttgtga cagcagaggg catcttagcg gtcgctcttc tgatgtggac | 60 |
| tcggcttggt ctttggaaga atctgaacag ttcatctcgt caattgaaga aggtctgaac | 120 |
| aaaatcctgg acggtcgtgc atcccagcag actagccgct ttccggatgt gccgcagcca | 180 |
| gcagagacct acaccccata cttcgaatat ctggaaccgc cgcgccaggg cccgaccctg | 240 |
| tttctgctgc caccgggtga aggtggtgcg gaatcttact tcaacaacat cgtcaaacgc | 300 |
| ttgcgtcaaa ctaacatggt tgtctttaac aactactacc tgcactccaa aagaagagcc | 360 |
| acacatggca cctttgctgc tgacactaaa agtgttgaaa aa | 402 |

<210> SEQ ID NO 210
<211> LENGTH: 398
<212> TYPE: DNA
<213> ORGANISM: Artificial Sequence
<220> FEATURE:
<223> OTHER INFORMATION: Synthetic nucleotide

<400> SEQUENCE: 210

```
taatttcctg tgcaactcag cagcaaaggt gccatgtgtg gctcttcttt cgaatatctg      60
gaaccgccgc gccagggccc gaccctgttt ctgctgccac cgggtgaagg tggtgcggaa     120
tcttacttca acaacatcgt caaacgcttg cgtcaaacta acatggttgt ctttaacaac     180
tactacctgc actccaaacg tctgcgcacc ttcgaggaac tggctgaaat gtatctggac     240
caggtacgcg gcatccaacc gcacggtcca taccacttca tcggctggag cttcggggc     300
attctggcga tggagatgtc ccgtcgtctg gttgcgagcg acgaaaaaga agagcgaccg     360
ctaagatgcc ctctgctgac ccaaagaaat aaacaaga                            398
```

<210> SEQ ID NO 211
<211> LENGTH: 379
<212> TYPE: DNA
<213> ORGANISM: Artificial Sequence
<220> FEATURE:
<223> OTHER INFORMATION: Synthetic nucleotide

<400> SEQUENCE: 211

```
atgtatcctc gctctttaac cagcatcacc gactaatgca ggctggcagt ggcattctgg      60
cgatggagat gtcccgtcgt ctggttgcga gcgacgaaaa attggtttct gggtattatc     120
gacacctatt tcaacgtacg tggtgccact cgcaccattg gccttggtga tactgaaatc     180
ctggatccga tccaccacat ctataacccg gaccggcaa actttcagcg tctgccgtct     240
gccaccgacc gtatcgtcct gtttaaggcc atgcgtccga ataataaata tgaatcagaa     300
accagcgtcg cctgtatgag tactacgaca ctgcgaacac atgaccctgc gacctgctga     360
gtaataatca aaccgggtg                                                  379
```

<210> SEQ ID NO 212
<211> LENGTH: 392
<212> TYPE: DNA
<213> ORGANISM: Artificial Sequence
<220> FEATURE:
<223> OTHER INFORMATION: Synthetic nucleotide

<400> SEQUENCE: 212

```
ctaacgcatt gtcaggtttc cagcagcacc gactaatgca ggctggcagt gcgtatcgtc      60
ctgtttaagg ccatgcgtcc gaataataaa tatgaatcag aaaaccagcg tcgccctacg     120
acgcgttaga ttccacggac tggaccgcat gttaccaggc gatccctacc tcctcatggt     180
cgcgcctgcg cacgatccac accttcccgg gttcggaaat ccacaaccgc tggtcccgtt     240
gcgttcgtct gagccgtaac accagccttg ccatcgaccc gtctctggca gctcagtaca     300
tcggtcgttg gaagtaagca gagtaaagac cgtgcactta tcactggaac acatgaccct     360
gcgacctgct gttctacact ggtatccgga gt                                  392
```

<210> SEQ ID NO 213
<211> LENGTH: 298
<212> TYPE: DNA
<213> ORGANISM: Artificial Sequence
<220> FEATURE:
<223> OTHER INFORMATION: Synthetic nucleotide -continued

<400> SEQUENCE: 213

```
atgacccaat tgaagccgcc taacgggacc actccgatcg gcttcagcgc cactactagc    60
ctgaacgcta gcggctcttc ctcggttaag aatggtacca tcaagccttc gaatggtatc   120
ttcaaacctt ctactcgtga caccatggac ccgtgctcgg caacgccgc tgacggctcc    180 attcgcgtac gttttcgcgg tggcatcgaa cgttggaaag agtgtgtaaa ccaagtgccg    240
gagcgttgcg acctgtctgg tctgaccacg gacagcaccc gctaccagct ggcttcga     298
```

<210> SEQ ID NO 214
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 214

```
ctgtctggtc tgaccacgga cagcacccgc taccagctgg cttcgaccgg cttcggcgac    60
gcgagcgcgg cttaccagga acgtctgatg actgtgccgg tagatgttca tgctgcgctc   120
caggagctgt gcctggaacg ccgcgtctct gtgggttctg tgatcaactt cagcgttcac   180
cagatgctga agggttttgg caacggtact cacactatca ccgcgagcct gcaccgcgaa   240
cagaatctgc agaactcctc tccgtcttgg gtcgtttccc ctactatcgt gacccatg     298
```

<210> SEQ ID NO 215
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 215

```
aacggtactc acactatcac cgcgagcctg caccgcgaac agaatctgca gaactcctct    60
ccgtcttggg tcgtttcccc tactatcgtg acccatgaaa accgcgatgg ctggtcagtg   120
gcgcaggcag tggagtctat cgaggctggt cgtggctccg aaaaggaatc tgtgaccgcg   180
attgattccg ctcctccct ggtcaaaatg ggtctgttcg atctgctggt ttccttcgtc    240
gatgcggatg acgcgcgtat cccttgcttc gactttccgc tggctgttat tgtgcgc      297
```

<210> SEQ ID NO 216
<211> LENGTH: 166
<212> TYPE: DNA
<213> ORGANISM: Artificial Sequence
<220> FEATURE:
<223> OTHER INFORMATION: Synthetic nucleotide

<400> SEQUENCE: 216

```
tgacgcgcgt atcccttgct tcgactttcc gctggctgtt attgtgcgcg agtgcgatgc    60
aaacctgtct ctcacccttc gcttctcgga ctgcctgttc aacgaggaaa ccatttgtaa   120
tttcacggat gccctcaata tcctgttggc tgaggcagtt atcggt                  166
```

<210> SEQ ID NO 217
<211> LENGTH: 178
<212> TYPE: DNA
<213> ORGANISM: Artificial Sequence
<220> FEATURE:
<223> OTHER INFORMATION: Synthetic nucleotide

<400> SEQUENCE: 217

```
acgaggaaac catttgtaat ttcacggatg ccctcaatat cctgttggct gaggcagtta    60
```

```
tcggtcgtgt aactccggta gccgatatcg agctgctgtc tgcagagcag aaacaacagc    120
tggaggaatg gaacaacacc gatggtgaat atccgtctag caagcgtctg caccacct     178
```

<210> SEQ ID NO 218
<211> LENGTH: 98
<212> TYPE: DNA
<213> ORGANISM: Artificial Sequence
<220> FEATURE:
<223> OTHER INFORMATION: Synthetic nucleotide

<400> SEQUENCE: 218

```
gtgaatatcc gtctagcaag cgtctgcacc acctgattga agaggtggtg aacgtcacg    60 aagacaaaat cgctgtggtg tgcgacgaac gtgaactg                           98
```

<210> SEQ ID NO 219
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 219

```
tcacgaagac aaaatcgctg tggtgtgcga cgaacgtgaa ctgacttacg gtgaactcaa    60
tgcccagggc aactccctgg cgcgttacct gcgcagcatt ggtattctgc ctgaacagct   120
ggttgcgctg tttctggaca aatccgaaaa attgatcgta accatcctgg gcgtctggaa   180
atccggtgct gcttacgtgc caattgaccc gacctaccct gacgaacgtg ttcgtttcgt   240
tctggacgac acgaaagccc gtgcgattat cgcttccaat cagcatgttg aacgcct      297
```

<210> SEQ ID NO 220
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 220

```
tgatcgtaac catcctgggc gtctggaaat ccggtgctgc ttacgtgcca attgacccga    60
cctaccctga cgaacgtgtt cgtttcgttc tggacgacac gaaagcccgt gcgattatcg   120
cttccaatca gcatgttgaa cgcctccagc gtgaagtaat cggtgatcgc aacctgtgca   180
tcatccgtct cgaaccactg ctggcgagcc ttgcgcagga ttcttctaaa ttccctgccc   240
acaacctgga tgatttgccg ctgaccagcc agcagctggc gtacgttact tatacca      297
```

<210> SEQ ID NO 221
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 221

```
agcgtgaagt aatcggtgat cgcaacctgt gcatcatccg tctcgaacca ctgctggcga    60
gccttgcgca ggattcttct aaattccctg cccacaacct ggatgatttg ccgctgacca   120
gccagcagct ggcgtacgtt acttatacca gcggtaccac cggctttccg aaaggcattt   180
tcaaacagca cactaacgtt gttaactcca tcacagacct gtccgctcgt tacggtgttg   240
caggtcaaca ccatgaagct atcctgctct tcagtgcttg cgttttcgaa ccgttcg      297
```

<210> SEQ ID NO 222
<211> LENGTH: 281
<212> TYPE: DNA
<213> ORGANISM: Artificial Sequence
<220> FEATURE:
<223> OTHER INFORMATION: Synthetic nucleotide

<400> SEQUENCE: 222

```
gttaactcca tcacagacct gtccgctcgt tacggtgttg caggtcaaca ccatgaagct    60
atcctgctct tcagtgcttg cgttttcgaa ccgttcgttc gtcagactct gatggccctg   120
gtgaacggtc acctgctcgc cgtgattaac gatgtagaaa aatatgacgc tgacaccctc   180
ctcccattta tccgccgtca ctctatcacc tatctgaacg gtactgcgtc ggttctccaa   240
gagtatgact ctctgactg tccgagcctg aaccgtatca t                       281
```

<210> SEQ ID NO 223
<211> LENGTH: 295
<212> TYPE: DNA
<213> ORGANISM: Artificial Sequence
<220> FEATURE:
<223> OTHER INFORMATION: Synthetic nucleotide

<400> SEQUENCE: 223

```
ctatcaccta tctgaacggt actgcgtcgg ttctccaaga gtatgacttc tctgactgtc    60
cgagcctgaa ccgtatcatc ctggtgggcg agaacctgac cgaagcacgt tacctggcac   120
tgcgtcagcg tttcaaaaat cgtattctga acgagtacgg tttcaccgag tctgcgttcg   180
tgactgcgct gaaaattttc gatccggaaa gcacccgcaa agatacctcc ctggggcgtc   240
cggtgcgcaa tgttaaatgc tatatcttga accctagcct gaaacgcgtg ccaat       295
```

<210> SEQ ID NO 224
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 224

```
acgagtacgg tttcaccgag tctgcgttcg tgactgcgct gaaaattttc gatccggaaa    60
gcacccgcaa agatacctcc ctggggcgtc cggtgcgcaa tgttaaatgc tatatcttga   120
accctagcct gaaacgcgtg ccaattggtg ctacaggtga gctgcatatt ggcggcctgg   180
gtatctccaa gggttacttg aatcgtccgg aactgacgcc gcaccgcttc atcccgaacc   240
cgtttcagac cgattgcgaa aaacagctgg gtatcaactc tctgatgtac aaaaccg     297
```

<210> SEQ ID NO 225
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 225

```
atcgtccgga actgacgccg caccgcttca tcccgaaccc gtttcagacc gattgcgaaa    60
aacagctggg tatcaactct ctgatgtaca aaaccggtga tctggctcgc tggctcccga   120
acggtgaagt tgaatacctg gccgtgcgcg atttccagat caaactgcgc ggtattcgta   180
ttgagccggg cgaaatcgag actatgctgg cgatgtatcc gcgcgttcgt acctccctgg   240
tggtttccaa gaaattacgt aacggtcctg aagaaacaac gaacgaacac ctggtag     297
```

<210> SEQ ID NO 226
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 226

```
cggatttcca gatcaaactg cgcggtattc gtattgagcc gggcgaaatc gagactatgc    60
tggcgatgta tccgcgcgtt cgtacctccc tggtggtttc caagaaatta cgtaacggtc   120
ctgaagaaac aacgaacgaa cacctggtag gctactacgt atgcgactcc gcatctgttt   180
ccgaagcgga tctgctgtcc ttcctggaga agaagctgcc gcgttatatg attccgactc   240
gtctggtaca gctgagccag atcccggtta acgtcaacgg taaagccgat ctgcgtg      297
```

<210> SEQ ID NO 227
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 227

```
ttcctggaga agaagctgcc gcgttatatg attccgactc gtctggtaca gctgagccag    60
atcccggtta acgtcaacgg taaagccgat ctgcgtgctc tgccggcggt tgatatctcc   120
aacagcaccg aagttcgttc tgatctgcgt ggtgataccg aaattgccct cggcgaaatc   180
tgggcggacg tgctgggcgc cgtcagcgt tcggttagcc gtaacgataa cttttttccgc   240
ctcggtggcc actctatcac ctgcatccag ctgattgcgc gtatccgtca gcgtcagc     298
```

<210> SEQ ID NO 228
<211> LENGTH: 307
<212> TYPE: DNA
<213> ORGANISM: Artificial Sequence
<220> FEATURE:
<223> OTHER INFORMATION: Synthetic nucleotide

<400> SEQUENCE: 228

```
acctgcatcc agctgattgc gcgtatccgt cagcgtcagc gtttgtctgt gtctatctct    60
gtggaagacg tgtttgctac acgcactctt gagcgtatgg ccgacctgtt gcaaaacaaa   120
cagcaagaga aatgcgacaa accacacgaa gcaccgactg aactgcttga agaaaacgct   180
gcgactgata acatctacct ggcgaacagc ctgcagcaag gttcgtcta ccattacctg    240
aaaagcatgg aacaaagtga tgcttatgta atgcagagcg ttctgcgtta caacaccacc   300
ctttccc                                                             307
```

<210> SEQ ID NO 229
<211> LENGTH: 159
<212> TYPE: DNA
<213> ORGANISM: Artificial Sequence
<220> FEATURE:
<223> OTHER INFORMATION: Synthetic nucleotide

<400> SEQUENCE: 229

```
catggaacaa agtgatgctt atgtaatgca gagcgttctg cgttacaaca ccaccctttc    60
cccggatctg ttccagcgtg cctggaaaca cgcgcagcaa agcttcccgg ctctgcgtct   120
gcgcttctct tgggaaaaag aagtcttcca gctgctgga                          159
```

```
<210> SEQ ID NO 230
<211> LENGTH: 150
<212> TYPE: DNA
<213> ORGANISM: Artificial Sequence
<220> FEATURE:
<223> OTHER INFORMATION: Synthetic nucleotide

<400> SEQUENCE: 230
aaagcttccc ggctctgcgt ctgcgcttct cttgggaaaa agaagtcttc cagctgctgg      60
atcaggaccc gcctctggac tggcgtttcc tctacttcac tgatgtggcg gctggtgcag     120
tagaagaccg taaactggaa gatttacgcc                                      150

<210> SEQ ID NO 231
<211> LENGTH: 188
<212> TYPE: DNA
<213> ORGANISM: Artificial Sequence
<220> FEATURE:
<223> OTHER INFORMATION: Synthetic nucleotide

<400> SEQUENCE: 231
ctggtgcagt agaagaccgt aaactggaag atttacgccg ccaggacctc accgagcgtt      60
ttaaactgga tgtgggccgt ctgtttcgcg tttacctgat caaacacagc gaaaaccgtt     120
tcacttgtct gttctcttgt caccacgcta tcctggacgg ctggtcctta ccgcttctgt     180
tcgaaaaa                                                              188

<210> SEQ ID NO 232
<211> LENGTH: 300
<212> TYPE: DNA
<213> ORGANISM: Artificial Sequence
<220> FEATURE:
<223> OTHER INFORMATION: Synthetic nucleotide

<400> SEQUENCE: 232
cgtttacctg atcaaacaca gcgaaaaccg tttcacttgt ctgttctctt gtcaccacgc      60
tatcctggac ggctggtcct taccgcttct gttcgaaaaa gtacacgaaa catacctgca     120
actgctgcac ggcgataacc tgacctcctc tatggatgat ccatacaccc gtacccaacg     180
ctacctgcat gcgcaccgcg aagatcacct cgacttttgg gctggcgtgg tgcagaaaat     240
caacgaacgt tgcgatatga atgctctgtt aaacgaacgc agccgctata aagtgcagct     300

<210> SEQ ID NO 233
<211> LENGTH: 240
<212> TYPE: DNA
<213> ORGANISM: Artificial Sequence
<220> FEATURE:
<223> OTHER INFORMATION: Synthetic nucleotide

<400> SEQUENCE: 233
tgctctgtta aacgaacgca gccgctataa agtgcagctg gccgactacg atcaggtaca      60
ggaacagcgt cagctgacga tcgctctgag cggtgacgcg tggctggcgg atctgcgcca     120
gacatgcagt gcgcagggca tcacgctgca ctctatcctg caatttgtat ggcatgcagt     180
tctgcatgcc tacggtggcg gtactcacac tatcactggc accactattt ctggtcgcaa     240

<210> SEQ ID NO 234
<211> LENGTH: 282
<212> TYPE: DNA
<213> ORGANISM: Artificial Sequence
<220> FEATURE:
<223> OTHER INFORMATION: Synthetic nucleotide
```

<400> SEQUENCE: 234

| | | |
|---|---|---|
| acggtggcgg tactcacact atcactggca ccactatttc tggtcgcaac ctcccgatcc | 60 |
| tgggtatcga gcgtgcggta ggcccgtaca ttaacaccct gccgttagtg ttggaccatt | 120 |
| ctactttaa agacaagacg atcatggaag ctattgaaga cgtccaagcg aaggtgaatg | 180 |
| ttatgaactc ccgtggtaat gtagaactgg gtcgcctgca caaaaccgac ctgaaacatg | 240 |
| gcctgttcga ttctctgttt gtgctggaaa actatccaaa cc | 282 |

<210> SEQ ID NO 235
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 235

| | | |
|---|---|---|
| gctattgaag acgtccaagc gaaggtgaat gttatgaact cccgtggtaa tgtagaactg | 60 |
| ggtcgcctgc acaaaaccga cctgaaacat ggcctgttcg attctctgtt tgtgctggaa | 120 |
| aactatccaa acctggataa atcccgtact ctggagcacc aaactgaact gggttactcc | 180 |
| atcgagggtg gtaccgaaaa actgaactat ccgctggcgg tgattgctcg tgaggttgag | 240 |
| accactggcg gctttactgt tagcatctgc tatgcgagcg aactgtttga agaggtga | 298 |

<210> SEQ ID NO 236
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 236

| | | |
|---|---|---|
| aactgaacta tccgctggcg gtgattgctc gtgaggttga gaccactggc ggctttactg | 60 |
| ttagcatctg ctatgcgagc gaactgtttg aagaggtgat gatcagcgag cttctccata | 120 |
| tggtacagga taccctgatg caggttgcac gcgggctcaa cgaacctgtg gctccctgg | 180 |
| aatacctgtc ttccatccag ttagagcagc tggcagcgtg aacgccacc gaagcggagt | 240 |
| tcccggacac gaccctgcat gaaatgttcg agaacgaagc atctcaaaag ccggataa | 298 |

<210> SEQ ID NO 237
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 237

| | | |
|---|---|---|
| ttagagcagc tggcagcgtg aacgccacc gaagcggagt tcccggacac gaccctgcat | 60 |
| gaaatgttcg agaacgaagc atctcaaaag ccggataaa ttgcagtcgt gtacgaagaa | 120 |
| acctctctga cctatcgcga gctgaacgaa cgtgccaatc gcatggcgca ccagctgcgt | 180 |
| tccgacgttt ctccgaaccc gaacgaagtg atcgcgctgg ttatggacaa gagtgaacac | 240 |
| atgatcgtaa atatcttggc tgtgtggaaa tctggtggcg catacgtgcc gatcgatc | 298 |

<210> SEQ ID NO 238
<211> LENGTH: 268
<212> TYPE: DNA
<213> ORGANISM: Artificial Sequence
<220> FEATURE:

<223> OTHER INFORMATION: Synthetic nucleotide

<400> SEQUENCE: 238

| gagtgaacac atgatcgtaa atatcttggc tgtgtggaaa tctggtggcg catacgtgcc | 60 |
| gatcgatccg ggctacccga atgaccgtat tcagtatatc ctcgaggaca ctcaggcgtt | 120 |
| ggctgttatc gcagattctt gttacctgcc tcgtatcaaa ggtatggccg cgtctggtac | 180 |
| gctgctctac ccgtctgtcc tgccggcaaa cccagacagc aaatggtctg tgtcaaaccc | 240 |
| gtcgccgctg tctcgtagca ccgacctg | 268 |

<210> SEQ ID NO 239
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 239

| cgtctggtac gctgctctac ccgtctgtcc tgccggcaaa cccagacagc aaatggtctg | 60 |
| tgtcaaaccc gtcgccgctg tctcgtagca ccgacctggc atacatcatc tacacctctg | 120 |
| gcaccaccgg ccgcccgaaa ggcgtgactg tggagcatca cggtgtggtg aacctgcagg | 180 |
| tatccctgag caaagttttt ggtctgcgtg acaccgacga cgaagtcatc ctgtcttttt | 240 |
| ctaactacgt tttcgatcac ttcgtagaac agatgactga tgctatcctg aacgggc | 297 |

<210> SEQ ID NO 240
<211> LENGTH: 260
<212> TYPE: DNA
<213> ORGANISM: Artificial Sequence
<220> FEATURE:
<223> OTHER INFORMATION: Synthetic nucleotide

<400> SEQUENCE: 240

| ctaactacgt tttcgatcac ttcgtagaac agatgactga tgctatcctg aacgggcaga | 60 |
| cgctgctggt tctgaacgat ggtatgcgtg gtgacaaaga acgcctgtac cgctacatcg | 120 |
| aaaagaaccg tgtaacttat ctgtctggta ctccatctgt ggtgtctatg tatgagttca | 180 |
| gccgtttcaa agaccacctg cgccgcgtcg attgcgtcgg tgaagctttc agcgagccgg | 240 |
| tcttcgacaa aatccgtgaa | 260 |

<210> SEQ ID NO 241
<211> LENGTH: 192
<212> TYPE: DNA
<213> ORGANISM: Artificial Sequence
<220> FEATURE:
<223> OTHER INFORMATION: Synthetic nucleotide

<400> SEQUENCE: 241

| accttccacg gtttggttat caatggttat ggcccaactg aagttagcat cactacccat | 60 |
| aagcgtttat accctttccc agagcgccgc atggataagt cgatcggcca gcaggtccac | 120 |
| aactctacta gctacgtact gaatgaagat atgaagcgta ccccgatcgg tgctgtgggt | 180 |
| gagctgtacc tg | 192 |

<210> SEQ ID NO 242
<211> LENGTH: 259
<212> TYPE: DNA
<213> ORGANISM: Artificial Sequence
<220> FEATURE:
<223> OTHER INFORMATION: Synthetic nucleotide

<400> SEQUENCE: 242

```
tgaatgaaga tatgaagcgt accccgatcg gtgctgtggg tgagctgtac ctgggcggtg    60
aaggtgttgt ccgcggttat cataatcgtg cggatgttac cgccgagcgc ttcatcccga   120
acccgttcca gtctgaggaa gataaacgtg aaggccgtaa cagtcgcctg tacaagacgg   180
gtgatctggt tcgctggatc ccgggtagct ccggcgaagt cgaatacctg ggtcgcaatg   240
acttccaggt taagattcg                                                259
```

<210> SEQ ID NO 243
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 243

```
cgaagtcgaa tacctgggtc gcaatgactt ccaggttaag attcgcggcc tccgtatcga    60
gctgggtgaa atcgaagcga tcctgagcag ctaccacggc attaaacaga gcgtagtgat   120
cgcaaaagac tgccgtgagg gggcacagaa attcctggtc ggctattacg ttgcagacgc   180
tgccctgccg tccgcagcga tccgtcgttt catgcagtcg cgcctcccgg ttacatggt    240 tccgtcccgt ctgatcctgg tttctaaatt ccctgttact ccgtccggga agctgga     297
```

<210> SEQ ID NO 244
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 244

```
cgtctgatcc tggttttctaa attccctgtt actccgtccg ggaagctgga caccaaagca    60
ctgccgccgg cggaggaaga aagcgaaatc gacgttgttc caccgcgctc cgaaattgag   120
cgttctctct gcgacatctg ggctgaactg ctggaaatgc acccggaaga aatcggcatt   180
tactctgact tcttctcctt gggcggcgac agcctgaaat ctactaagtt atccttcatg   240
atccatgagt cctttaaccg tgctgtgagc gttagcgcgt tattctgcca tcgcaca     297
```

<210> SEQ ID NO 245
<211> LENGTH: 150
<212> TYPE: DNA
<213> ORGANISM: Artificial Sequence
<220> FEATURE:
<223> OTHER INFORMATION: Synthetic nucleotide

<400> SEQUENCE: 245

```
tccttcatga tccatgagtc ctttaaccgt gctgtgagcg ttagcgcgtt attctgccat    60
cgcacagttg aagctcaaac tcacctgatc ttgaacgacg cagcagatgt acacgaaatt   120
accccgatcg attgcaacga cacccagatg                                   150
```

<210> SEQ ID NO 246
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 246

```
gaagctcaaa ctcacctgat cttgaacgac gcagcagatg tacacgaaat taccccgatc      60
gattgcaacg acacccagat gatcccggtt tcccgtgcac aggaacgtct gctgttcatt     120
catgaattcg aaaacggttc taacgcttac aacattgacg cggctttcga actgccaggt     180
tctgtggacg cgagcctgct ggaacaggcc cttcgtggca acctggcacg tcacgaagca     240
ctgcgcaccc tgctggttaa agatcacgcc actggtattt acctgcagaa agtactg        297
```

```
<210> SEQ ID NO 247
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 247
```

```
aggaacgtct gctgttcatt catgaattcg aaaacggttc taacgcttac aacattgacg      60
cggctttcga actgccaggt tctgtggacg cgagcctgct ggaacaggcc cttcgtggca     120
acctggcacg tcacgaagca ctgcgcaccc tgctggttaa agatcacgcc actggtattt     180
acctgcagaa agtactgagt ccggacgaag cgcaaggtat gttttctgtt aatgtagata     240
ctgctaaaca ggttgaacgt ctggatcagg aaattgcttc tctgtctcag cacgtct       297
```

```
<210> SEQ ID NO 248
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 248
```

```
ttgaacgtct ggatcaggaa attgcttctc tgtctcagca cgtcttccgc ctggacgacg      60
aactgccgtg ggaggcgcgc atcctgaaac tggaatctgg cggtctgtac ctgatcttgg     120
ccttccacca cacctgcttc gatgcatgga gcctgaaagt tttcgaacag gagctgcgcg     180
cgctgtacgc agcgcttcag aaaacgaaat ctgcagcgaa cttaccggca ttaaaagcac     240
agtataagga atacgctctg taccaccgcc gccagcttag cggcgaccgc atgcgtaa      298
```

```
<210> SEQ ID NO 249
<211> LENGTH: 295
<212> TYPE: DNA
<213> ORGANISM: Artificial Sequence
<220> FEATURE:
<223> OTHER INFORMATION: Synthetic nucleotide

<400> SEQUENCE: 249
```

```
aatacgctct gtaccaccgc cgccagctta gcggcgaccg catgcgtaac ctgtccgatt      60
tctggttacg taaactgatc ggtctggaac cactgcagct gatcaccgat cgtccgcgtc     120
cggttcagtt caaatacgac ggtgacgatc tgagcatcga actgtccaag aaagagaccg     180
aaaacctgcg cggcgttgca aaacgttgta agtcttcctt atatgttgta ctggtatctg     240
tttactgtgt catgctggca agctacgcca accagagcga tgttagcgtg ggcat         295
```

```
<210> SEQ ID NO 250
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 250
```

```
tgatcaccga tcgtccgcgt ccggttcagt tcaaatacga cggtgacgat ctgagcatcg      60
aactgtccaa gaaagagacc gaaaacctgc gcggcgttgc aaaacgttgt aagtcttcct     120
tatatgttgt actggtatct gtttactgtg tcatgctggc aagctacgcc aaccagagcg     180
atgttagcgt gggcatccca gtatcacacc gtacgcaccc gcagttccag tctgttatcg     240 gcttttcgt taacctggtc gttctgcgtg tagatatcag ccagtccgct atttgcg         297
```

<210> SEQ ID NO 251
<211> LENGTH: 127
<212> TYPE: DNA
<213> ORGANISM: Artificial Sequence
<220> FEATURE:
<223> OTHER INFORMATION: Synthetic nucleotide

<400> SEQUENCE: 251

```
ggtcgttctg cgtgtagata tcagccagtc cgctatttgc ggtttaatcc gtcgcgtcat      60
gaaagaactg gttgacgcgc agctgcacca ggatatgccg ttccaggaag ttacgaaact     120
gctgcag                                                               127
```

<210> SEQ ID NO 252
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 252

```
gccgttccag gaagttacga aactgctgca ggtggataac gatcctagcc gtcacccgtt      60
ggttcagaac gtatttaact ttgagtctcg cgcgaacggt gaacacgatg cccgctctga     120
agacgagggc tctcttgcat tcaatcagta ccgtccggtt cagccggttg acagcgtggc     180
caaattcgat ctgaacgcca ccgtcaccga actggaatcc ggtctgcgtg ttaatttcaa     240
ctacgcgacc agcttattca ataaatccac catccagggc ttcctgcaca catatgaa      298
```

<210> SEQ ID NO 253
<211> LENGTH: 296
<212> TYPE: DNA
<213> ORGANISM: Artificial Sequence
<220> FEATURE:
<223> OTHER INFORMATION: Synthetic nucleotide

<400> SEQUENCE: 253

```
ccagcttatt caataaatcc accatccagg cttcctgca cacatatgaa taccttctgc       60
gtcagctgtc cgaactgagc gctgaaggca tcaacgaaga tacccagctg tcactggttc     120
gcccgactga gaacggggat ctgcacctgc cactggccca gtctccgctc gcgaccactg     180
cagaagaaca gaaagttgct tccctgaacc aggctttcga acgtgaagcc ttcctggcgg     240
cggaaaaaat cgccgttgtt caaggggacc gcgctctgtc gtatgccgac ctgaac         296
```

<210> SEQ ID NO 254
<211> LENGTH: 299
<212> TYPE: DNA
<213> ORGANISM: Artificial Sequence
<220> FEATURE:
<223> OTHER INFORMATION: Synthetic nucleotide

<400> SEQUENCE: 254

```
gccgttgttc aaggggaccg cgctctgtcg tatgccgacc tgaacggtca ggctaatcaa      60
```

-continued

```
ctggcgcgtt atatccagtc cgtctcctgc atcggtgccg acgacggcat cgccctgatg    120
ctggaaaaga gcatcgatac tatcatctgc attctggcaa tctggaaagc aggcgccgcg    180
tatgtgccgc tggatccgac ctacccacca ggccgtgtac aactgatcct ggaggaaatc    240
aaagcgaaag ctgtgctggt acactcttcc cacgcctcta atgtgaacg tcacggtgc      299
```

<210> SEQ ID NO 255
<211> LENGTH: 225
<212> TYPE: DNA
<213> ORGANISM: Artificial Sequence
<220> FEATURE:
<223> OTHER INFORMATION: Synthetic nucleotide

<400> SEQUENCE: 255

```
cctctaaatg tgaacgtcac ggtgccaaag tcattgcagt agactctccg gctattgaaa    60
cggcagtgag ccagcagtct gcagctgatc tgccgaccat tgctagcctg ggtaatctgg   120
catatatcat ctttactagc ggcacttctg gcaaaccgaa aggcgttctg gtagagcaaa   180
aagccgttct gctgctgcgc gacgccctgc gtgagcgtta cttcg                    225
```

<210> SEQ ID NO 256
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 256

```
atctttacta gcggcacttc tggcaaaccg aaaggcgttc tggtagagca aaaagccgtt    60
ctgctgctgc gcgacgccct gcgtgagcgt tacttcggtc gtgattgtac caaacatcac   120
ggtgttctgt tcctgagcaa ctacgttttc gacttctccg tagaacagct ggttctgtct   180
gtactctcag gccacaaact gattgtcccg ccggcggagt ttgtggcgga tgacgaattc   240
tatcgtatgg cctctaccca cggtctttct tacctgtctg gcaccccgag cctgctt      297
```

<210> SEQ ID NO 257
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 257

```
ttcgacttct ccgtagaaca gctggttctg tctgtactct caggccacaa actgattgtc    60
ccgccggcgg agtttgtggc ggatgacgaa ttctatcgta tggcctctac ccacggtctt   120
tcttacctgt ctggcacccc gagcctgctt caaaaaatcg atctggcacg tctggatcac   180
ctgcaggttg taaccgcggc gggtgaggaa ctccacgcga cccagtacga aaaaatgcgt   240
cgtcgtttta acggtccaat ctacaacgct tatggtgtta ccgagacaac ggtgtac      297
```

<210> SEQ ID NO 258
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 258

```
ggtccaatct acaacgctta tggtgttacc gagacaacgg tgtacaacat catcgctgaa    60
ttcaccacca actccatctt cgaaaacgca ttacgcgaag tcctgccggg cacccgtgcg   120
```

```
tacgttctga acgcggcgct gcagccggtt ccattcgacg ctgtgggtga actgtatctg    180
gccggcgata gcgtaacccg tggttacctg aaccagccgt tgctgaccga tcagcgtttc    240
atccctaacc cgttctgcaa ggaagaagac atcgcgatgg gtcgtttcgc tcgtctgt     298
```

<210> SEQ ID NO 259
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 259

```
aaaccggcga cctggttcgc tctcgcttca accgccagca gcagccgcag ctggaatacc    60
tgggccgtgg cgacctgcag attaaaatgc gtggttaccg cattgaaatt agcgaagtac   120
agaacgtgct gacctcctcc ccgggcgtac gcgaaggtgc ggttgtggct aaatatgaaa   180
acaacgacac gtatagccgt actgcacatt ccttagtcgg ttattatacc actgataacg   240
aaacagtttc agaagctgat atcctcacct tcatgaaagc gcgtctgccg acctata      297
```

<210> SEQ ID NO 260
<211> LENGTH: 104
<212> TYPE: DNA
<213> ORGANISM: Artificial Sequence
<220> FEATURE:
<223> OTHER INFORMATION: Synthetic nucleotide

<400> SEQUENCE: 260

```
ctaacccgtt ctgcaaggaa gaagacatcg cgatgggtcg tttcgctcgt ctgtacaaaa    60
ccggcgacct ggttcgctct cgcttcaacc gccagcagca gccg                    104
```

<210> SEQ ID NO 261
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 261

```
tactgcacat tccttagtcg gttattatac cactgataac gaaacagttt cagaagctga    60
tatcctcacc ttcatgaaag cgcgtctgcc gacctatatg gtgccttctc acctgtgctg   120
cctggaaggt gctctgccag tcactattaa cggtaaactg gacgttcgtc gtctgcctga   180
aattatcaac gacagtgcgc aatcctcata ttccccgccg cgcaacatta tcgaagcgaa   240
aatgtgccgt ttatgggaaa gcgcgctggg tatggaacgc tgcggtattg acgatgac    298
```

<210> SEQ ID NO 262
<211> LENGTH: 198
<212> TYPE: DNA
<213> ORGANISM: Artificial Sequence
<220> FEATURE:
<223> OTHER INFORMATION: Synthetic nucleotide

<400> SEQUENCE: 262

```
cgtttatggg aaagcgcgct gggtatggaa cgctgcggta ttgacgatga cctcttcaag    60
ctgggggggg attctatcac cagtctgcac ctcgtcgcac agattcacaa tcaggtgggc   120
tgtaagatta ccgtgcgcga tattttcgaa caccgtaccg cgcgtgctct ccacgatcac   180
gttttcatga aggatagc                                                 198
```

<210> SEQ ID NO 263
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 263

```
gtaccgcgcg tgctctccac gatcacgttt tcatgaagga tagcgatcgc tctaacgtca    60
cccagttccg taccgagcag gggccggtca ttggcgaagc tccgctgctg ccgatccagg   120
attggttctt gagcaaagct ctgcagcacc ctatgtactg gaaccacacg ttctacgtac   180
gtaccccgga actggacgtt gattccctga gtgcggccgt tcgtgacctg cagcagtacc   240
acgacgtttt ccgcatgcgc ctgaaacgcg aagaagttgg ctttgtacag tcctttg      297
```

<210> SEQ ID NO 264
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 264

```
tttccgcatg cgcctgaaac gcgaagaagt tggctttgta cagtcctttg ccgaagactt    60
ttccccggcg cagctgcgtg tactgaacgt gaaggacgtg gatggtagcg cggcggttaa   120
cgaaatcctg gacggttggc aaagcggctt caacctggaa aacggtccga tcggctcgat   180
cggttatctg catggctatg aagaccgctc cgcacgtgtg tggttttctg tacaccacat   240
ggccattgac actgtttcct ggcagatcct ggttcgtgat ctgcagactc tgtaccgt     298
```

<210> SEQ ID NO 265
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 265

```
acctggaaaa cggtccgatc ggctcgatcg gttatctgca tggctatgaa gaccgctccg    60
cacgtgtgtg gttttctgta caccacatgg ccattgacac tgtttcctgg cagatcctgg   120
ttcgtgatct gcagactctg taccgtaacg gttccctggg ttccaaaggt tcttcatttc   180
gccaatgggc cgaggcaatc caaaactaca aagcgagcga ctcggaacgt aaccattgga   240
acaagctggt tatggaaact gcatcgtcga tcagcgcgct gccgacctcc actggttc     298
```

<210> SEQ ID NO 266
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 266

```
aaaactacaa agcgagcgac tcggaacgta accattggaa caagctggtt atggaaactg    60
catcgtcgat cagcgcgctg ccgacctcca ctggttctcg cgtacgtctc tccgttctc    120 tgtctcctga aaaactgct tctctgatca agggtggcat cgatcgtcag gatgtaagcg   180
tatacgattc tctgctgact tctgttggcc tggctttgca acacatcgcg ccgactggcc   240
cgtctatggt tacaatcgag ggtcacggcc gcgaagaagt tgaccagacc ctggatg      297
```

<210> SEQ ID NO 267
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 267

```
ttctgttggc ctggctttgc aacacatcgc gccgactggc ccgtctatgg ttacaatcga      60
gggtcacggc cgcgaagaag ttgaccagac cctggatgtt tctcgtacga tgggctggtt     120
cactaccatg tatccgttcg aaatcccgcg tctgtcgacg gaaaacatcg tgcagggtgt     180
tgttgctgta agtgaacgct ccgccaagt tccggctcgc ggtgttggtt atggtactct     240
gtacggttac acccagcacc ctctgccgca ggttactgtt aactacctgg gccagctg      298
```

<210> SEQ ID NO 268
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 268

```
acacccagca ccctctgccg caggttactg ttaactacct gggccagctg gctcgtaaac      60
agagcaagcc gaaagaatgg gttctggcag ttggtgataa cgagttcgag tacggtctga     120
tgacctcccc ggaggataag gaccgttcga gctccgcagt ggatgttacg gccgtctgca     180
tcgacgggac gatgatcatc gatgtggact cggcttggtc tttggaagaa tctgaacagt     240
tcatctcgtc aattgaagaa ggtctgaaca aaatcctgga cggtcgtgca tcccagc        297
```

<210> SEQ ID NO 269
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 269

```
cgtaaacaga gcaagccgaa agaatgggtt ctggcagttg gtgataacga gttcgagtac      60
ggtctgatga cctccccgga ggataaggac cgttcgagct ccgcagtgga tgttacggcc     120
gtctgcatcg acgggacgat gatcatcgat gtggactcgg cttggtcttt ggaagaatct     180
gaacagttca tctcgtcaat tgaagaaggt ctgaacaaaa tcctggacgg tcgtgcatcc     240
cagcagacta gccgctttcc ggatgtgccg cagccagcag agacctacac cccatac        297
```

<210> SEQ ID NO 270
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 270

```
gatgtggact cggcttggtc tttggaagaa tctgaacagt tcatctcgtc aattgaagaa      60
ggtctgaaca aaatcctgga cggtcgtgca tcccagcaga ctagccgctt tccggatgtg     120
ccgcagccag cagagaccta caccccatac ttcgaatatc tggaaccgcc gcgcagggc      180 ccgaccctgt ttctgctgcc accgggtgaa ggtggtgcgg aatcttactt caacaacatc     240
```
gtcaaacgct tgcgtcaaac taacatggtt gtctttaaca actactacct gcactcc 297

<210> SEQ ID NO 271
<211> LENGTH: 296
<212> TYPE: DNA
<213> ORGANISM: Artificial Sequence
<220> FEATURE:
<223> OTHER INFORMATION: Synthetic nucleotide

<400> SEQUENCE: 271
gaatatctgg aaccgccgcg ccagggcccg accctgtttc tgctgccacc gggtgaaggt 60
ggtgcggaat cttacttcaa caacatcgtc aaacgcttgc gtcaaactaa catggttgtc 120
tttaacaact actacctgca ctccaaacgt ctgcgcacct tcgaggaact ggctgaaatg 180
tatctggacc aggtacgcgg catccaaccg cacggtccat accacttcat cggctggagc 240
ttcgggggca ttctggcgat ggagatgtcc cgtcgtctgg ttgcgagcga cgaaaa 296

<210> SEQ ID NO 272
<211> LENGTH: 282
<212> TYPE: DNA
<213> ORGANISM: Artificial Sequence
<220> FEATURE:
<223> OTHER INFORMATION: Synthetic nucleotide

<400> SEQUENCE: 272
ggcattctgg cgatggagat gtcccgtcgt ctggttgcga gcgacgaaaa aattggtttt 60
ctgggtatta tcgacaccta tttcaacgta cgtggtgcca ctcgcaccat tggccttggt 120
gatactgaaa tcctggatcc gatccaccac atctataacc cggacccggc aaactttcag 180
cgtctgccgt ctgccaccga ccgtatcgtc ctgtttaagg ccatgcgtcc gaataataaa 240
tatgaatcag aaaaccagcg tcgcctgtat gagtactacg ac 282

<210> SEQ ID NO 273
<211> LENGTH: 202
<212> TYPE: DNA
<213> ORGANISM: Artificial Sequence
<220> FEATURE:
<223> OTHER INFORMATION: Synthetic nucleotide

<400> SEQUENCE: 273
ctacgacgcg ttagattcca cggactggac cgcatgttac caggcgatcc ctacctcctc 60
atggtcgcgc ctgcgcacga tccacacctt cccgggttcg gaaatccaca accgctggtc 120
ccgttgcgtt cgtctgagcc gtaacaccag ccttgccatc gacccgtctc tggcggctca 180
gtacatcggt cgttggaagt aa 202

<210> SEQ ID NO 274
<211> LENGTH: 980
<212> TYPE: DNA
<213> ORGANISM: Artificial Sequence
<220> FEATURE:
<223> OTHER INFORMATION: Synthetic nucleotide

<400> SEQUENCE: 274
atgacccaat tgaagccgcc taacgggacc actccgatcg gcttcagcgc cactactagc 60
ctgaacgcta gcggctcttc ctcggttaag aatggtacca tcaagccttc gaatggtatc 120
ttcaaacctt ctactcgtga caccatggac ccgtgctcgg caacgccgc tgacggctcc 180 attcgcgtac gttttcgcgg tggcatcgaa cgttggaaag agtgtgtaaa ccaagtgccg 240
gagcgttgcg acctgtctgg tctgaccacg dacagcaccc gctaccagct ggcttcgacc 300

```
ggcttcggcg acgcgagcgc ggcttaccag gaacgtctga tgactgtgcc ggtagatgtt      360
catgctgcgc tccaggagct gtgcctggaa cgccgcgtct ctgtgggttc tgtgatcaac      420
ttcagcgttc accagatgct gaagggtttt ggcaacggta ctcacactat caccgcgagc      480
ctgcaccgcg aacagaatct gcagaactcc tctccgtctt gggtcgtttc ccctactatc      540
gtgacccatg aaaccgcga tggctggtca gtggcgcagg cagtggagtc tatcgaggct      600
ggtcgtggct ccgaaaagga atctgtgacc gcgattgatt ccggctcctc cctggtcaaa      660
atgggtctgt tcgatctgct ggtttccttc gtcgatgcgg atgacgcgcg tatcccttgc      720
ttcgactttc cgctggctgt tattgtgcgc gagtgcgatg caaacctgtc tctcacccTt      780
cgcttctcgg actgcctgtt caacgaggaa accatttgta atttcacgga tgccctcaat      840
atcctgttgg ctgaggcagt tatcggtcgt gtaactccgg tagccgatat cgagctgctg      900
tctgcagagc agaaacaaca gctggaggaa tggaacaaca ccgatggtga atatccgtct      960
agcaagcgtc tgcaccacct                                                  980
```

<210> SEQ ID NO 275
<211> LENGTH: 1203
<212> TYPE: DNA
<213> ORGANISM: Artificial Sequence
<220> FEATURE:
<223> OTHER INFORMATION: Synthetic nucleotide

<400> SEQUENCE: 275

```
gtgaatatcc gtctagcaag cgtctgcacc acctgattga agaggtggtg gaacgtcacg       60
aagacaaaat cgctgtggtg tgcgacgaac gtgaactgac ttacggtgaa ctcaatgccc      120
agggcaactc cctggcgcgt tacctgcgca gcattggtat tctgcctgaa cagctggttg      180
cgctgtttct ggacaaatcc gaaaaattga tcgtaaccat cctgggcgtc tggaaatccg      240
gtgctgctta cgtgccaatt gacccgacct accctgacga acgtgttcgt ttcgttctgg      300
acgacacgaa agcccgtgcg attatcgctt ccaatcagca tgttgaacgc ctccagcgtg      360
aagtaatcgg tgatcgcaac ctgtgcatca tccgtctcga accactgctg gcgagccttg      420
cgcaggattc ttctaaattc cctgcccaca acctggatga tttgccgctg accagccagc      480
agctggcgta cgttacttat accagcggta ccaccggctt tccgaaaggc attttcaaac      540
agcacactaa cgttgttaac tccatcacag acctgtccgc tcgttacggt gttgcaggtc      600
aacaccatga agctatcctg ctcttcagtg cttgcgtttt cgaaccgttc gttcgtcaga      660
ctctgatggc cctggtgaac ggtcacctgc tcgccgtgat aacgatgta gaaaaatatg      720 acgctgacac cctcctccca tttatccgcc gtcactctat cacctatctg aacggtactg      780
cgtcggttct ccaagagtat gacttctctg actgtcgag cctgaaccgt atcatcctgg      840
tgggcgagaa cctgaccgaa gcacgttacc tggcactgcg tcagcgtttc aaaaatcgta      900
ttctgaacga gtacgtttc accgagtctg cgttcgtgac tgcgctgaaa atttttcgatc      960 cggaaagcac ccgcaaagat acctccctgg ggcgtccggt gcgcaatgtt aaatgctata     1020
tcttgaaccc tagcctgaaa cgcgtgccaa ttggtgctac aggtgagctg catattggcg     1080
gcctgggtat ctccaagggt tacttgaatc gtccggaact gacgccgcac cgcttcatcc     1140
cgaacccgtt tcagaccgat tgcgaaaaac agctgggtat caactctctg atgtacaaaa     1200
ccg                                                                   1203
```

<210> SEQ ID NO 276

```
<211> LENGTH: 645
<212> TYPE: DNA
<213> ORGANISM: Artificial Sequence
<220> FEATURE:
<223> OTHER INFORMATION: Synthetic nucleotide

<400> SEQUENCE: 276
atcgtccgga actgacgccg caccgcttca tcccgaaccc gtttcagacc gattgcgaaa      60
aacagctggg tatcaactct ctgatgtaca aaaccggtga tctggctcgc tggctcccga     120
acggtgaagt tgaatacctg ggccgtgcgg atttccagat caaactgcgc ggtattcgta     180
ttgagccggg cgaaatcgag actatgctgg cgatgtatcc gcgcgttcgt acctccctgg     240
tggtttccaa gaaattacgt aacggtcctg aagaaacaac gaacgaacac ctggtaggct     300
actacgtatg cgactccgca tctgtttccg aagcggatct gctgtccttc ctggagaaga     360
agctgccgcg ttatatgatt ccgactcgtc tggtacagct gagccagatc ccggttaacg     420
tcaacggtaa agccgatctg cgtgctctgc cggcggttga tatctccaac agcaccgaag     480
ttcgttctga tctgcgtggt gataccgaaa ttgcctcgg cgaaatctgg gcggacgtgc      540
tgggcgcgcg tcagcgttcg gttagccgta acgataactt tttccgcctc ggtggccact     600
ctatcacctg catccagctg attgcgcgta tccgtcagcg tcagc                     645

<210> SEQ ID NO 277
<211> LENGTH: 1043
<212> TYPE: DNA
<213> ORGANISM: Artificial Sequence
<220> FEATURE:
<223> OTHER INFORMATION: Synthetic nucleotide

<400> SEQUENCE: 277
acctgcatcc agctgattgc gcgtatccgt cagcgtcagc gtttgtctgt gtctatctct      60
gtggaagacg tgtttgctac acgcactctt gagcgtatgg ccgacctgtt gcaaaacaaa     120
cagcaagaga aatgcgacaa accacacgaa gcaccgactg aactgcttga agaaaacgct     180
gcgactgata acatctacct ggcgaacagc ctgcagcaag gtttcgtcta ccattacctg     240
aaaagcatgg aacaaagtga tgcttatgta atgcagagcg ttctgcgtta caacaccacc     300
cttttccccgg atctgttcca gcgtgcctgg aaacacgcgc agcaaagctt cccggctctg     360
cgtctgcgct tctcttggga aaaagaagtc ttccagctgc tggatcagga cccgcctctg     420
gactggcgtt cctctactt cactgatgtg gcggctggtg cagtagaaga ccgtaaactg     480
gaagatttac gccgccagga cctcaccgag cgtttttaaac tggatgtggg ccgtctgttt     540
cgcgtttacc tgatcaaaca cagcgaaaac cgtttcactt gtctgttctc ttgtcaccac     600
gctatcctgg acggctggtc cttaccgctt ctgttcgaaa agtacacga acatacctg      660
caactgctgc acggcgataa cctgacctcc tctatggatg atccatacac ccgtacccaa     720
cgctacctgc atgcgcaccg cgaagatcac ctcgactttt gggctggcgt ggtgcagaaa     780
atcaacgaac gttgcgatat gaatgctctg ttaaacgaac gcagccgcta taaagtgcag     840
ctggccgact acgatcaggt acaggaacag cgtcagctga cgatcgctct gagcggtgac     900
gcgtggctgg cggatctgcg ccagacatgc agtgcgcagg gcatcacgct gcactctatc     960
ctgcaatttg tatggcatgc agttctgcat gcctacggtg gcggtactca cactatcact    1020
ggcaccacta tttctggtcg caa                                             1043

<210> SEQ ID NO 278
<211> LENGTH: 1245
```

```
<212> TYPE: DNA
<213> ORGANISM: Artificial Sequence
<220> FEATURE:
<223> OTHER INFORMATION: Synthetic nucleotide

<400> SEQUENCE: 278
acggtggcgg tactcacact atcactggca ccactatttc tggtcgcaac ctcccgatcc      60
tgggtatcga gcgtgcggta ggcccgtaca ttaacaccct gccgttagtg ttggaccatt     120
ctacttttaa agacaagacg atcatggaag ctattgaaga cgtccaagcg aaggtgaatg     180
ttatgaactc ccgtggtaat gtagaactgg gtcgcctgca caaaaccgac ctgaaacatg     240
gcctgttcga ttctctgttt gtgctggaaa actatccaaa cctggataaa tcccgtactc     300
tggagcacca aactgaactg ggttactcca tcgagggtgg taccgaaaaa ctgaactatc     360
cgctggcggt gattgctcgt gaggttgaga ccactggcgg ctttactgtt agcatctgct     420
atgcgagcga actgtttgaa gaggtgatga tcagcgagct tctccatatg gtacaggata     480
ccctgatgca ggttgcacgc gggctcaacg aacctgtggg ctccctggaa tacctgtctt     540
ccatccagtt agagcagctg gcagcgtgga acgccaccga agcggagttc ccggacacga     600
ccctgcatga aatgttcgag aacgaagcat ctcaaaagcc ggataaaatt gcagtcgtgt     660
acgaagaaac ctctctgacc tatcgcgagc tgaacgaacg tgccaatcgc atggcgcacc     720
agctgcgttc cgacgtttct ccgaacccga acgaagtgat cgcgctggtt atggacaaga     780
gtgaacacat gatcgtaaat atcttggctg tgtggaaatc tggtggcgca tacgtgccga     840
tcgatccggg ctacccgaat gaccgtattc agtatatcct cgaggacact caggcgttgg     900
ctgttatcgc agattcttgt tacctgcctc gtatcaaagg tatggccgcg tctggtacgc     960
tgctctaccc gtctgtcctg ccggcaaacc cagacagcaa atggtctgtg tcaaacccgt    1020
cgccgctgtc tcgtagcacc gacctggcat acatcatcta cacctctggc accaccggcc    1080
gcccgaaagg cgtgactgtg gagcatcacg gtgtggtgaa cctgcaggta tccctgagca    1140
aagttttggg tctgcgtgac accgacgacg aagtcatcct gtcttttctct aactacgttt    1200
tcgatcactt cgtagaacag atgactgatg ctatcctgaa cgggc                    1245

<210> SEQ ID NO 279
<211> LENGTH: 1157
<212> TYPE: DNA
<213> ORGANISM: Artificial Sequence
<220> FEATURE:
<223> OTHER INFORMATION: Synthetic nucleotide

<400> SEQUENCE: 279
ctaactacgt tttcgatcac ttcgtagaac agatgactga tgctatcctg aacgggcaga      60
cgctgctggt tctgaacgat ggtatgcgtg gtgacaaaga acgcctgtac cgctacatcg     120
aaaagaaccg tgtaacttat ctgtctggta ctccatctgt ggtgtctatg tatgagttca     180
gccgtttcaa agaccacctg cgccgcgtcg attgcgtcgg tgaagctttc agcgagccgg     240
tcttcgacaa aatccgtgaa accttccacg gtttggttat caatggttat ggcccaactg     300
aagttagcat cactacccat aagcgtttat accctttccc agagcgccgc atggataagt     360
cgatcggcca gcaggtccac aactctacta gctacgtact gaatgaagat atgaagcgta     420
ccccgatcgg tgctgtgggt gagctgtacc tgggcggtga agtgttgtc cgcggttatc     480
ataatcgtgc ggatgttacc gccgagcgct tcatcccgaa cccgttccag tctgaggaag     540
ataaacgtga aggccgtaac agtcgcctgt acaagacggg tgatctggtt cgctggatcc     600
```

| | |
|---|---|
| cgggtagctc cggcgaagtc gaatacctgg gtcgcaatga cttccaggtt aagattcgcg | 660 |
| gcctccgtat cgagctgggt gaaatcgaag cgatcctgag cagctaccac ggcattaaac | 720 |
| agagcgtagt gatcgcaaaa gactgccgtg aggggggcaca gaaattcctg gtcggctatt | 780 |
| acgttgcaga cgctgccctg ccgtccgcag cgatccgtcg tttcatgcag tcgcgcctcc | 840 |
| cgggttacat ggttccgtcc cgtctgatcc tggtttctaa attccctgtt actccgtccg | 900 |
| ggaagctgga caccaaagca ctgccgccgg cggaggaaga aagcgaaatc gacgttgttc | 960 |
| caccgcgctc cgaaattgag cgttctctct gcgacatctg ggctgaactg ctggaaatgc | 1020 |
| acccggaaga aatcggcatt tactctgact tcttctcctt gggcggcgac agcctgaaat | 1080 |
| ctactaagtt atccttcatg atccatgagt cctttaaccg tgctgtgagc gttagcgcgt | 1140 |
| tattctgcca tcgcaca | 1157 |

<210> SEQ ID NO 280
<211> LENGTH: 1066
<212> TYPE: DNA
<213> ORGANISM: Artificial Sequence
<220> FEATURE:
<223> OTHER INFORMATION: Synthetic nucleotide

<400> SEQUENCE: 280

| | |
|---|---|
| tccttcatga tccatgagtc ctttaaccgt gctgtgagcg ttagcgcgtt attctgccat | 60 |
| cgcacagttg aagctcaaac tcacctgatc ttgaacgacg cagcagatgt acacgaaatt | 120 |
| accccgatcg attgcaacga cacccagatg atcccggttt cccgtgcaca ggaacgtctg | 180 |
| ctgttcattc atgaattcga aaacggttct aacgcttaca acattgacgc ggctttcgaa | 240 |
| ctgccaggtt ctgtggacgc gagcctgctg aacaggccc ttcgtggcaa cctggcacgt | 300 |
| cacgaagcac tgcgcaccct gctggttaaa gatcacgcca ctggtattta cctgcagaaa | 360 |
| gtactgagtc cggacgaagc gcaaggtatg ttttctgtta atgtagatac tgctaaacag | 420 |
| gttgaacgtc tggatcagga aattgcttct ctgtctcagc acgtcttccg cctggacgac | 480 |
| gaactgccgt gggaggcgcg catcctgaaa ctggaatctg gcggtctgta cctgatcttg | 540 |
| gccttccacc acacctgctt cgatgcatgg agcctgaaag ttttcgaaca ggagctgcgc | 600 |
| gcgctgtacg cagcgcttca gaaaacgaaa tctgcagcga acttaccggc attaaaagca | 660 |
| cagtataagg aatacgctct gtaccaccgc cgccagctta cgggcgaccg catgcgtaac | 720 |
| ctgtccgatt tctggttacg taaactgatc ggtctggaac cactgcagct gatcaccgat | 780 |
| cgtccgcgtc cggttcagtt caaatacgac ggtgacgatc tgagcatcga actgtccaag | 840 |
| aaagagaccg aaaacctgcg cggcgttgca aaacgttgta agtcttcctt atatgttgta | 900 |
| ctggtatctg tttactgtgt catgctggca agctacgcca accagagcga tgttagcgtg | 960 |
| ggcatcccag tatcacaccg tacgcacccg cagttccagt ctgttatcgg cttttttcgtt | 1020 |
| aacctggtcg ttctgcgtgt agatatcagc cagtccgcta tttgcg | 1066 |

<210> SEQ ID NO 281
<211> LENGTH: 894
<212> TYPE: DNA
<213> ORGANISM: Artificial Sequence
<220> FEATURE:
<223> OTHER INFORMATION: Synthetic nucleotide

<400> SEQUENCE: 281

| | |
|---|---|
| ggtcgttctg cgtgtagata tcagccagtc cgctatttgc ggtttaatcc gtcgcgtcat | 60 |
| gaaagaactg gttgacgcgc agctgcacca ggatatgccg ttccaggaag ttacgaaact | 120 |

```
gctgcaggtg gataacgatc ctagccgtca cccgttggtt cagaacgtat ttaactttga      180
gtctcgcgcg aacggtgaac acgatgcccg ctctgaagac gagggctctc ttgcattcaa      240
tcagtaccgt ccggttcagc cggttgacag cgtggccaaa ttcgatctga acgccaccgt      300
caccgaactg gaatccggtc tgcgtgttaa tttcaactac gcgaccagct tattcaataa      360
atccaccatc cagggcttcc tgcacacata tgaataccttc tgcgtcagc tgtccgaact      420 gagcgctgaa ggcatcaacg aagataccca gctgtcactg gttcgcccga ctgagaacgg      480
ggatctgcac ctgccactgg cccagtctcc gctcgcgacc actgcagaag aacagaaagt      540
tgcttccctg aaccaggctt cgaacgtga agccttcctg gcggcggaaa aaatcgccgt      600
tgttcaaggg gaccgcgctc tgtcgtatgc cgacctgaac ggtcaggcta atcaactggc      660
gcgttatatc cagtccgtct cctgcatcgg tgccgacgac ggcatcgccc tgatgctgga      720
aaagagcatc gatactatca tctgcattct ggcaatctgg aaagcaggcg ccgcgtatgt      780
gccgctggat ccgacctacc caccaggccg tgtacaactg atcctggagg aaatcaaagc      840
gaaagctgtg ctggtacact cttcccacgc ctctaaatgt gaacgtcacg gtgc           894

<210> SEQ ID NO 282
<211> LENGTH: 1325
<212> TYPE: DNA
<213> ORGANISM: Artificial Sequence
<220> FEATURE:
<223> OTHER INFORMATION: Synthetic nucleotide

<400> SEQUENCE: 282
cctctaaatg tgaacgtcac ggtgccaaag tcattgcagt agactctccg gctattgaaa       60
cggcagtgag ccagcagtct gcagctgatc tgccgaccat tgctagcctg gtaatctgg      120 catatatcat ctttactagc ggcacttctg gcaaaccgaa aggcgttctg gtagagcaaa      180
aagccgttct gctgctgcgc gacgccctgc gtgagcgtta cttcggtcgt gattgtacca      240
aacatcacgg tgttctgttc ctgagcaact acgttttcga cttctccgta gaacagctgg      300
ttctgtctgt actctcaggc cacaaactga ttgtcccgcc ggcggagttt gtggcggatg      360
acgaattcta tcgtatggcc tctacccacg gtctttctta cctgtctggc accccgagcc      420
tgcttcaaaa aatcgatctg gcacgtctgg atcacctgca ggttgtaacc gcggcgggtg      480
aggaactcca cgcgacccag tacgaaaaaa tgcgtcgtcg ttttaacggt ccaatctaca      540
acgcttatgg tgttaccgag acaacggtgt acaacatcat cgctgaattc accaccaact      600
ccatcttcga aaacgcatta cgcgaagtcc tgccgggcac ccgtgcgtac gttctgaacg      660
cggcgctgca gccggttcca ttcgacgctg tgggtgaact gtatctggcc ggcgatagcg      720
taacccgtgg ttacctgaac cagccgttgc tgaccgatca gcgtttcatc cctaacccgt      780
tctgcaagga agaagacatc gcgatgggtc gttcgctcg tctgtacaaa accggcgacc      840
tggttcgctc tcgcttcaac cgccagcagc agccgcagct ggaatacctg gccgtggcg      900 acctgcagat taaaatgcgt ggttaccgca ttgaaattag cgaagtacag aacgtgctga      960
cctcctcccc gggcgtacgc gaaggtgcgg ttgtggctaa atatgaaaac aacgacacgt     1020
atagccgtac tgcacattcc ttagtcggtt attataccac tgataacgaa acagtttcag     1080
aagctgatat cctcaccttc atgaaagcgc gtctgccgac ctatatggtg ccttctcacc     1140
tgtgctgcct ggaaggtgct ctgccagtca ctattaacgg taaactggac gttcgtcgtc     1200
tgcctgaaat tatcaacgac agtgcgcaat cctcatattc cccgccgcgc aacattatcg     1260
```

```
aagcgaaaat gtgccgttta tgggaaagcg cgctgggtat ggaacgctgc ggtattgacg   1320
atgac                                                              1325

<210> SEQ ID NO 283
<211> LENGTH: 1251
<212> TYPE: DNA
<213> ORGANISM: Artificial Sequence
<220> FEATURE:
<223> OTHER INFORMATION: Synthetic nucleotide

<400> SEQUENCE: 283
cgtttatggg aaagcgcgct gggtatggaa cgctgcggta ttgacgatga cctcttcaag     60 ctggggggg attctatcac cagtctgcac ctcgtcgcac agattcacaa tcaggtgggc    120
tgtaagatta ccgtgcgcga tattttcgaa caccgtaccg cgcgtgctct ccacgatcac    180
gttttcatga aggatagcga tcgctctaac gtcacccagt tccgtaccga gcaggggccg    240
gtcattggcg aagctccgct gctgccgatc caggattggt tcttgagcaa agctctgcag    300
caccctatgt actggaacca cacgttctac gtacgtaccc cggaactgga cgttgattcc    360
ctgagtgcgg ccgttcgtga cctgcagcag taccacgacg ttttccgcat gcgcctgaaa    420
cgcgaagaag ttggctttgt acagtccttt gccgaagact tttccccggc gcagctgcgt    480
gtactgaacg tgaaggacgt ggatggtagc gcggcggtta acgaaatcct ggacggttgg    540
caaagcggct tcaacctgga aaacggtccg atcggctcga tcggttatct gcatggctat    600
gaagaccgct ccgcacgtgt gtggttttct gtacaccaca tggccattga cactgtttcc    660
tggcagatcc tggttcgtga tctgcagact ctgtaccgta acggttccct gggttccaaa    720
ggttcttcat ttcgccaatg ggccgaggca atccaaaact acaaagcgag cgactcggaa    780
cgtaaccatt ggaacaagct ggttatggaa actgcatcgt cgatcagcgc gctgccgacc    840
tccactggtt ctcgcgtacg tctctcccgt tctctgtctc ctgaaaaaac tgcttctctg    900
atccagggtg gcatcgatcg tcaggatgta agcgtatacg attctctgct gacttctgtt    960
ggcctggctt tgcaacacat cgcgccgact ggcccgtcta tggttacaat cgagggtcac   1020
ggccgcgaag aagttgacca gaccctggat gtttctcgta cgatgggctg gttcactacc   1080
atgtatccgt tcgaaatccc gcgtctgtcg acggaaaaca tcgtgcaggg tgttgttgct   1140
gtaagtgaac gcttccgcca agttccggct cgcggtgttg gttatggtac tctgtacggt   1200
tacacccagc accctctgcc gcaggttact gttaactacc tgggccagct g           1251

<210> SEQ ID NO 284
<211> LENGTH: 1076
<212> TYPE: DNA
<213> ORGANISM: Artificial Sequence
<220> FEATURE:
<223> OTHER INFORMATION: Synthetic nucleotide

<400> SEQUENCE: 284
acacccagca ccctctgccg caggttactg ttaactacct gggccagctg gctcgtaaac     60
agagcaagcc gaaagaatgg gttctggcag ttggtgataa cgagttcgag tacggtctga    120
tgacctcccc ggaggataag gaccgttcga gctccgcagt ggatgttacg gccgtctgca    180
tcgacgggac gatgatcatc gatgtggact cggcttggtc ttttggaagaa tctgaacagt    240 tcatctcgtc aattgaagaa ggtctgaaca aaatcctgga cggtcgtgca tcccagcaga    300
ctagccgctt tccggatgtg ccgcagccag cagagaccta caccccatac ttcgaatatc    360
tggaaccgcc gcgccagggc ccgaccctgt ttctgctgcc accgggtgaa ggtggtgcgg    420
```

```
aatcttactt caacaacatc gtcaaacgct tgcgtcaaac taacatggtt gtctttaaca      480
actactacct gcactccaaa cgtctgcgca ccttcgagga actggctgaa atgtatctgg      540
accaggtacg cggcatccaa ccgcacggtc cataccactt catcggctgg agcttcgggg      600
gcattctggc gatggagatg tcccgtcgtc tggttgcgag cgacgaaaaa attggttttc      660
tgggtattat cgacacctat ttcaacgtac gtggtgccac tcgcaccatt ggccttggtg      720
atactgaaat cctggatccg atccaccaca tctataaccc ggacccggca aactttcagc      780
gtctgccgtc tgccaccgac cgtatcgtcc tgtttaaggc catgcgtccg aataataaat      840
atgaatcaga aaaccagcgt cgcctgtatg agtactacga cgcgttagat tccacggact      900
ggaccgcatg ttaccaggcg atccctacct cctcatggtc gcgcctgcgc acgatccaca      960
ccttcccggg ttcggaaatc cacaaccgct ggtcccgttg cgttcgtctg agccgtaaca     1020
ccagccttgc catcgacccg tctctggcgg ctcagtacat cggtcgttgg aagtaa        1076
```

METHOD OF PREPARING NUCLEIC ACID MOLECULES

CROSS REFERENCE TO PRIOR APPLICATIONS

This application is Continuation of U.S. patent application Ser. No. 14/235,799 filed on Jan. 29, 2014, which is a National Stage Application of PCT International Patent Application No. PCT/KR2012/006147 filed on Aug. 1, 2012, under 35 U.S.C. § 371, which claims priority to Korean Patent Application No. 10-2011-0076408 filed on Aug. 1, 2011, which are all hereby incorporated by reference in their entirety.

BACKGROUND

Typically employed DNA synthesis procedures for scalable DNA construction have the following disadvantages: (a) high cost of oligonucleotides, (b) low assembly efficiency into long DNA sequences, (c) time-consuming cloning, and (d) high cost of target DNA sequence validation. Above all, the major synthesis costs are the costs of oligonucleotides and sequencing. It would thus be desirable to design a protocol for massively parallelizing synthesis products in order to achieve effective, highly scalable DNA synthesis. DNA oligonucleotides derived from DNA microchips have previously been utilized to synthesize scalable low-cost DNA (Tian, J., et al., 2004). However, the low assembly efficiency of chip-derived oligonucleotides hinders target gene construction, and a laborious DNA assembly optimization process is consequently required. The inefficiency of DNA assembly from chip-derived oligonucleotides is largely associated with the incomplete removal of flanking regions of double-stranded (ds)-oligonucleotides prior to their assembly and the uneven concentration of each chip-cleaved oligonucleotide (Kim H., et al., 2011). Furthermore, it was observed that a greater number of oligonucleotides (i.e. higher complexity) in a DNA assembly pool made DNA assembly less efficient (Kim H., et al., 2011; Borovkov A. Y., et al., 2010). As a consequence, only a small sub-pool of oligonucleotides (i.e. <20) are often amplified to ensure high assembly efficiency. There is a need to develop a high-efficiency DNA assembly process using a large number of microchip oligonucleotides present in a pool in order to attain all advantages of ultra-low cost DNA microchip oligonucleotides.

For scalable DNA synthesis, it is preferable to decrease the sequencing cost for target DNA validation. In recent years, costs for high-throughput sequencing technologies have been considerably lowered. Under such circumstances, utilization of high-throughput sequencing technology has great potential for DNA synthesis at ultra-low cost. However, unlike colony-based Sanger sequencing validation, it is difficult to collect the desired DNA from a pool of high-throughput sequenced DNA mixtures. Although recent high-throughput sequencing technologies can be applied to partially addressable spots (for example, clonal spots available from Roche-454, Illumina and SOLiD, and single-molecule spots available from Helicos and PacBio), it is difficult to isolate target DNA due to the difficulty associated with the collection of the desired DNA from high-throughput sequencing plates. In a notable report (Matzas M., et al., 2010), chip-cleaved oligonucleotides were sequenced by 454 sequencing technology, and directly isolated from the 454 sequencing plate using a bead picker pipette. These sequence-validated 'oligonucleotides' were subsequently processed and used to assemble 200 bp target DNA fragments. This study demonstrates the possibility of convergence of next-generation sequencing technology and microchip oligonucleotides in terms of DNA synthesis cost reduction. In this study, however, high-throughput sequencing was carried out on chip oligonucleotides rather than on assembled DNA fragments. Accordingly, challenges associated with DNA assembly into larger sequences are still in early stages. Furthermore, an effective error-free oligonucleotide picking process necessitates a highly tuned bead picking robot and an image processing system.

A number of papers and patent publications are referenced and cited throughout the specification. The disclosures of the papers and patent publications are incorporated herein by reference in their entireties in order to more fully describe the state of the art to which the present disclosure pertains and the disclosure of the present disclosure.

SUMMARY

According to one embodiment of the present disclosure, there is provided a method of preparing nucleic acid molecules, including (a) providing nucleic acid fragments constituting at least a portion of the complete sequence of a target nucleic acid, (b) tagging the nucleic acid fragments with barcode sequences, (c) validating the sequences of the nucleic acid fragments tagged with the barcode sequences, and (d) recovering desired nucleic acid fragments among the sequence-validated nucleic acid fragments using the barcode sequences.

According to a further embodiment of the present disclosure, there is provided a method of preparing nucleic acid molecules, including (a) providing nucleic acid fragments constituting at least a portion of the complete sequence of a target nucleic acid, (b) assembling the nucleic acid fragments to synthesize intermediates having sizes whose sequences are validatable by a parallel sequencing technology, (c) tagging the intermediates with barcode sequences, (d) validating the sequences of the intermediates tagged with the barcode sequences, (e) recovering desired intermediates among the sequence-validated intermediates using the barcode sequences, and (f) assembling the recovered intermediates to form long nucleic acid molecules.

According to another embodiment of the present disclosure, there is provided a method of preparing nucleic acid molecules, including (a) providing a pool of oligonucleotides containing restriction enzyme digestion sequences and generic flanking sequences, (b) cleaving the restriction enzyme digestion sequence portions to provide a pool of mixtures including the oligonucleotides, each containing the generic flanking sequences at one end, and the oligonucleotides, each containing none of the generic flanking sequences at one end, and (c) assembling the oligonucleotides using the generic flanking sequences to randomly synthesize nucleic acid fragments.

According to yet another embodiment of the present disclosure, a method of preparing nucleic acid molecules, including (a) providing a pool of oligonucleotides, (b) assembling the oligonucleotides to randomly synthesize nucleic acid fragments, (c) connecting base sequences for amplification to the randomly synthesized nucleic acid fragments, and (d) amplifying the nucleic acid fragments with primers bound to the base sequences for amplification.

DETAILED DESCRIPTION

Figure 1:
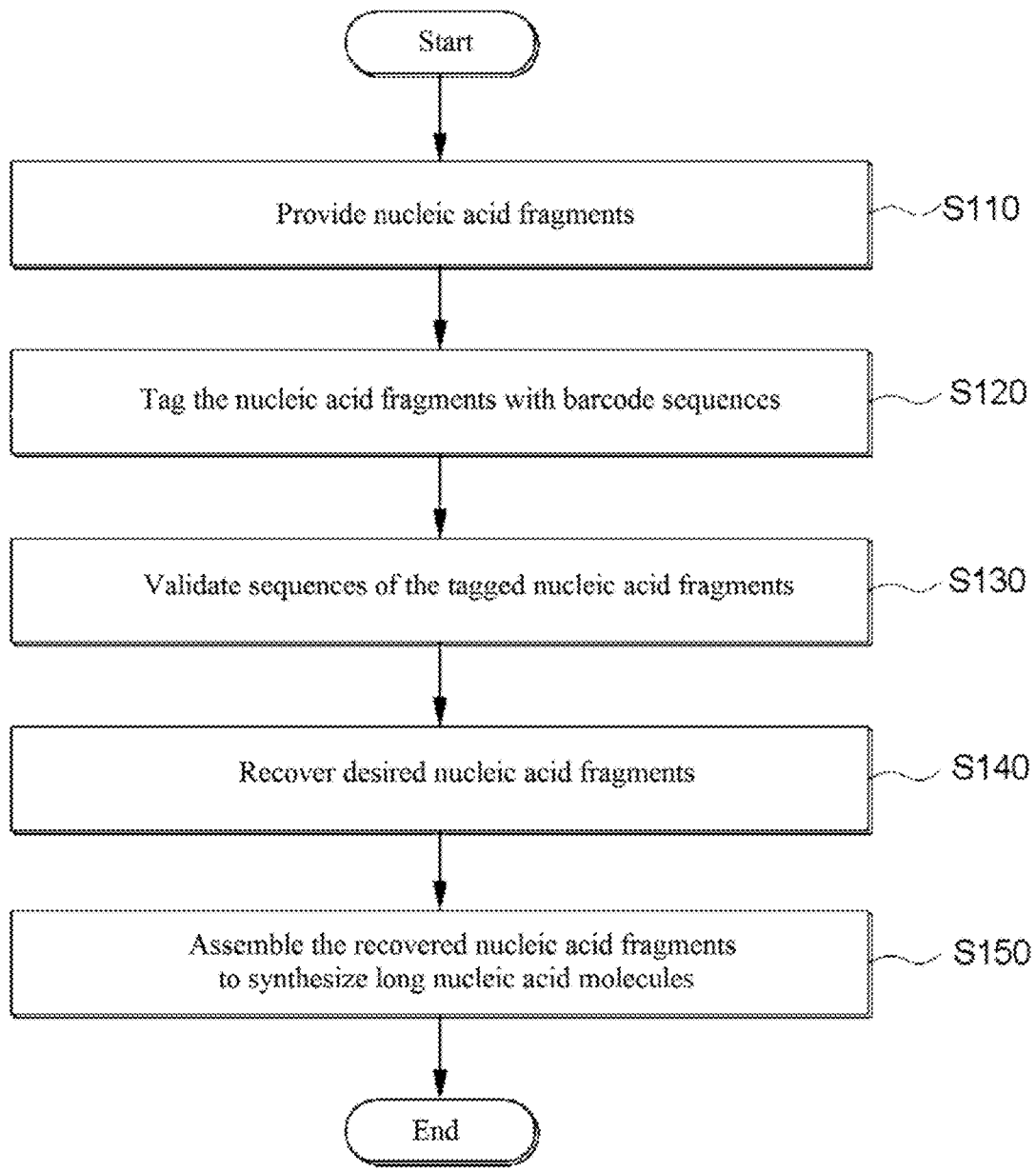
FIG. 1 is a flow chart illustrating a method of preparing nucleic acid molecules according to one embodiment of the present disclosure.

Embodiments of the present disclosure will now be described in more detail with reference to the accompanying drawings. These embodiments are provided so that this disclosure will fully convey the scope of the disclosure to those skilled in the art. Accordingly, the present disclosure may be embodied in many different forms and should not be construed as limited to the exemplary embodiments set forth herein. In the drawings, the dimensions, such as widths, lengths and thicknesses, of elements may be exaggerated for convenience. It will be understood that when a first element is referred to as being "connected" or "attached" to a second element, the first element can be directly connected or attached to the second element or a third element may also be interposed between the first and second elements.

FIG. 1 is a flow chart illustrating a method of preparing nucleic acid molecules according to one embodiment of the present disclosure. Referring to FIG. 1, in step S110, nucleic acid fragments constituting at least a portion of the complete sequence of a target nucleic acid are provided. The nucleic acid fragments may be naturally occurring or artificially synthesized ones. Preferably, the nucleic acid fragments are derived from DNA microchips providing several million kinds of base sequences at low costs or from a pool of synthetic oligonucleotides. The pool of synthetic oligonucleotides may be prepared by methods well known in the art. For example, the pool of synthetic oligonucleotides may be prepared from resin-based oligonucleotides but is not limited thereto. Preferably, the nucleic acid fragments are derived from DNA microchips.

When it is intended to synthesize large target nucleic acid molecules, the nucleic acid fragments may be ones that are free of sequence errors such as insertion, deletion, transition and transversion.

The nucleic acid fragments provided in step S110 may be directly extracted from a pool of oligonucleotides. Alternatively, the nucleic acid fragments may be prepared by amplifying and assembling oligonucleotides so as to have lengths above a predetermined level. When it is intended to synthesize long target nucleic acid molecules, the nucleic acid fragments may be made by various processes, including a hierarchical gene synthesis process (*Journal of Biotechnology* 151 (2011) 319-324) or a random gene synthesis process, which will be described below.

In the present specification, random gene synthesis is also referred to as "shotgun synthesis", and nucleic acid fragments made by such a shotgun synthesis method are also referred to as "shotgun products."

Shotgun sequencing is a process in which analyte DNA is randomly fragmented, sequencing adaptors are connected to the nucleic acid fragments, followed by high-throughput sequencing analysis. Shotgun sequencing includes arranging the individual fragments and identifying the complete sequence of the original analyte DNA using a computer program. Shotgun synthesis proceeds in the exact reverse order to that of the shotgun sequencing. Oligonucleotides constituting a portion of the sequence of nucleic acid molecules to be synthesized are constructed and assembled randomly to make nucleic acid fragments, which are analyzed by high-throughput sequencing. Desired nucleic acid fragments are recovered among the analyzed nucleic acid fragments and are used to make the final nucleic acid molecules.

According to one embodiment of the present disclosure, the nucleic acid fragments provided in step S110 may be shotgun products prepared by a shotgun synthesis method. Oligonucleotides designed to contain generic flanking sequences may be used to make the shotgun products.

Figure 2:
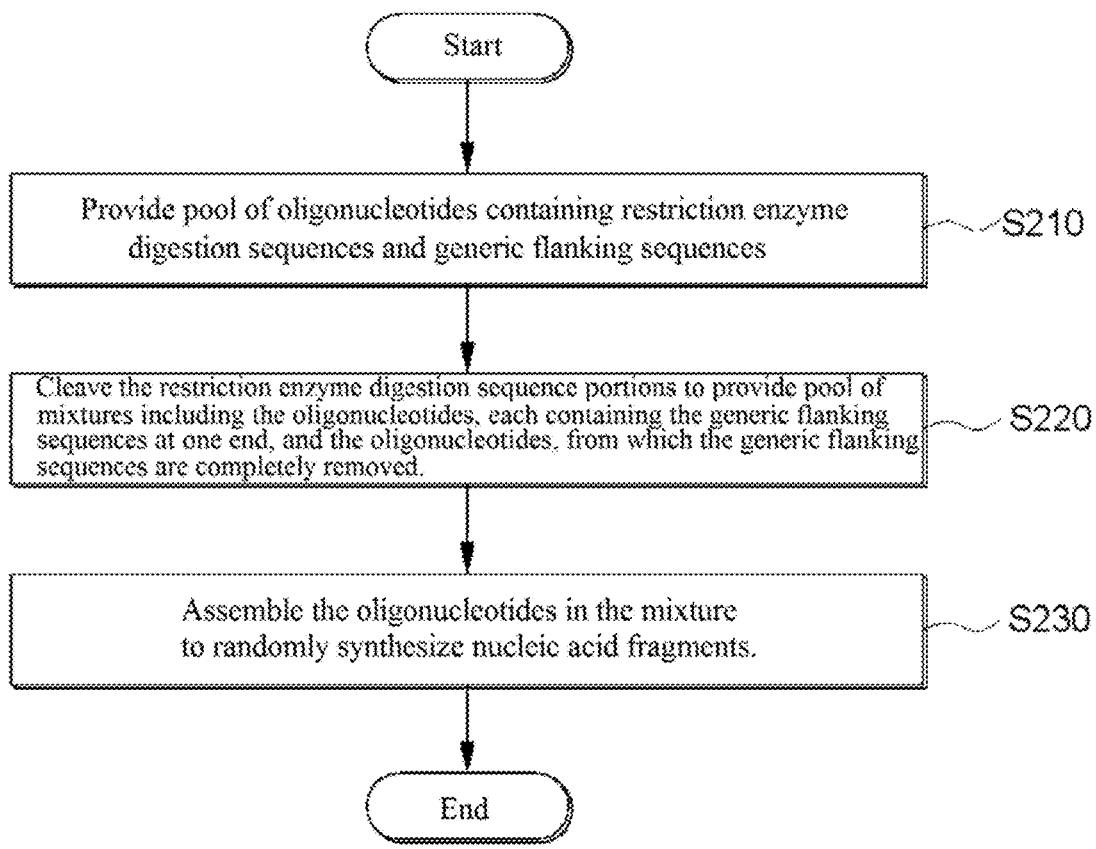
FIG. 2 is a flow chart illustrating a random gene synthesis process according to one embodiment of the present disclosure.

FIG. 2 is a flow chart illustrating a random gene synthesis process according to one embodiment of the present disclosure. Referring to FIG. 2, in step S210, a pool of oligonucleotides, each containing restriction enzyme digestion sequences and generic flanking sequences at least one end, is provided. In step S220, the restriction enzyme digestion sequence portions are cleaved to provide a pool of mixtures including the oligonucleotides, each containing the generic flanking sequences at one end, and the oligonucleotides, each containing none of the generic flanking sequences at one end. In step S230, the oligonucleotides in the mixture are assembled using the generic flanking sequences to randomly synthesize nucleic acid fragments.

In step S210, the generic flanking sequence may exist at one or both ends of the oligonucleotide. For example, the oligonucleotides used in the random gene synthesis (shotgun synthesis) process may contain, from the 5' to 3' direction, 5'-end generic flanking sequences, the oligonucleotide sequences constituting the target nucleic acid, and 3'-end generic flanking sequences.

The 5'-end generic flanking sequences and 3'-end generic flanking sequences existing at the ends of the oligonucleotides are priming regions where the amount of the oligonucleotide derived from DNA chips is amplified, and are used as annealing regions of primer sets for the production of a sufficient amount of the oligonucleotides.

The oligonucleotides may contain restriction enzyme digestion sequences. The nucleic acid fragments contain 5'-restriction enzyme digestion sequences with the 5'-end generic flanking sequences, and 3'-restriction enzyme digestion sequences with the 3'-end generic flanking sequences. The 5'-restriction enzyme digestion sequences and the 3'-restriction enzyme digestion sequences in the oligonucleotides may be identical to or different from each other.

The oligonucleotides are 50-500 base pairs (bp), more preferably 100-300 bp, even more preferably 120-200 bp, most preferably about 150 bp in length.

According to one embodiment of the present disclosure, the oligonucleotides may contain portions or all of the sequence of the target nucleic acid. When the oligonucleotides contain portions of the sequence of the target nucleic acid, the target oligonucleotides with varying sizes are sequentially assembled to synthesize the target nucleic acid molecules containing all of the sequence.

The pool of the oligonucleotides may be one that is cleaved from DNA microchips. Alternatively, the pool of the oligonucleotides may be a mixture of oligonucleotides synthesized on a solid. The cleaved oligonucleotides may be amplified to ensure an amount necessary for long gene synthesis. This amplification may be perform by polymerase chain reaction (PCR) using the generic flanking sequences.

Next, the generic flanking sequences are cleaved using a restriction enzyme recognizing the restriction enzyme digestion sequences in the amplified oligonucleotides. The pool of the cleaved oligonucleotides may take the form of a mixture including the oligonucleotides, each containing none of the generic flanking sequences because the restriction enzyme digestion sequences at both ends are completely cleaved, and the oligonucleotides, each containing the generic flanking sequences remaining at one end because only the restriction enzyme digestion sequences at one end are cleaved.

The oligonucleotides of the mixtures can be assembled by polymerase chain reaction assembly (PCA) using the generic flanking sequences. At this time, the oligonucleotides are sequentially assembled to make fragments with varying lengths. Such fragments may be randomly assembled to each other. Thus, the small or large fragments may be randomly assembled at various locations in the PCR solution to synthesize longer fragments containing all or portions of the sequence of the target nucleic acid molecules. This assembly may proceed until the oligonucleotides, each containing the generic flanking sequence at one end, overlap each other to make nucleic acid fragments containing the generic flanking sequences at both ends.

Figure 3:
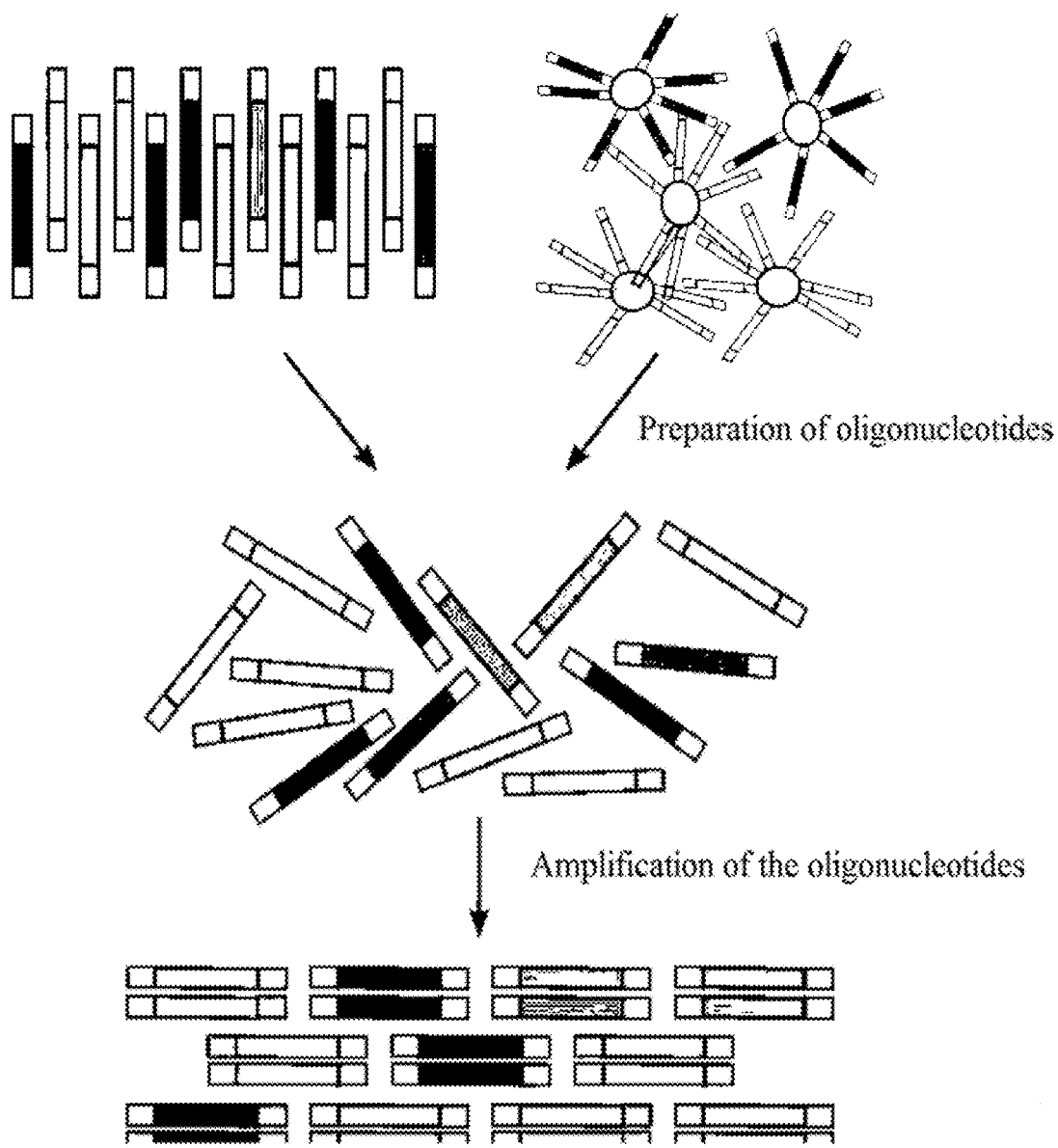
FIGS. 3 and 4 illustrate procedures for the synthesis of nucleic acid fragments by random synthesis processes.
Figure 4:
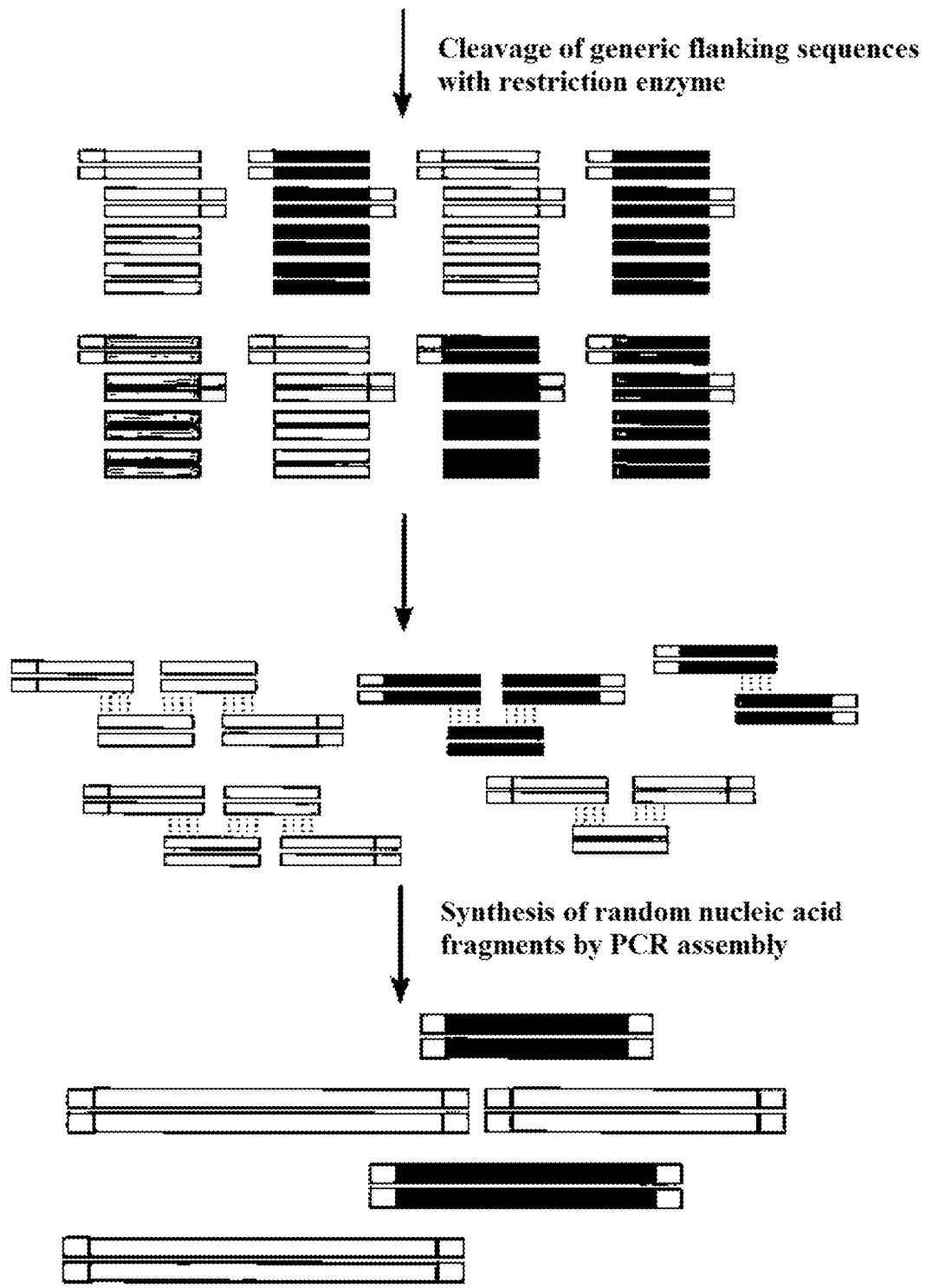

The oligonucleotides of step S210 are elaborately designed to form desired shotgun products. Several oligonucleotides may be assembled in such a manner that they overlap each other through some complementary sequences of the oligonucleotide sequences. The oligonucleotides are designed for random assembly to form shotgun products. For example, if a shotgun product (e.g., ~400 bp) containing the 5'-end regions of the target nucleic acid molecules consists of 5 target oligonucleotides, it may be formed through sequential assembly among the following oligonucleotides cleaved using restriction enzymes: from the 5' to 3' direction, to form a 5'-end region, a first oligonucleotide containing a 5'-end generic flanking sequence and a portion of the sequence of the target nucleic acid molecules and from which the restriction enzyme digestion sequences are partially cleaved; a second oligonucleotide including a region (e.g., 20-50 bp long) overlapping the 3'-end region of the first oligonucleotide; a third oligonucleotide including a region overlapping the 3'-end region of the second oligonucleotide; a fourth oligonucleotide including a region overlapping the 3'-end region of the third oligonucleotide; and a fifth oligonucleotide containing a sequence including a region overlapping the 3'-end region of the fourth oligonucleotide and a 3'-end generic flanking sequence. FIGS. 3 and 4 illustrate procedures for the synthesis of nucleic acid fragments by random synthesis processes.

In a modified embodiment, the nucleic acid fragments may be prepared by the following method.

First, a pool of oligonucleotides is provided. Next, raw oligonucleotides without the addition of generic flanking sequences, etc. are assembled to randomly synthesize nucleic acid fragments, unlike the previous embodiment. Base sequences for amplification are connected to the randomly synthesized nucleic acid fragment, and then the nucleic acid fragments are amplified with primers bound to the base sequences for amplification to obtain amplified nucleic acid fragments.

As described above, the preparation of nucleic acid molecules by random synthesis processes is advantageous in that several kinds of libraries of nucleic acid fragments can be prepared simultaneously.

According to one embodiment of the present disclosure, the nucleic acid fragments of step S110 may include the complete sequence of a target nucleic acid. For the synthesis of error-free long DNA, the sequences of the nucleic acid fragments may be validated using a parallel sequencing system. When the performance of the parallel sequencing system to validate the sequences of the nucleic acid fragments is taken into consideration, the nucleic acid fragments are preferably 20-3,000 bp, more preferably 200-1,000 bp, more preferably 300-500 bp, even more preferably 350-450 bp, most preferably 380-420 bp in length. Despite this preferred numerical range, an improvement in the performance of parallel sequencing systems for the analysis of several thousand by long DNA can extend the size of the nucleic acid fragments to several thousand by long DNA.

The term "nucleotide" as used herein refers to a single- or double-stranded deoxyribonucleotide or ribonucleotide and includes naturally occurring nucleotide analogs unless stated otherwise (Scheit, Nucleotide Analogs, John Wiley, New York (1980); Uhlman and Peyman, Chemical Reviews, 90:543-584 (1990)).

The term "oligonucleotide" as used herein refers to an oligomer or polymer of nucleotides or an analog thereof. According to one embodiment of the present disclosure, the gene amplification is carried out by PCR. According to one embodiment of the present disclosure, the primers (for example, the generic flanking sequences) are used in gene amplification reactions.

The term "amplification reactions" as used herein refers to reactions for amplifying target nucleic acid sequences. Various amplification reactions were reported in the art and include, but are not limited to, polymerase chain reaction (PCR) (U.S. Pat. Nos. 4,683,195, 4,683,202, and 4,800,159), reverse transcription polymerase chain reaction (RT-PCR) (Sambrook et al., Molecular Cloning. A Laboratory Manual, 3rd ed. Cold Spring Harbor Press (2001)), the methods of Miller, H. I. (WO 89/06700) and Davey, C. et al. (EP 329,822), multiplex PCR (McPherson and Moller, 2000), ligase chain reaction (LCR) (17, 18), Gap-LCR (WO 90/01069), repair chain reaction (EP 439,182), transcription-mediated amplification (TMA) (19) (WO88/10315), self sustained sequence replication (20) (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (APPCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), and strand displacement amplification (21, 22). Other possible amplification methods are described in U.S. Pat. Nos. 5,242,794, 5,494, 810, and 4,988,617, and U.S. patent application Ser. No. 09/854,317.

In a most preferred embodiment of the present disclosure, the amplification procedure is carried out in accordance with PCR disclosed in U.S. Pat. Nos. 4,683,195, 4,683,202, and 4,800,159.

PCR is one of the most well-known nucleic acid amplification methods and many modifications and applications thereof have been developed. For example, traditional PCR procedures have been modified to develop touchdown PCR, hot start PCR, nested PCR, and booster PCR with improved PCR specificity or sensitivity. In addition, multiplex PCR, real-time PCR, differential display PCR (DD-PCR), rapid amplification of cDNA ends (RACE), inverse polymerase chain reaction (IPCR), vectorette PCR and thermal asymmetric interlaced PCR (TAIL-PCR) have been developed for specific applications. Details of PCR can be found in McPherson, M. J., and Moller, S. G. PCR. BIOS Scientific Publishers, Springer-Verlag New York Berlin Heidelberg, N.Y. (2000), the teachings of which are incorporated herein by reference. Examples of preferred target nucleic acid molecules that can be used in the present disclosure include, but are not particularly limited to, DNA (gDNA and cDNA) and RNA. DNA is more preferred. Examples of target nucleic acids suitable for use in the present disclosure include nucleic acids from prokaryotic cells, eukaryotic cells (e.g., protozoans, parasites, bacteria, yeasts, higher plants, lower animals, and higher animals, including mammals and humans), viruses (e.g., herpes virus, HIV, influenza virus, Epstein-Barr virus, hepatitis virus, and poliovirus), and viroids.

The primers used in the present disclosure are hybridized or annealed to sites of the template to form double-stranded structures. Suitable conditions of nucleic acid hybridization for the formation of such double stranded structures are described in Joseph Sambrook, et al., Molecular Cloning, A Laboratory Manual, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

A variety of DNA polymerases can be used for amplification in the present disclosure and include "Klenow" fragment of *E. coli* DNA polymerase I, thermostable DNA polymerases, and bacteriophage T7 DNA polymerase. Preferred are thermostable DNA polymerases that can be obtained from a variety of bacterial species, including DNA polymerases and Phusion polymerases of *Thermus aquaticus* (Taq), *Thermus thermophilus* (Tth), *Thermus filiformis*, *Thermis flavus*, *Thermococcus literalis*, *Pyrococcus furiosus* (Pfu), *Thermus antranikianii*, *Thermus caldophilus*, *Thermus chliarophilus*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana* and *Thermosipho africanus*. Most preferably, *Pyrococcus furiosus* (Pfu) or Phusion high-fidelity DNA polymerase is used.

When the polymerization reaction is carried out, it is preferred to provide excessive amounts of the components necessary for amplification to a reaction vessel. The excessive amounts of the components necessary for amplification refer to amounts of the components in which the amplification reaction is not substantially limited by the concentrations of the components. It is desirable to provide, to the reaction mixture, cofactors such as $Mg^{2+}$ and dATP, dCTP, dGTP and dTTP in amounts sufficient to reach a desired degree of amplification. All enzymes used in the amplification reaction may be active under the same reaction conditions. Indeed, a buffer allows all enzymes to reach their optimum reaction conditions. Thus, the use of a buffer enables the amplification of a single reactant without any change in reaction conditions such as the addition of other reactants.

In the present disclosure, annealing is carried out under stringent conditions that allow for specific binding between the target nucleotide sequences (e.g., the generic flanking sequences of the target oligonucleotides) and the primers. The stringent annealing conditions are sequence-dependent and vary depending on ambient environmental parameters.

The oligonucleotide pool thus amplified can be used to make primary amplification products. The primary amplification products can be used to prepare secondary amplification products, which can be assembled into larger target nucleic acid molecules (e.g., ≥10 kb).

The term "primer" as used herein refers to an oligonucleotide that can act as a point of initiation of synthesis when placed under conditions in which synthesis of a primer extension product complementary to a nucleic acid strand (a template) is induced, i.e., in the presence of nucleotides and a polymerase, such as DNA polymerase, and under appropriate temperature and pH conditions. Preferably, the primer is deoxyribonucleotide and a single strand. The primers used in the present disclosure may include naturally occurring dNMP (i.e., dAMP, dGMP, dCMP and dTMP), modified nucleotides, and non-naturally occurring nucleotides. Other examples of the primers include ribonucleotides.

The primers should be sufficiently long to prime the synthesis of extension products in the presence of a polymerase (such as DNA polymerase). The length of the primers may vary depending on many factors, e.g., temperature, application, and sources of the primers. The primers are typically 15-30 nucleotides long. Short primer molecules generally necessitate a lower temperature to form sufficiently stable hybridization composites with templates.

The term "annealing" or "priming" as used herein refers to the apposition of an oligodeoxynucleotide or nucleic acid to a template nucleic acid. The apposition enables the polymerase to polymerize nucleotides into a nucleic acid molecule complementary to the template nucleic acid or a portion thereof. The term "hybridization" as used herein refers to a process in which two single-stranded nucleic acids form a duplex structure by pairing of complementary base sequences. The hybridization may occur when complementarity between single-stranded nucleic acid sequences is perfectly matched or even when partially mismatching bases are present. The degree of complementarity necessary for hybridization may vary depending on hybridization reaction conditions, particularly temperature.

The term "complementary" as used herein means a level of complementarity sufficient to selectively hybridize with the nucleotide sequence under certain particular hybridization or annealing conditions, and is intended to include both substantially complementary and perfectly complementary, preferably perfectly complementary.

Referring back to FIG. 1, in step S120, the nucleic acid fragments are tagged with barcode sequences. The barcode sequences are introduced into the nucleic acid fragments to recover error-free fragments or other desired fragments among the nucleic acid fragments provided in the previous step or to selectively amplify and assemble them in order to synthesize target nucleic acid molecules. The barcode sequences may be added to the generic flanking sequences present at the ends of the nucleic acid fragments.

The kinds of the barcode sequences are not particularly limited so long as they can be added to distinguish the nucleic acid fragments from each other. The number of the kinds of the barcode sequences is preferably greater than that of the nucleic acid fragments to distinguish the individual nucleic acid fragments. For example, the barcode sequences may be mixtures of two or more kinds of randomly or intentionally designed oligonucleotides.

According to one embodiment of the present disclosure, poly-N degenerate-barcode sequences among the barcode sequences may use poly-N degenerate DNA or may also use sequences barcoded with two or more different sequences randomly made using a computer program well known in the art.

The tagging with the barcode sequences is not particularly limited and may be performed by a method selected from the group consisting of PCR, emulsion PCR and ligation. For example, assembly of the barcode sequences to shotgun synthesized DNA fragments by PCR or ligation of double-stranded (ds) DNA including poly-N degenerate-barcode sequences may be used for the tagging.

Figure 5:
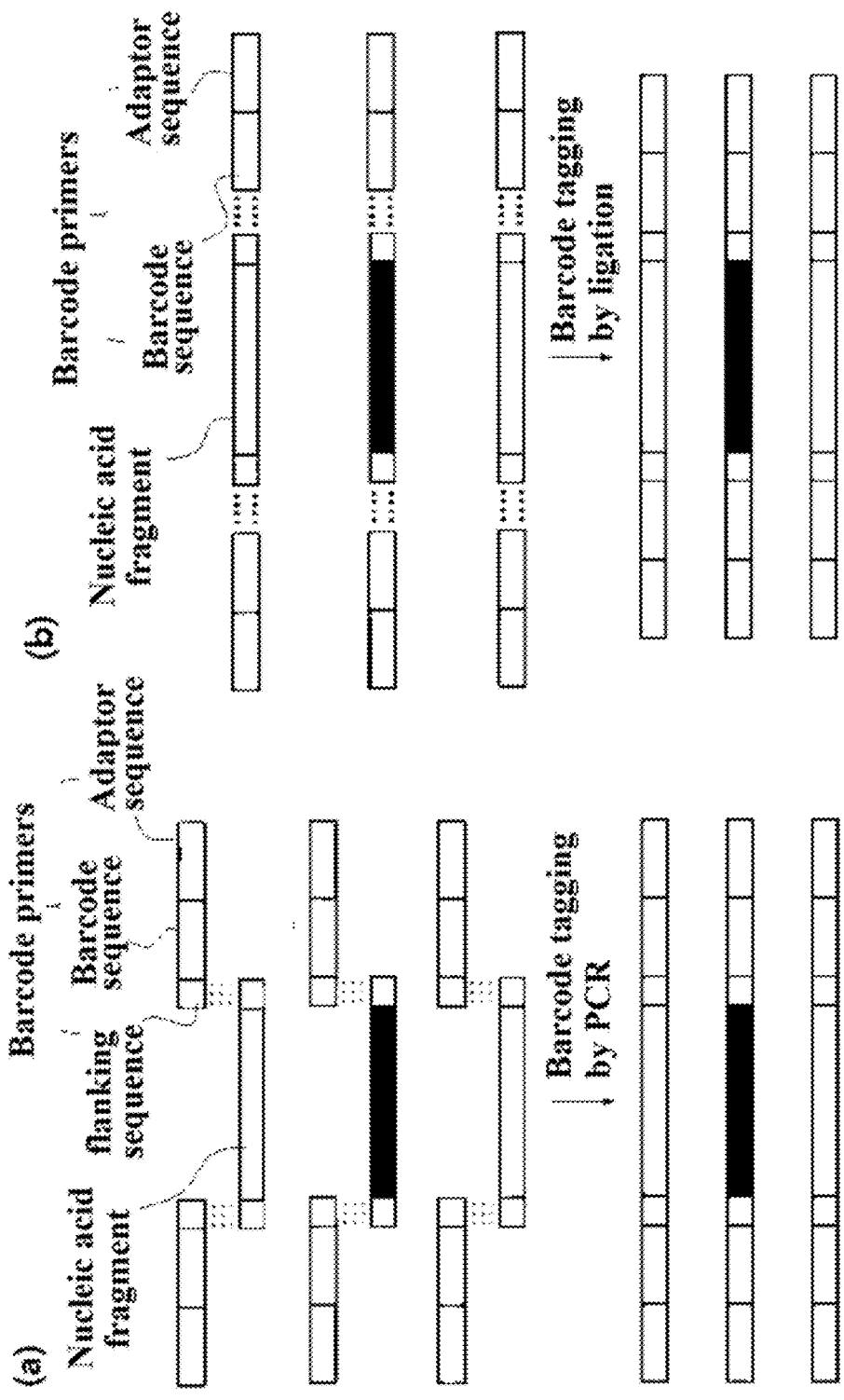
FIG. 5 illustrates two procedures for tagging nucleic acid fragments with barcode sequences according to embodiments of the present disclosure.

FIG. 5 illustrates two procedures for tagging nucleic acid fragments with barcode sequences according to embodiments of the present disclosure. (a) and (b) of FIG. 5 illustrate barcode tagging procedures by PCR and by ligation, respectively.

In step S130, the sequences of the nucleic acid fragments tagged with the barcode sequences are validated. Parallel sequencing is preferably used to validate the sequences of the tagged nucleic acid fragments. As a result, the sequences of the tagged nucleic acid fragments, together with the tagging barcode sequences, can be validated.

According to one embodiment of the present disclosure, the parallel sequencing or high-throughput sequencing is carried out by a suitable method well known in the art, for example, using a Roche-454 sequencing system or a high-throughput sequencing system with a read length of 100 bp or more.

According to one embodiment of the present disclosure, sequencing adaptor sequences may be further added to the barcode sequences. Sequences containing the barcode sequences added to the nucleic acid fragments are herein referred to as "barcode primers" for convenience.

The term "adaptor sequences" as used herein refers to sequences that enable high-throughput sequencing analysis of the nucleic acid fragments. For example, the adaptor sequences includes all commercially available sequences for 454-sequencing used in the present disclosure. Examples of preferred adaptor sequences include, but are not limited to, adaptor sequences of Roche-454 sequencing platforms and adaptor sequences of other next-generation sequencing technologies.

The term "generic flanking sequences" as used herein refers to base sequences that are added to both ends of the oligonucleotides to selectively amplify particular oligonucleotides among the pool of oligonucleotides. The base sequences added to the 5'-ends of different oligonucleotides necessary for assembly into target nucleic acid molecules are identical to each other, and the base sequences added to the 3'-ends of different oligonucleotides are identical to each other.

According to one embodiment of the present disclosure, an amplification procedure using the primers bound to the adaptor sequences may be performed using the tagged nucleic acid fragments as templates for sequence validation.

The barcode sequences are not limited to particular lengths and are, for example, 5-300 bp, preferably 10-100 bp, more preferably 12-40 bp, even more preferably 15-30 bp in length taking into consideration the sequencing performance on the entire sequences including the nucleic acid fragments. This numerical range may vary with the advance of sequencing technologies. For example, when the poly-N degenerate-barcode sequences are 20 bp long, $4^{20}$ kinds of the barcode sequences are possible.

The barcode primers may contain, for example, from the 5' to 3' direction, 454-adaptor sequences, poly-N degenerate-barcode sequences, restriction enzyme digestion sequences, and generic flanking sequences. The primers for amplification may be designed to bind to the 454-adaptor sequences.

The sequence validation enables identification of error-free nucleic acid fragments among the nucleic acid fragments and the barcode sequences added thereto.

On the other hand, the restriction enzyme digestion sequences contained in the barcode primers serve to remove the sequencing adaptor sequences of the nucleic acid fragments. The reason for this removal is because the presence of the adaptor sequences hinders subsequent assembly of the nucleic acid fragments because of attached beads in sequencing analysis.

In step S140, desired nucleic acid fragments are recovered among the sequence-validated nucleic acid fragments using the barcode sequences. The validation of the sequences of the desired nucleic acid fragments and the tagging barcode sequences by sequencing in the previous step enables recovery of the desired nucleic acid fragments using the barcode sequences. Specifically, the recovery step may be carried out by selectively amplifying the desired nucleic acid fragments with primers corresponding to the barcode sequences and recovering the amplified nucleic acid fragments. Alternatively, the recovery step may be carried out by selectively hybridizing the desired nucleic acid fragments with oligonucleotides corresponding to the barcode sequences and recovering the hybridized nucleic acid fragments. For example, the desired nucleic acid fragments may be error-free nucleic acid fragments.

The desired nucleic acid fragments may be recovered using a computer program. Specifically, the sequences of the nucleic acid fragments are imaginarily assembled using a computer program and are compared with the complete sequence of desired target nucleic acid molecules. Thereafter, primers synthesized based on the most optimized information on sequences flanking DNA fragments or primers hybridizing therewith can be used to recover the desired nucleic acid fragments.

According to one embodiment of the present disclosure, the computer program may be any of those known in the art. Examples of more preferred computer programs include in-house Python programs and programs constructed using Perl, C, C++ or other programming languages.

According to one embodiment of the present disclosure, the computer program is used to synthesize sequences complementary to the selected barcode sequences into oligos. Next, only error-free fragments capable of optimizing the synthesis of target DNA are recovered among the nucleic acid fragments (i.e. mixtures of erroneous fragments and error-free fragments) by amplification (PCR) or hybridization using the synthesized barcode oligos. Examples of methods for the recovery of error-free fragments using the synthesized barcode sequences include, but are not limited to, DNA capture methods using microchips and hybridization methods for recovering desired error-free fragments by attaching desired barcode sequences to biotinylated beads or magnetic beads, in addition to PCR.

According to one embodiment of the present disclosure, when the nucleic acid fragments are provided by shotgun assembly, the length of the error-free barcoded nucleic acid fragments may be 200 bp or more. When a next-generation sequencing system capable of analyzing DNA with 1,000 bp or more is used, the error-free barcoded nucleic acid fragments may be 1,000 bp or more in length. More preferably, the error-free barcoded nucleic acid fragments are from about 200 bp to about 10 kb or more in length.

In step S150, recovered nucleic acid fragments can be assembled to form long nucleic acid molecules.

According to one embodiment of the present disclosure, the target nucleic acid molecules prepared by the present disclosure include, but are not limited to, target genes, target gene clusters, target genomes, and natural or synthetic nucleic acid molecules.

The term "target gene cluster" or "target genome" as used herein refers to a cluster or genome that includes at least two genes encoding a desired target (gene). The cluster or genome may include cluster or genome regions capable of generating two or more gene products (e.g., genome regions including one or more multiple splicing products of the same gene).

According to one embodiment of the present disclosure, a target gene cluster or target genome that can be synthesized by the method of the present disclosure may have a length of about 10 kb or longer. For example, the target gene cluster or target genome may include a penicillin biosynthetic gene cluster DNA sequence (11,376 bp) from *Penicillium chrysogenum*, and the penicillin biosynthetic gene cluster may include pcbAB, pcbC, and penDE genes.

The term "natural or synthetic nucleic acid molecules" as used herein is intended to include DNA (gDNA and cDNA) and RNA molecules, and nucleotides as basic units of the nucleic acid molecules include not only natural nucleotides but also analogues having modified sugar or base moieties (Scheit, *Nucleotide Analogs*, John Wiley, New York (1980); Uhlman and Peyman, *Chemical Reviews*, 90:543-584 (1990)).

Figure 6:
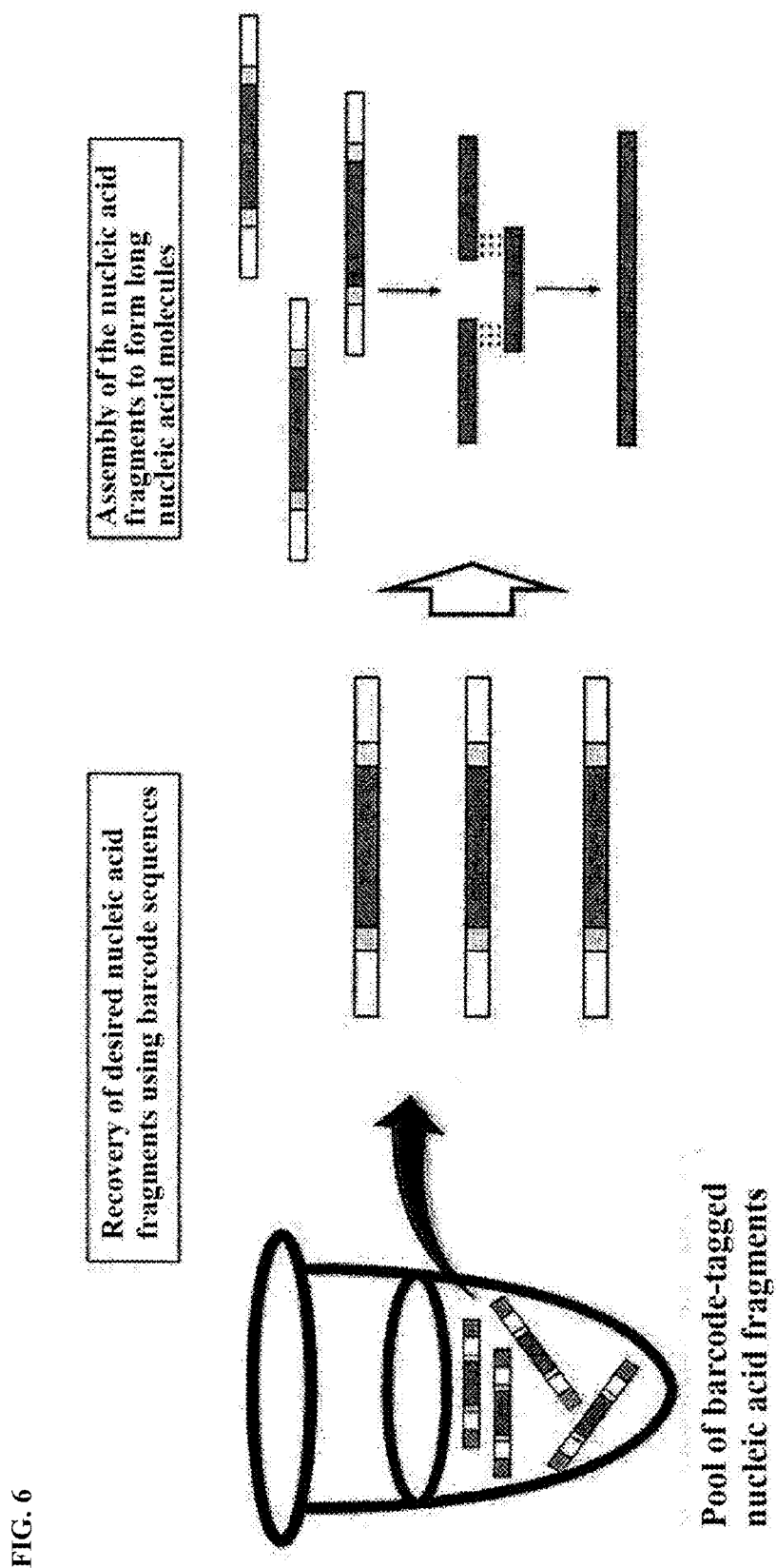
FIG. 6 illustrates a procedure for recovering desired nucleic acid fragments from a pool of barcode-tagged nucleic acid fragments and assembling the recovered nucleic acid fragments to form long nucleic acid molecules.

FIG. 6 illustrates a procedure for recovering the desired nucleic acid fragments from the pool of the barcode-tagged nucleic acid fragments and assembling the recovered nucleic acid fragments to form long nucleic acid molecules. According to one embodiment of the present disclosure, the nucleic acid molecules may be prepared by a method including the following steps.

Nucleic acid fragments constituting at least a portion of the complete sequence of a target nucleic acid are provided (step (a)). The size of the nucleic acid fragments provided in step (a) may be from 20 to 300 bp.

The nucleic acid fragments are assembled to synthesize intermediates having sizes whose sequences can be validated by a parallel sequencing technology (step (b)). The size of the intermediates is not particularly limited and may be, for example, from 50 to 3,000 bp. The intermediates may be increased to a desired size with the advance of parallel sequencing technologies such as next-generation sequencing technology. The intermediates may be synthesized by various synthesis processes, including hierarchical synthesis or random synthesis (shotgun synthesis).

The intermediates are tagged with barcode sequences (step (c)). Preferably, sequencing adaptor sequences are added to the barcode sequences for sequence validation.

The sequences of the intermediates tagged with the barcode sequences are validated (step (d)). The sequence validation of the intermediates tagged in step (d) may be performed by a parallel sequencing technology. The method may further include amplifying the tagged nucleic acid fragments using the sequencing adaptor sequences between steps (c) and (d).

Desired intermediates are recovered among the sequence-validated intermediates using the barcode sequences (step (e)). The desired intermediates may have error-free sequences.

The recovered intermediates are assembled to form long nucleic acid molecules (step (f)). The size of the long nucleic acid molecules may be 1,000 bp or more.

Figure 7:
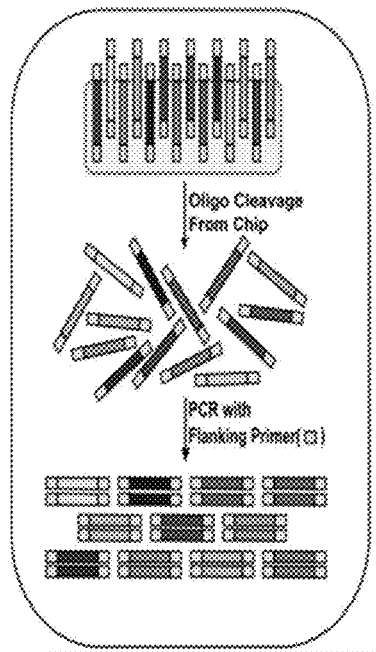
FIG. 7 schematically illustrates simultaneous utilization of a number of oligonucleotides for shotgun synthesis to obtain large target DNA molecules.
Figure 7:
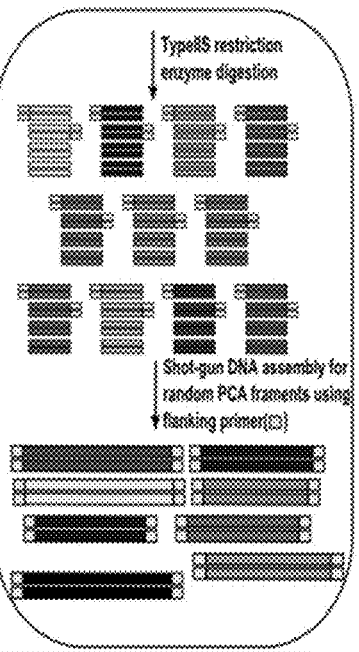
Figure 7:
Figure 7:
Figure 7:
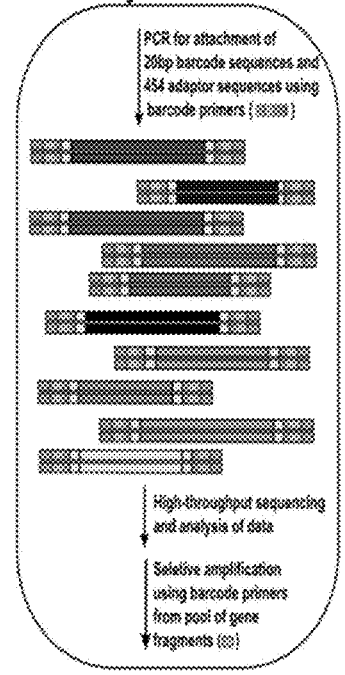
Figure 7:
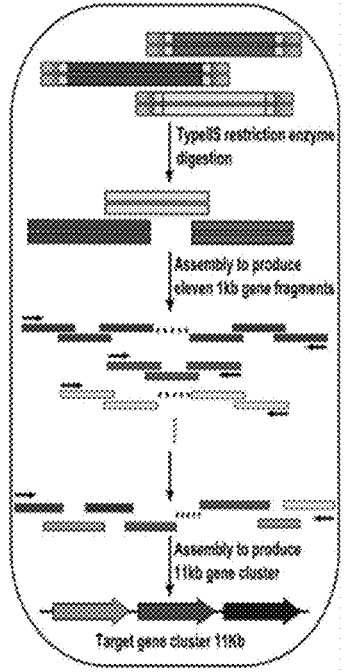

FIG. 7 schematically illustrates simultaneous utilization of a number of oligonucleotides for shotgun synthesis to obtain large target DNA molecules. Shotgun synthesis using about 200 oligonucleotides may cause random fragments with varying sizes of 100 bp (monomeric forms of oligonucleotides) to 1,000 bp. The assembly fragments in the form of intermediates are effectively barcoded by degenerate primers for high-throughput sequencing. The sequence-validated fragments are used in the subsequent assembly process.

Referring to FIG. 7, first, oligonucleotides are prepared from chips. The oligonucleotides are designed to have flanking sequences with Type IIS restriction enzyme sites (EarI or BtsI), and are synthesized on a DNA microarray. After oligonucleotides are cleaved from the chips, PCR amplification is carried out to increase the concentration of the oligonucleotides. The amplified oligonucleotides are cleaved using Type IIS restriction enzymes to remove the flanking sequences. Because the efficiency of the restriction enzymes is less than 100%, there are still uncut flanking sequences. Shotgun DNA assembly PCR using the remaining uncut flanking sequences is carried out to synthesize random fragments of the target genes. The sequences of the synthesized random fragments are analyzed by high-throughput sequencing technology. To this end, the synthesized fragments are tagged with the barcode primers using PCR. The PCR products are sequenced by 454 high-throughput sequencing and analyzed using an in-house Python program to identify error-free gene fragments and connected barcode sequences. To recover the error-free gene fragments, PCR is carried out from the pool of shotgun-assembled target gene fragments using barcode primer sequences. After removing the degenerate barcode sequences and flanking sequences from the recovered fragments by Type IIS restriction enzyme digestion, the error-free shotgun synthesis fragments are finally assembled into the full-length target gene.

Figure 8:
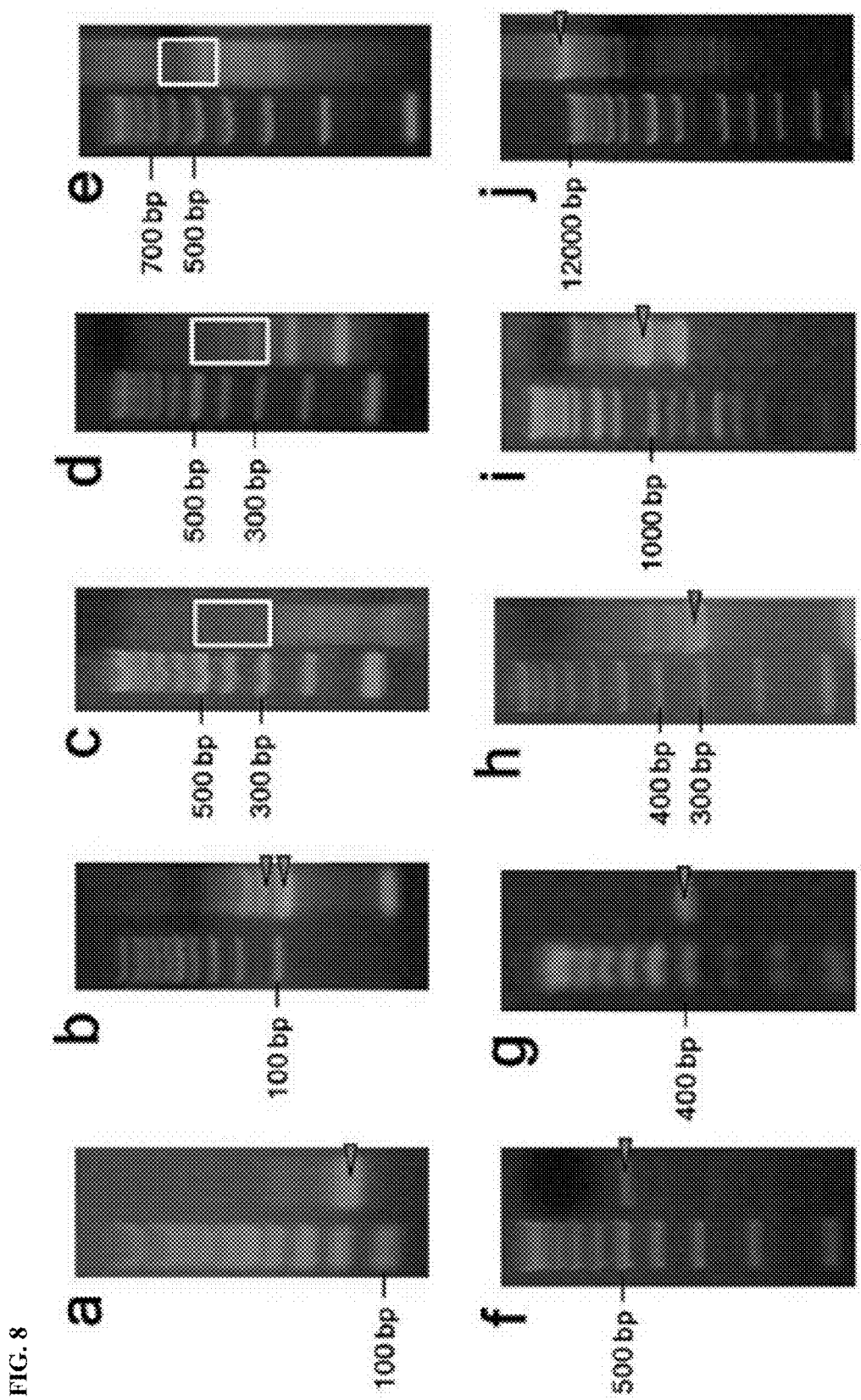
FIG. 8 shows PCR products produced in individual steps.

FIG. 8 shows PCR products produced in the individual steps. FIG. 8a shows PCR products produced by second round PCR using chip flanking primers. FIG. 8b shows results obtained after electrophoresis of the PCR products cleaved by Type IIS restriction enzyme in 4% agarose gel. The indicated two bands were excised and gel-purified together. FIG. 8c shows smear bands of PCR products assembled randomly using the Pen gene cluster fragments of FIG. 8b, which were amplified by chip flanking primers. The smear bands were excised and gel-purified. FIG. 8d shows PCR products obtained by re-amplification of the bands in the white box of FIG. 8c using chip flanking primers. The bands in the white box were excised and gel-purified. FIG. 8e shows smear bands obtained from PCR using barcode primers. The smear bands in the white box were excised and gel-purified. FIG. 8f shows products obtained by 100-fold dilution of the products obtained from the bands of FIG. 8e and amplification of the diluted products using 454-adaptor primers. If the concentration of the products obtained from the bands of FIG. 8e is excessively high, PCR is not conducted properly. The amplification products were excised, purified, diluted, cloned into TOPO vector, and submitted for Roche-454 sequencing. Daughter fragment 11-d produced by PCR was re-amplified with primers containing degenerate sequences. The resulting PCR amplification products are shown in FIG. 8g.

FIG. 8h shows three bands obtained by excising the bands shown in FIG. 8g with a Type IIS restriction enzyme. FIG. 8i shows Fragment 11 prepared by assembly of the bands shown in FIG. 8h and other daughter fragments. Fragment 11 is indicated by the arrow. FIG. 8j shows a final gene cluster obtained after assembly of 11 fragments.

Figure 9:
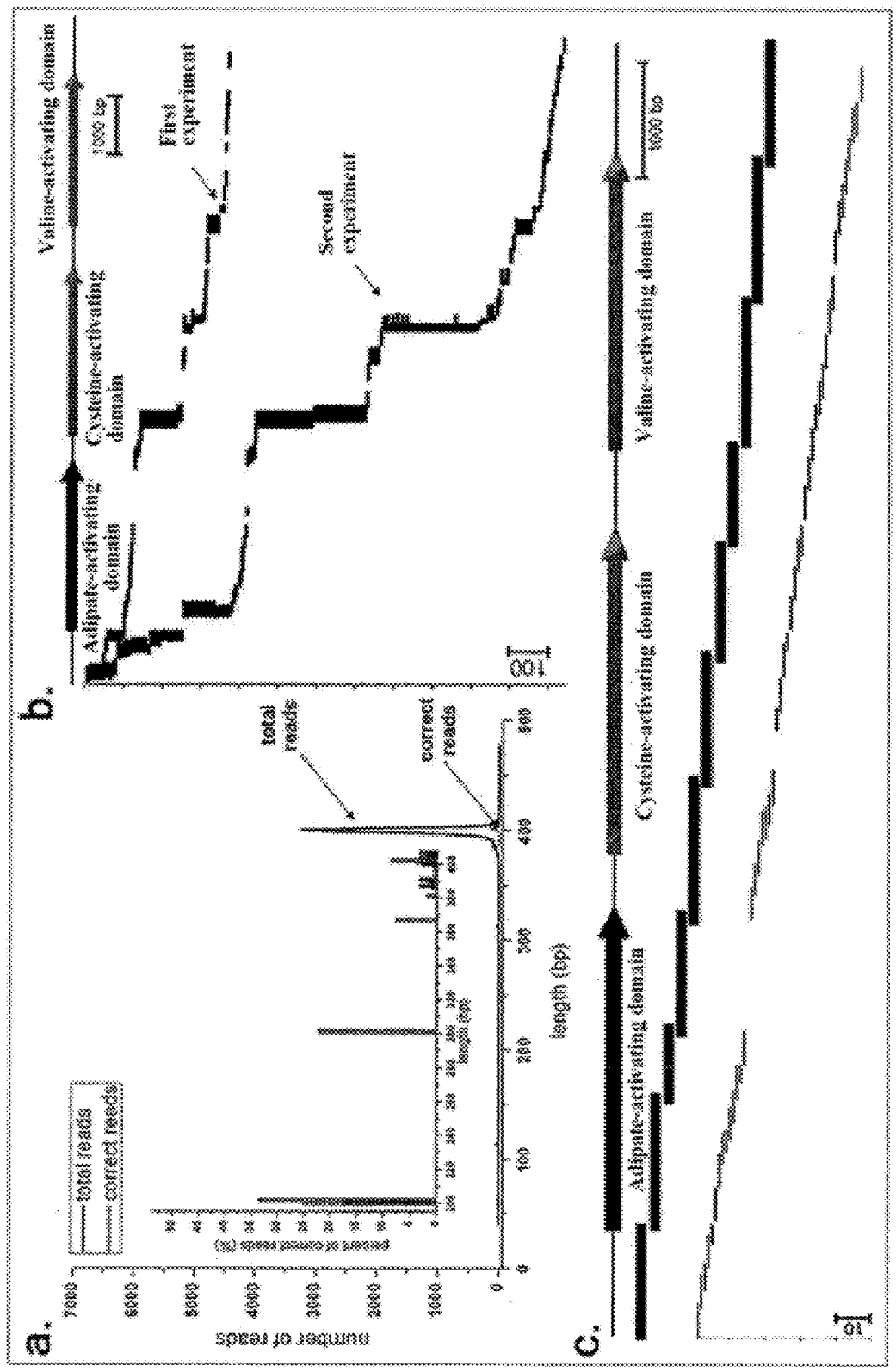
FIG. 9 shows computational analysis of 454 sequencing data from shotgun synthesis.

FIG. 9 shows computational analysis of 454 sequencing data from shotgun synthesis. FIG. 9a shows the number of 454 sequencing reads versus the length of the gene fragments. The upper and lower lines show the number of total 454 sequencing reads (total reads) and the error-free fragment reads (correct reads), respectively. The most abundant and correct reads have a length of 400 bp (they are typically 300 bp without barcode flanking regions). The inset in FIG. 9a shows that the percentage of error-free gene fragments tends to decrease as the length of the gene fragments increases. FIG. 9b shows computational analysis of two independent experiments (first and second experiments), and graphically aligned error-free gene fragments after the removal of the flanking barcode sequences. The first, second and third arrows on top of the figure represent clusters of genes (adipate-activating, cysteine-activating and valine-activating domains, respectively). The y-axis indicates the number of error-free gene fragments corresponding to various parts of the target gene. The scale bars at the bottom left and top right indicate 100 bp fragments and 1,000 bp base pairs, respectively. FIG. 9c shows the results of hierarchical shotgun synthesis. Optimized and selected gene fragments (~300 bp) were assembled into 1,000 bp gene fragments, which were then continuously assembled to synthesize the target gene (penicillin synthetic gene cluster (N-(5-amino-5-carboxypentanoyl)-L-cysteinyl-D-valine synthase); ~11.4 kb).

The foregoing embodiments of the present disclosure offer the following advantages. The method of the present disclosure enables scalable synthesis of large target nucleic acid molecules in a more economical and efficient manner. According to the method of the present disclosure, amplification products containing the sequence of a target nucleic acid are prepared using an elaborately designed target oligonucleotide pool, 300-500 bp error-free shotgun assembly fragments are selectively recovered from the amplification products using barcode sequences, and larger target nucleic acid molecules (e.g., ≥~10 kb) are synthesized using the error-free shotgun assembly fragments. In addition, the method of the present disclosure enables gene synthesis at lower cost than conventional methods using resin-based oligonucleotides. Therefore, the present disclosure can be applied as a novel method for the synthesis of large target nucleic acid molecules and thus provides very excellent means that can considerably reduce gene synthesis cost.

The present disclosure will be explained in more detail with reference to the following examples. These examples are provided for illustrative purposes only and it will be obvious to those skilled in the art that are not intended to limit the scope of the present disclosure in accordance with the subject matter of the present disclosure.

EXAMPLES

Materials

AccuPrep™ gel purification kits for DNA purification and AccuPrep™ plasmid extraction kits for plasmid extraction were purchased from Bioneer (Korea). Pfu polymerase pre-mix and Taq polymerase pre-mix were purchased from Solgent (Korea). Phusion polymerase pre-mix, restriction enzymes [EarI (20,000 U/ml) and BtsI (10,000 U/ml)], NEB buffer 4(10) and competent cells (C-2566) were purchased from New England Biolabs (NEB) (USA). TOP Cloner™ Blunt core kits (6 TOP cloner buffer, sterile water, pTop blunt V2) were purchased from Enzynomics (Korea). Microchip oligonucleotides and primers were purchased from Agilent (USA) and Macrogen (Korea), respectively. Sanger sequencing and Roche-454 sequencing were requested to Macrogene (Korea).

Target Penicillin Biosynthetic Gene Cluster and Oligonucleotide Sequence Design

Penicillin biosynthetic gene cluster (N-(5-amino-5-carboxypentanoyl)-L-cysteinyl-D-valine synthase) DNA sequence (11,376 bp) from *Penicillium chrysogenum* was chosen as a synthetic model. A codon-optimized penicillin biosynthetic gene cluster sequence was designed using the web-based program Optimizer (Puigb, P. et al., 2007). Twenty-four nucleotides (5-GCAGAGTAAAGACCGTG-CACTTAT-3 SEQ ID NO: 1) were added to the microchip oligonucleotides.

Each Agilent chip oligonucleotide was 150 nucleotides in length and consisted of flanking sequences and target DNA sequences. Oligonucleotides (114 plus and 114 minus strands) for target DNA sequences were designed in such a way that upon annealing, complementary oligonucleotides contained overlapping regions for assembly. These 228 oligonucleotide sequences were flanked by generic PCR primer sequences.

Processing of Sub-Pools of Agilent Microchip Oligonucleotides

Lyophilized Agilent microchip oligonucleotides were suspended in 100 µl water. A higher concentration of the microchip oligonucleotide subpool (228 oligonucleotides targeting the penicillin biosynthetic gene cluster) was prepared using PCR amplification with flanking primers. The components included in each PCR reaction mixture were 8 µl water, 10 µl 2Pfu polymerase pre-mix, 0.5 µl cleaved oligonucleotide pool, and 1 µl 10 µM forward and reverse primers. The first PCR reaction was performed as follows: (a) a pre-denaturation step at 95° C. for 3 min; (b) a 20-cycle PCR step, each cycle consisting of 95° C. for 30 s, 55° C. for 30 s, and 72° C. for 1 min; and (c) a final elongation step at 72° C. for 10 min. Thereafter, to amplify the oligos, the second PCR reaction was performed on the PCR products amplified by the first PCR reaction. For the PCR, the following reagents were used: 18 µl water, 25 µl 2 Pfu polymerase pre-mix, 3 µl of the first PCR products, and 2 µl 10 µM orward and reverse primers. The second PCR conditions were the same as for the first PCR reaction with the exception of the number of reaction cycles (i.e. 12). After verification of the desired products by 4% agarose gel electrophoresis, restriction enzyme digestion was carried out as follows: when EarI was used, 2.5 µl EarI, 5 µl NEB buffer, 0.5 µl 100×BSA and 50 µl PCR products were mixed, followed by digestion at 37° C. for 3 h; and when BtsI was used, 2.5 µl BtsI, 5 µl NEB buffer, 0.5 µl 100×BSA and 50 µl PCR products were mixed, followed by digestion at 55° C. for 3 h. The restriction digest products were electrophoresed through 4% agarose gels and gel-purified.

Shotgun Assembly

The gel-purified products were assembled using the first round shotgun assembly PCR. For the PCR, the following reagents were used: 20 µl Pfu polymerase pre-mix and 20 µl purified products (the sub-pool of 228 microchip oligonucleotides). The PCR conditions were as follows: a pre-denaturation step at 95° C. for 3 min; (b) a 36-cycle PCR step, each cycle consisting of 95° C. for 30 s, 60° C. for 30 s, and 72° C. for 1 min; and (c) a final elongation step at 72° C. for 10 min. After the PCR products were electrophoresed through an agarose gel (1.5%), gel regions (target size =~350 bp) of 300-500 bp were excised.

Processing of the Shotgun Assembly Products by Barcoding and 454 Sequencing

The detailed procedure is illustrated in FIG. 7. The gel-purified shotgun assembly fragments were amplified using flanking primers for PCR. For the PCR, the following reagents were used: 10 µl water, 25 µl Pfu polymerase pre-mix, 10 µl of the purified shotgun assembly fragments, and 2.5 µM forward and reverse primers. The PCR conditions were as follows: (a) a pre-denaturation step at 95° C. for 3 min; (b) a 18-cycle PCR step, each cycle consisting of 95° C. for 30 s, 55° C. for 30 s, and 72° C. for 1 min; and (c) a final elongation step at 72° C. for 10 min. As a result, bands between 300 and 450 bp were excised and purified using an AccuPrep™ DNA purification kit (Bioneer, Korea).

The fragments were barcoded by a primer pair that consisted of, from the 5' to 3' direction, a 454 DNA sequencing-adaptor sequence, a 454 high-throughput sequencing key sequence (e.g., 5-TCAG-3), a 20-mer degenerate primer (i.e. made of poly N sites), an EcoP15I Type IIS restriction enzyme site, and the flanking primer sequences. The EarI or BtsI site was located at the 3' end of the flanking sequence of the chip oligonucleotides. The EcoP15I site was introduced into the PCR amplification procedure for shotgun assembly of the fragments using the barcoded primers. For the PCR, the following reagents were used: 6 µl water, 20 µl 2 Pfu polymerase pre-mix, 10 µl the assembled gene fragment pool, and 2 µl forward and reverse barcode primers. The PCR conditions were as follows: (a) a pre-denaturation step at 95° C. for 3 min; (b) a 18-cycle PCR step, each cycle consisting of 95° C. for 30 s, 55° C. for 30 s, and 72° C. for 1 min; and (c) a final elongation step at 72° C. for 10 min. After the PCR products were electrophoresed through an agarose gel (1.5%), the gel was excised to purify assembled fragments (450-600 bp). These gel-purified fragments were diluted 100-fold and the diluted products were then used for a final PCR amplification step involving 454 DNA sequencing-adaptor primers (Macrogene, Korea). For the PCR, the following reagents were used: 17.5 µl water, 25 µl Pfu, 2.5 µl of the 100-fold diluted gel-purified products and 2.5 µl forward and reverse primers. Eight replicate 20 µl PCR reaction products. The PCR reaction conditions were as follows: (a) a pre-denaturation step at 95° C. for 3 min; (b) a 25-cycle PCR step, each cycle consisting of 95° C. for 30 s, 71° C. for 30 s, and 72° C. for 1 min; and (c) a final elongation step at 72° C. for 10 min. Thereafter, the PCR products were electrophoresed through an agarose gel (1.5%), followed by gel purification (450-500 bp). The eight replicates were pooled prior to 454 sequencing.

Prior to 454 sequencing, cloning of the barcoded target gene fragments was performed, and several colonies were selected and submitted for Sanger sequencing evaluation. Gel-purified and barcoded products were cloned into the TOPO vector using the TOP Cloner™ Blunt core kit (Enzynomics, Korea). Competent cells derived from C2566 (New England Biolabs, USA), an *Escherichia coli* strain, were then transformed with the cloned products. After overnight growth on agar plates at 37° C., several colonies were chosen for colony PCR using M13F-pUC and M13R-pUC universal primer pairs. After confirmation of the presence of inserted DNA, Sanger sequencing was conducted prior to Roche-454 sequencing. Thereafter, the sequences of the gene fragments and the barcode primer sequences were validated using the Lasergene program (DNAstar, Madison, Wis.). After verification of the sequences, the pool of assembly PCR products was selected for Roche-454 high-throughput sequencing. The sequencing data were analyzed using an in-house Python program, and error-free gene fragments were selected.

Algorithm of In-house Python Program to Analyze the 454 High-throughput Sequencing The primary task of the computer program was to select error-free shotgun assembly samples for subsequent assembly. The 454 sequencing read results (454 reads) were aligned to the target penicillin biosynthetic gene cluster sequence using the in-house Python programming language. DNA fragments with desired restriction enzyme sites (i.e. EcoP15I and either, EarI or BtsI sites) at both ends of the read were selected based on the sequencing data with a high quality score (Phred-like consensus quality >30, which corresponded to a base call accuracy >99.9%). Flanking sequences containing the enzyme site were eliminated from the processed gene fragments, and the flanking sequence-removed internal sequences were aligned to the target penicillin biosynthetic gene cluster sequence. When these internal sequences matched perfectly with the reference sequence, the aligned sequences were graphically listed along with their target gene cluster sequence (FIG. 9b). Subsequently, the program determined the optimal set of internal sequences that overlapped by more than 15 bp with other fragments necessary for subsequent assembly.

These selected gene fragments were recombined into the complete target gene (FIG. 9c). The Python scripts used for the analysis are available upon request.

Synthesis of the Target Gene Cluster from the Target Assembly Products

Amplification of the Desired Shotgun Assembly Products and Elimination of the Flanking Sequences from the Shotgun Assembly Products As described above, an in-house Python program was used to select optimum sets of shotgun assembly products. These overlapping error-free DNA fragments were selectively amplified from shotgun assembly DNA mixtures using selected barcode primer pairs. For the PCR, the following reagents were used: 8 µl water, 10 µl Phusion polymerase pre-mix, 1 µl forward and reverse barcode primers, and 1 µl of the shotgun assembly DNA mixture.

The PCR conditions were as follows: (a) a pre-denaturation step at 95° C. for 3 min; (b) a 30-cycle PCR step, each cycle consisting of 95° C. for 30 s, 60° C. for 30 s, and 72° C. for 1 min; and (c) a final elongation step at 72° C. for 10 min. The barcode primers are listed in Table 1.

TABLE 1

Sequences of degenerate primers used for PCR recovery of error-free fragments

| Fragment (Daughter fragment) | CODE | Restriction enzyme used | Primer sequence Forward direction (5' → 3') | Primer sequence Reverse direction (5' → 3') | Nested PCR Primer sequence Forward direction (5' → 3') | Nested PCR Primer sequence Reverse direction (5' → 3') |
|---|---|---|---|---|---|---|
| 1-a | G2JQR 9I07H3 VM7 | EcoP15I from BtsI reaction pool | CTATTTGATGTTC GTAGTTCCAG (SEQ ID NO: 2) | AGCCTTTTCAAAGCG AAAG (SEQ ID NO: 3) | | |
| 1-b | G2JQR 9I07H5 WCJ | EcoP15I from EarI reaction pool | ATCTATTAGGTCA TAGTAGGCAG (SEQ ID NO: 4) | CATGCAGAGGAAAC CATAAA (SEQ ID NO: 5) | | |
| 1-c | G2JQR 9I07H3 8JU | EarI | TGCTATTCTTTCT GCCTTTTCAG (SEQ ID NO: 6) | GAATGTTTGTTGCGT TTCCA (SEQ ID NO: 7) | | |
| 1-d | G2JQR 9I07IK M12 | EcoP15I from EarI pool | TCGAGCTCAATA GTTTTTTCAG (SEQ ID NO: 8) | TTTATGATTGCATTC AGCAGCAG (SEQ ID NO: 9) | | |
| 1-e | G2JQR 9I06HC 8AH | EarI | TTACTCCATTTTG CACTCTCAG (SEQ ID NO: 10) | ATTCTTTGGCCTTTGT TGACAG (SEQ ID NO: 11) | | |
| 2-a | G2JQR 9I06HC ZWA | Nest PCR from BtsI pool | TTAGTTTCAACAT GTATATACAGCA GC (SEQ ID NO: 12) | ATGTGTATATTCGAC ACTTTCAGC (SEQ ID NO: 13) | GTGAATATCCGT CTAGCAAGC (SEQ ID NO: 14) | CAGTTCACGTTCGTCGCA CACCAC (SEQ ID NO: 15) |
| 2-b | G2JQR 9I06GY Z2I | EcoP15I from BtsI pool | CTATTTTCAGTGT GCCTTT (SEQ ID NO: 16) | TCCTAAGTTGATGAA ACTTT (SEQ ID NO: 17) | | |
| 2-c | G2JQR 9I06GU X19 | EarI | TATCTGGTAGGA GGGGTT (SEQ ID NO: 18) | TAGAACTGGCAATGA CGCTG (SEQ ID NO: 19) | | |
| 2-d | G2JQR 9I06G2 U2M | EarI | TTCTGTTTGTCTT AAATGCG (SEQ ID NO: 20) | TACCGTTTTTAAGAT TGCGT (SEQ ID NO: 21) | | |
| 2-e | G2JQR 9I07IH 5UA | EcoP15I from BtsI pool | CTGAAATTCATTT ATGTTTG (SEQ ID NO: 22) | CTATGGGGTACCTTT TTG (SEQ ID NO: 23) | | |
| 2-f | G2JQR 9I06G0 10D | EcoP15I from EarI pool | ATATTCGAGCGT ATGTATTA (SEQ ID NO: 24) | AAGTGATTGTTTACA GTCTC (SEQ ID NO: 25) | | |
| 2-g | G2JQR 9I07IK Z70 | EcoP15I from EarI pool | TCATTTCGAGAA AAGGCCGA (SEQ ID NO: 26) | GGGTTCTTTCCCTTAT TTTG (SEQ ID NO: 27) | | |
| 3-a | G2JQR 9I06HH 7SE | EarI | AACGAGGATATA CAAATATA (SEQ ID NO: 28) | AAGTGTTGAGAGTGG TATAT (SEQ ID NO: 29) | | |
| 3-b | G2JQR 9I07H5 FTG | EarI | ATGGAGCTTTTAT GTGGTTA (SEQ ID NO: 30) | AATTGTCTAGTTTCG TTGTT (SEQ ID NO: 31) | | |

TABLE 1-continued

Sequences of degenerate primers used for PCR recovery of error-free fragments

| Fragment (Daughter fragment) | CODE | Restriction enzyme used | Primer sequence Forward direction (5' → 3') | Primer sequence Reverse direction (5' → 3') | Nested PCR Primer sequence Forward direction (5' → 3') | Nested PCR Primer sequence Reverse direction (5' → 3') |
| --- | --- | --- | --- | --- | --- | --- |
| 3-c | G2JQR9I06GWSUY | EcoP15I from BtsI pool | TGTTGGTTGTTCAATGGAGT (SEQ ID NO: 32) | ATACTTGTTTCAATTTTGTCCAGC (SEQ ID NO: 33) | | |
| 4-a | G2JQR9I06GX0BH | Nest PCR from EarI pool | TATTTTTTTCCAATTTTTTTACAGC (SEQ ID NO: 34) | ATCCTCTGCTATTCTGTTGC (SEQ ID NO: 35) | ACCTGCATCCAGCTGATTGCGCGTATCCGTCAGCGTCAGCGTTTGTCTGTGTCTATCTCTGTG (SEQ ID NO: 36) | GGGAAAGGGTGGTGTTGTAA (SEQ ID NO: 37) |
| 4-b | G2JQR9I07H7Z2P | Nest PCR from EarI pool | CTAATTTGAATGCAGTCCGT (SEQ ID NO: 38) | ACATTACCTTTGGAAAAAACC (SEQ ID NO: 39) | CATGGAACAAAGTGATGCTT (SEQ ID NO: 40) | TCCAGCAGCTGGAAGACTT (SEQ ID NO: 41) |
| 4-c | G2JQR9I06HCPB7 | Nest PCR from EarI pool | TTAAGTATGATTAATGCTGTCA (SEQ ID NO: 42) | CGATATTGTTCATAATATGTCAG (SEQ ID NO: 43) | TCTGCGCTTCTCTTGGGAA (SEQ ID NO: 44) | GGCGTAAATCTTCCAGTTTA (SEQ ID NO: 45) |
| 4-d | G2JQR9I06GS219 | Nest PCR from EarI pool | GTGGTATGCACGTTGGTC (SEQ ID NO: 46) | TATGTGAGTGATCNCCGTTTCAG (SEQ ID NO: 47) | TGGTGCAGTAGAAGACCGTA (SEQ ID NO: 48) | TTTTTCGAACAGAAGCGGTA (SEQ ID NO: 49) |
| 4-e | G2JQR9I06HA060 | Nest PCR from BtsI pool | ATTACTTAGGGTATTGCGTTC (SEQ ID NO: 50) | AGACCTTCAGTCTTTGCGAT (SEQ ID NO: 51) | CGTTTACCTGATCAAACACAGC (SEQ ID NO: 52) | AGCTGCACTTTATAGCGG (SEQ ID NO: 53) |
| 4-f | G2JQR9I07IGZCH | Nest PCR from EarI pool | ATAGCGTTATTAATTTCTGTCAG (SEQ ID NO: 54) | ATAGTTATTCGGCTAGTCCT (SEQ ID NO: 55) | TGCTCTGTTAAACGAACGCA (SEQ ID NO: 56) | TTGCGACCAGAAATAGTGGTG (SEQ ID NO: 57) |
| 5-a | G2JQR9I07ILSL3 | EcoP15I from BtsI pool | TCATAGAGGAGGTGCTATGG (SEQ ID NO: 58) | CGGATCGTTATTGACTGTT (SEQ ID NO: 59) | | |
| 5-b | G2JQR9I07IMJ1B | EcoP15I from EarI pool | GATATTTCGCGGTTCTGTTG (SEQ ID NO: 60) | AGGTAAAGGTTACTTAAACTCAG (SEQ ID NO: 61) | | |
| 5-c | G2JQR9I06GZ26W | EcoP15I from BtsI pool | TAGTCTTTGCCGGTTTATTA (SEQ ID NO: 62) | TTGCAAAGATTCTACAGA (SEQ ID NO: 63) | | |
| 5-d | G2JQR9I07IQTYC | EcoP15I from EarI pool | CTAAACTCTTTACTTCCTAT (SEQ ID NO: 64) | AGCTCGTTATTATGTGGCTT (SEQ ID NO: 65) | | |
| 5-e | G2JQR9I071BIHM | EcoP15I from EarI pool | TTATGAGAAATGTTTCACTG (SEQ ID NO: 66) | TAGAACACTATCAAATCTAG (SEQ ID NO: 67) | | |
| 5-f | G2JQR9I07IEGMC | EarI | TTTGTAATTTGACTCTGATGCAG (SEQ ID NO: 68) | TAGGAATCTTTTGACTTTTCACAG (SEQ ID NO: 69) | | |

TABLE 1-continued

Sequences of degenerate primers used for PCR recovery of error-free fragments

| Fragment (Daughter fragment) | CODE | Restriction enzyme used | Primer sequence Forward direction (5' → 3') | Primer sequence Reverse direction (5' → 3') | Nested PCR Primer sequence Forward direction (5' → 3') | Nested PCR Primer sequence Reverse direction (5' → 3') |
|---|---|---|---|---|---|---|
| 6-a | G2JQR 9I07IQ 369 | Nest PCR from EarI pool | TACTGGGAGCAA ACAATTCTCAG (SEQ ID NO: 70) | TTCGTCTGCTGTTTTC ACTCAG (SEQ ID NO: 71) | CTAACTACGTTT TCGATCACTTCG (SEQ ID NO: 72) | TTCACGGATTTTGTCGAA GAC (SEQ ID NO: 73) |
| 6-b | G2JQR 9I06HB BGB | Nest PCR from EarI pool | GTGGGATGGAAG CTCCTC (SEQ ID NO: 74) | TGTATTATGTCCTTTT TGCCAGC (SEQ ID NO: 75) | GCTTTCAGCGA GCCGGTCTTCGA CAAAATCCGTG AAACCTTCCAC GGTTTGGTTATC (SEQ ID NO: 76) | CAGGTACAGCTCACCCAC (SEQ ID NO: 77) |
| 6-c | G2JQR 9I07H1 GGH | EcoP15I from EarI pool | TGTTGGATATATA GGGTTAC (SEQ ID NO: 78) | CATGGGGATGATGTG TACTT (SEQ ID NO: 79) | | |
| 6-d | G2JQR 9I07HZ 198 | EcoP15I from EarI pool | AATTCACTCAGA ATAATTTT (SEQ ID NO: 80) | ATTTAGTTGGAATTA ATCTC (SEQ ID NO: 81) | | |
| 6-e | G2JQR 9I07IM S40 | EarI | CTACTGTTCGTTC CCAATTA (SEQ ID NO: 82) | TTGGTGTAAAACTGG GGGAA (SEQ ID NO: 83) | | |
| 7-a | G2JQR 9I07H0 2JG | EcoP15I from EarI pool | ATGTGTTATAGA AGTTGTTG (SEQ ID NO: 84) | TGACATGTGTTATCC CTGCT (SEQ ID NO: 85) | | |
| 7-b | G2JQR 9I06HG WSA | EarI | TTTCAGAAACTTA AACTTAC (SEQ ID NO: 86) | TTATAAGAAGTAATA GGAAT (SEQ ID NO: 87) | | |
| 7-c | G2JQR 9I07H8 TE4 | EarI | TATACAATCTATT GGTAATC (SEQ ID NO: 88) | TGGAATACTTTAATC CTTTC (SEQ ID NO: 89) | | |
| 7-d | G2JQR 9I07H7 QRT | EcoP15I from BtsI pool | TTACATGCTTTCG ACACATA (SEQ ID NO: 90) | TGTATAGTGTGAGGA TCTTT (SEQ ID NO: 91) | | |
| 7-e | G2JQR 9I07IE EEC | EcoP15I from BtsI pool | GTTAATTTCTGGG GATACGT (SEQ ID NO: 92) | TAACTCACGCTTTTT ATAAG (SEQ ID NO: 93) | | |
| 7-f | G2JQR 9I07IP GUX | EarI | TTCTTGTCACTCT CTTTATCCA (SEQ ID NO: 94) | TCTATCGGTTTTCGG GTTT (SEQ ID NO: 95) | | |
| 8-a | G2JQR 9I06G6 PRN | Nest PCR from BtsI pool | GAAGCACCTGTC TTATTTAACAG (SEQ ID NO: 96) | TGATCTTCCCGGGTA GGC (SEQ ID NO: 97) | GGTCGTTCTGCG TGTAGATAT (SEQ ID NO: 98) | CTGCAGCAGTTTCGTAAC TTC (SEQ ID NO: 99) |
| 8-b | G2JQR 9i07IR U8F | EcoP15I from EarI pool | TCATCCTATTACG ATGCCCG (SEQ ID NO: 100) | GCGTTGGAAGCTTTT TATTG (SEQ ID NO: 101) | | |

TABLE 1-continued

Sequences of degenerate primers used for PCR recovery of error-free fragments

| Fragment (Daughter fragment) | CODE | Restriction enzyme used | Primer sequence Forward direction (5' → 3') | Primer sequence Reverse direction (5' → 3') | Nested PCR Primer sequence Forward direction (5' → 3') | Nested PCR Primer sequence Reverse direction (5' → 3') |
|---|---|---|---|---|---|---|
| 8-c | G2JQR9I07IJA46 | EcoP15I from EarI pool | ATTTATAAGGACGGGCCAGC (SEQ ID NO: 102) | AAACGNTCCCCGTATTGGTA (SEQ ID NO: 103) | | |
| 8-d | G2JQR9I07IBAZE | EcoP15I from BtsI pool | TAATCTGATCGATGCTAGGA (SEQ ID NO: 104) | TTTTGATTCAATCCTCCTAA (SEQ ID NO: 105) | | |
| 9-a | G2JQR9I07IQ5TF | EarI | TTTCCTATTTCTTCATTGGCAG (SEQ ID NO: 106) | TTGCGATGGTTTACTTTGAT (SEQ ID NO: 107) | | |
| 9-b | G2JQR9I07IK8X6 | EarI | ATCATTGCACTTGTTGTTCG (SEQ ID NO: 108) | GGAAGGTTTTTTACTGATTT (SEQ ID NO: 109) | | |
| 9-c | G2JQR9I06HGDLG | EarI | TTATTCGTGGATTGGTGTTC (SEQ ID NO: 110) | ATTTTTCTAGGTTCTGATTA (SEQ ID NO: 111) | | |
| 9-d | G2JQR9I06G8AYI | EcoP15I from EarI pool | TGATTTCACCACTAAGTCT (SEQ ID NO: 112) | CCTCCTTTATTTCTCGTGC (SEQ ID NO: 113) | | |
| 9-e | G2JQR9I07ITPM8 | EarI | TAAAGTTATCATGTGCTACC (SEQ ID NO: 114) | TGTAAACCTATATTCATCTC (SEQ ID NO: 115) | | |
| 9-f | G2JQR9I06HH6RD | Nest PCR from EarI pool | GTTCATTGCATAATGCTTCTCAG (SEQ ID NO: 116) | TTAAAGCCCTTTACATCCAGCAGC (SEQ ID NO: 117) | CTAACCCGTTCTGCAAGGAAG (SEQ ID NO: 118) | CGGCTGCTGCTGGCGG (SEQ ID NO: 119) |
| 9-g | G2JQR9I071AIBJ | EcoP15I from EarI pool | ATTGATATGTAAGAGATTTC (SEQ ID NO: 120) | AATAGGTACCATTTTCGTT (SEQ ID NO: 121) | | |
| 10-a | G2JQR9I06G19MG | Nest PCR from EarI pool | GATTACTACATTTTTCTCAACAG (SEQ ID NO: 122) | CTTTTGGGGGGGTTGGGCC (SEQ ID NO: 123) | CGTTTATGGGAAAGCGC (SEQ ID NO: 124) | GCTATCCTTCATGAAAACGTG (SEQ ID NO: 125) |
| 10-b | G2JQR9I07IHPYZ | EarI | AATTGGTTACCTCTATCCCC (SEQ ID NO: 126) | CTCATACTGGGATCCGATTT (SEQ ID NO: 127) | | |
| 10-c | G2JQR9I07H9H15 | EcoP15I from EarI pool | GCATAAAGCGGGAGGCTTCT (SEQ ID NO: 128) | CTGTGTCATAGAATAGTGC (SEQ ID NO: 129) | | |
| 10-d | G2JQR9I07IS7M7 | EcoP15I from BtsI pool | TTTCGACCGATTTCAGTCTG (SEQ ID NO: 130) | TTTTTTGACGGTAATTA (SEQ ID NO: 131) | | |
| 10-e | G2JQR9I07H9WDO | EarI | CTTCCTGTGGGTTTTCTA (SEQ ID NO: 132) | TTTTACATCATTCGCGTATT (SEQ ID NO: 133) | | |

TABLE 1-continued

Sequences of degenerate primers used for PCR recovery of error-free fragments

| Fragment (Daughter fragment) | CODE | Restriction enzyme used | Primer sequence Forward direction (5' → 3') | Primer sequence Reverse direction (5' → 3') | Nested PCR Primer sequence Forward direction (5' → 3') | Nested PCR Primer sequence Reverse direction (5' → 3') |
|---|---|---|---|---|---|---|
| 10-f | G2JQR9I07IA5L7 | EcoP15I from EarI pool | TTTTTGAGCTACGCTTTCGG (SEQ ID NO: 134) | TCAATACATTCTACTTT (SEQ ID NO: 135) | | |
| 11-a | G2JQR9I07IN2PX | EcoP15I from EarI pool | GTCAGTAGTATACCGTTCGT (SEQ ID NO: 136) | CGATCTAAGATTGCCTTCCT (SEQ ID NO: 137) | | |
| 11-b | G2JQR9I07IE917 | EarI | TCTCATAATTGGGAATTGTACAG (SEQ ID NO: 138) | TTTATGTTTTTGAATTAGCAGCA (SEQ ID NO: 139) | | |
| 11-c | G2JQR9I07IQTJR | EarI | ATCTTTTATGTACTTTGTGA (SEQ ID NO: 140) | TTTTTCAACACTTTTAGTGT (SEQ ID NO: 141) | | |
| 11-d | G2JQR9I07IM5CB | EarI | TAATTTCCTGTGCAACT (SEQ ID NO: 142) | TCTTGTTTATTTCTTTGGGT (SEQ ID NO: 143) | | |
| 11-e | G2JQR9I06G547R | Nest PCR from BtsI pool | ATGTATCCTCGCTCTTTAACCAG (SEQ ID NO: 144) | CACCCGGTTTGATTATTACTCA (SEQ ID NO: 145) | GGCATTCTGGCGATGGAGAT (SEQ ID NO: 146) | GTCGTAGTACTCATACAGGCG (SEQ ID NO: 147) |
| 11-f | G2JQR9I07HZAYS | Nest PCR from BtsI pool | CTAACGCATTGTCAGGTTTCC (SEQ ID NO: 148) | ACTCCGGATACCAGTGTAGAAC (SEQ ID NO: 149) | GAATCAGAAAACCAGCGTCGCCTGTATGAGTACTACGACGCGTTAGATTCCAC (SEQ ID NO: 150) | TTACTTCCAACGACCGATGTACTGAGCCGCC (SEQ ID NO: 151) |

TABLE 2

Sequences of daughter fragments obtained after PCR recovery

| Fragment (Daughter fragment) | Sequences (5' → 3') | Expected length (bp) |
|---|---|---|
| 1-a | CTATTTGATGTTCGTAGTTCCAGCAGCACCGACTAATGCAGGCTGGCAGTAATGACCCAATTGAAGCCGCCTAACGGGACCACTCCGATCGGCTTCAGCGCCACTACTAGCCTGAACGCTAGCGGCTCTTCCTCGGTTAAGAATGGTACCATCAAGCCTTCGAATGGTATCTTCAAACCTTCTACTCGTGACACCATGGACCCGTGCTCGGGCAACGCCGCTGACGGCTCCATTCGCGTACGTTTTCGCGGTGGCATCGAACGTTGGAAAGAGTGTGTAAACCAAGTGCCGGAGCGTTGCGACCTGTCTGGTCTGACCACGGACAGCACCCGCTACCAGCGGCTTCCGAACACATGACCCTGCGACCTGCTGAGCCTTTTCAAAGCGAAAG (SEQ ID NO: 152) | 392 |
| 1-b | ATCTATTAGGTCATAGTAGGCAGCAGAGGGCATCTTAGCGGTCGCTCTTCTGGCTTCGGCGACGCGAGCGCGGCTTACCAGGAACGTCTGATGACTGTGCCGGTAGATGTTCATGCTGCGCTCCAGGAGCTGTGCCTGGAACGCCGCGTCTCTGTGGGTTCTGTGATCAACTTCAGCGTTCACCAGATGCTGAAGGGTTTTGGCAACGGTACTCACACTATCACCGCGAGCCTGCACCGCGAACAGAATCTGCAGAACTCCTCTCCGTCTTGGGTCGTTTCCCCTACTATCGTGACCCATGAAAACCGCGATGGCTGGTCAGTGGCGCAGGCAGTGGAGTCTATCGAGGCTAGAAGACCACACATGGCACCTTTGCTGCTGCATGCAGAGGAAACCATAAAT (SEQ ID NO: 153) | 402 |
| 1-c | TGCTATTCTTTCTGCCTTTTCAGCAGCAAAGGTGCCATGTGTGGCTCTTCTGGCAACGGTACTCACACTATCACCGCGAGCCTGCACCGCGAACAGAATCTGCAGAACTCCTCTCCGTCTTGGGTCGTTTCCCCTACTATCGTGACCCATGAAAACCGCGATGGCTGGTCAGTGGCGCAGGCAGTGGAGTCTATCGAGGCTGGTCGTGGCTCC | 402 |

TABLE 2-continued

Sequences of daughter fragments obtained after PCR recovery

| Fragment (Daughter fragment) | Sequences (5' → 3') | Expected length (bp) |
|---|---|---|
| | GAAAAGGAATCTGTGACCGCGATTGATTCCGGCTCCTCCCTGGTCAAAATGGGTCTGTTCGATCTGCTGGT TTCCTTCGTCGATGCGGATGACGCGCGTATCCCTTGCTTCGACTTTCCGCTGGCTGTTATTGTGCGCAGAAG AGCGACCGCTAAGATGCCCTCTGCTGTGGAAACGCAACAAACATTC (SEQ ID NO: 154) | |
| 1-d | TCGAGCTCAATAGTTTTTTCAGCAGCACCGACTAATGCAGGCTGGCGTGATGACGCGCGTATCCCTTGCTT CGACTTTCCGCTGGCTGTTATTGTGCGCGAGTGCGATGCAAACCTGTCTCTCACCCTTCGCTTCTCGGACTG CCTGTTCAACGAGGAAACCATTTGTAATTTCACGGATGCCCTCAATATCCTGTTGGCTGAGGCAGTTATCG GTCGTGTAACTCCGGTAGCCGATATCGAGCTGCTGTCTGCAGAGCAGAAACAACAGCTGGAGGAATGGAA CAACACCGATGGTGAATATCCGTCTAGCAAGCGTCTGCACCACCTGATTGAAGAGGTGGTGGAACCACTG CGAACACATGACCCTGCGACCTGCTGCTGCTGAATGCAATCATAAA (SEQ ID NO: 155) | 400 |
| 1-e | TTACTCCATTTTGCACTCTCAGCAGCACCGACTAATGCAGGCTGGCATGATGACGCGCGTATCCCTTGCTTC GACTTTCCGCTGGCTGTTATTGTGCGCGAGTGCGATGCAAACCTGTCTCTCACCCTTCGCTTCTCTTCAACG AGGAAACCATTTGTAATTTCACGGATGCCCTCAATATCCTGTTGGCTGAGGCAGTTATCGGTCGTGTAACT CCGGTAGCCGATATCGAGCTGCTGTCTGCAGAGCAGAAACAACAGCTGGAGGAATGGAACAACACCGATG GTGAATATCCGTCTAGCAAGCGTCTGCACCACCTGATTGAAGAGGTGGTGGAACCACTACGAACACATGA CCCTGCGACCTGCTGTCAACAAAGGCCAAAGAAT (SEQ ID NO: 156) | 389 |
| 2-a | TTAGTTTCAACATGTATATACAGCAGCACCGACTAATGCAGGCTGGAGTGCAACGAGGAAACCATTTGTA ATTTCACGGATGCCCTCAATATCCTGTTGGCTGAGGCAGTTATCGGTCGTGTAACTCCGGTAGCCGATATC GAGCTGCTGTCTGCAGAGCAGAAACAACAGCTGGAGGAATGGAACAACACCGATGGTGAATATCCGTCTA GCAAGCGTCTGCACCACCTGATTGAAGAGGTGGTGGAACGTCACGAAGACAAAATCGCTGTGGTGTGCGA CGAACGTGAACTGACTTACGGTGAACTCAATGCCCACGGCAACTCCCTGGCGCGTTACCTGCACAGCATCA CTGCGAACACATGACCCTGCGACCTGCTGAAAGTGTCGAATATACACAT (SEQ ID NO: 157) | 401 |
| 2-b | CTATTTTCAGTGTGCCTTTCAGCAGCACCGACTAATGCAGGCTGGAGTGGTCACGAAGACAAAATCGCTGT GGTGTGCGACGAACGTGAACTGACTTACGGTGAACTCAATGCCCAGGGCAACTCCCTGGCGCGTTACCTGC GCAGCATTGGTATTCTGCCTGAACAGCTGGTTGCGCTGTTTCTGGACAAATCCGAAAAATTGATCGTAACC ATCCTGGGCGTCTGGAAATCCGGTGCTGCTTACGTGCCAATTGACCCGACCTACCCTGACGAACGTGTTGC TTTCGTTCTGGACGACACGAAAGCCCGTGCGATTATCGCTTCCAATCAGCATGTTGAACGCCTCCCACTGC GAACACATGACCCTGCGACCTGCTGAAAGTTTCATCAACTTAGGA (SEQ ID NO: 158) | 400 |
| 2-c | TATCTGGTAGGAGGGGTTCAGCAGCAAAGGTGCCATGTGTGGCTCTTCTAATTGATCGTAACCATCCTGGG CGTCTGGAAATCCGGTGCTGCTTACGTGCCAATTGACCCGACCTACCCTGACGAACGTGTTCGTTTCGTTCT GGACGACACGAAAGCCCGTGCGATTATCGCTTCCAATCAGCATGTTGAACGCCTCCAGCGTGAAGTAATC GGTGATCGCAACCTGTGCATCATCCGTCTCGAACCACTGCTGGCGAGCCTTGCGCAGGATTCTTCTAAATT CCCTGCCCACAACCTGGATGATTTGCCGCTGACCCAGCCAGCAGCTGGCGTACGTTACTTATACCAAGAAGA GTGACCGCTAAGATGCCCTCTGCTGCAGCGTCATTGCCAGTTCTA (SEQ ID NO: 159) | 400 |
| 2-d | TTCTGTTTGTCTTAAATGCGCAGCAGAGGGCATCTTAGCGGTCGCTCTTCTAGCGTGAAGTAATCGGTGAT CGCAACCTGTGCATCATCCGTCTCGAACCACTGCTGGCGAGCCTTGCGCAGGATTCTTCTAAATTCCCTGCC CACAACCTGGATGATTTGCCGCTGACCAGCCAGCAGCTGGCGTACGTTACTTATACCAGCGGTACCACCGG CTTTCCGAAAGGCATTTTCAAACAGCACACTAACGTTGTTAACTCCATCACAGACCTGTCCGCTCGTTACG GTGTTGCAGGTCAACACCATGAAGCTATCCTGCTCTTCAGTGCTTGCGTTTTCGAACCGTTCGTTCAGAAGA GCCACACATGGCACCTTTGCTGCTGACGCAATCTTAAAAACGGTA (SEQ ID NO: 160) | 402 |
| 2-e | CTGAAATTCATTTATGTTTGCAGCAGCACCGACTAATGCAGGCTGGCAGTGGTTAACTCCATCACAGACCT GTCCGCTCGTTACGGTGTTGCAGGTCAACACCATGAAGCTATCCTGCTCTTCAGTGCTTGCGTTTTCGAACC GTTCGTTCGTCAGACTCTGATGGCCTGGTGAACGGTCACCTGCTCGCCGTGATTAACGATGTAGAAAAAT ATGACGCTGACACCCTCCTCCCATTTATCCGCCGTCACTCTATCACCTATCTGAACGGTACTGCGTCGGTTC TCCAAGAGTATGACTTCTCTGACTGTCCGAGCCTGAACCGTATCATCCTCTGCGAACACATCGACCCTGCG ACCTGCTGCAAAAAGGTACCCCATAG (SEQ ID NO: 161) | 383 |
| 2-f | ATATTCGAGCGTATGTATTACAGCAGCACCGACTAATGCAGGCTGGCGTCTCTATCACCTATCTGAACGGT ACTGCGTCGGTTCTCCAAGAGTATGACTTCTCTGACTGTCCGAGCCTGAACCGTATCATCCTGGTGGGCGA GAACCTGACCGAAGCACGTTACCTGGCACTGCGTCAGCGTTTCAAAAATCGTATTCTGAACGAGTACGGTT TCACCGAGTCTGCGTTCGTGACTGCGCTGAAAATTTTCGATCCGGAAAGCACCCGCAAAGATACCTCCCTG GGGCGTCCGGTGCGCAATGTTAAATGCTATATCTTGAACCCTAGCCTGAAACGCGTGCCAATTGGCATGCG AACACATGACCCTGCGACCTGCTGGAGACTGTAAACAATCACTT (SEQ ID NO: 162) | 399 |
| 2-g | TCATTTCGAGAAAAGGCCGACAGCAGGTCGCAGGGTCATGTGTTCGCAGTGGAACGAGTACGGTTTCACC GAGTCTGCGTTCGTGACTGCGCTGAAAATTTTCGATCCGGAAAGCACCCGCAAAGATACCTCCCTGGGGCG TCCGGTGCGCAATGTTAAATGCTATATCTTGAACCCTAGCCTGAAACGCGTGCCAATTGGTGCTACAGGTG AGCTGCATATTGGCGGCCTGGGTATCTCCAAGGGTTACTTGAATCGTCCGGAACTGACGCCGCACCGCTTC ATCCCGAACCCGTTTCAGACCGATTGCGAAAAACAGCTGGGTATCAACTCTCTGATGTACAAAACCGGCAC TGTCAGCCTGCATTAGTCGGTGCTGCTGCAAAATAAGGGAAAGAACCC (SEQ ID NO: 163) | 402 |
| 3-a | AACGAGGATATACAAATATACAGCAGCAAAGGTGCCATGTGTGGCTCTTCTTGAATCGTCCGGAACTGAC GCCGCACCGCTTCATCCCGAACCCGTTTCAGACCGATTGCGAAAAACAGCTGGGTATCAACTCTCTGATGT ACAAAACCGGTGATCTGGCTCGCTGGCTCCCGAACGGTGAAGTTGAATACCTGGGCCGTGCGGATTTCCAG ATCAAACTGCGCGGTATTCGTATTGAGCCGGGCGAAATCGAGACTATGCTGGCGATGTATCCGCGCGTTCG | 402 |

TABLE 2-continued

Sequences of daughter fragments obtained after PCR recovery

| Fragment (Daughter fragment) | Sequences (5' → 3') | Expected length (bp) |
|---|---|---|
| | TACCTCCCTGGTGGTTTCCAAGAAATTACGTAACGGTCCTGAAGAAACAACGAACGAACACCTGGTAGAG<br>AAGAGCGACCGCTAAGATGCCCTCTGCTGATATACCACTCTCAACACTT (SEQ ID NO: 164) | |
| 3-b | ATGGAGCTTTTATGTGGTTACAGCAGAGGACATCTTAGCGGTCGCTCTTCTCGGATTTCCAGATCAAACTG<br>CGCGGTATTCGTATTGAGCCGGGCGAAATCGAGACTATGCTGGCGATGTATCCGCGCGTTCGTACCTCCCT<br>GGTGGTTTCCAAGAAATTACGTAACGGTCCTGAAGAAACAACGAACGAACACCTGGTAGGCTACTACGTA<br>TGCGACTCCGCATCTGTTTCCGAAGCGGATCTGCTGTCCTTCCTGGAGAAGAAGCTGCCGCGTTATATGAT<br>TCCGACTCGTCTGGTACAGCTGAGCCAGATCCCGGTTAACGTCAACGGTAAAGCCGATCTGCGTGCTCAGA<br>AGAGCCACACATGGCACCTTTGCTGCTGAACAACGAAACTAGACAATT (SEQ ID NO: 165) | 402 |
| 3-c | TGATTATGGTGGTTGCGGTGCAGCAGCACCGACTAATGCAGGCTGGCAGTGTTCCTGGAGAAGAAGCTGC<br>CGCGTTATATGATTCCGACTCGTCTGGTACAGCTGAGCCAGATCCCGGTTAACGTCAACGGTAAAGCCGAT<br>CTGCGTGCTCTGCCGGCGGTTGATATCTCCAACAGCACCGAAGTTCGTTCTGATCTGCGTGGTGATACCGA<br>AATTGCCCTCGGCGAAATCTGGGCGGACGTGCTGGGCGCGCGTCAGCGTTCGGTTAGCCGTAACGATAACT<br>TTTTCCGCCTCGGTGGCCACTCTATCACCTGCATCCAGCTGATTGCGCGTATCCGTCAGCGTCAGCGTCACT<br>GCGAACACATGACCCTGCGACCTGCTGCAGAATAACTAAATTAGTAT (SEQ ID NO: 166) | 402 |
| 4-a | TATTTTTTTCCAATTTTTTACAGCAGCACCGACTAATGCAGGCTGGCAACCTGCATCCAGCTGATTGCGCGT<br>ATCCGTCAGCGTCAGCGTTTGTCTGTGTCTATCTCTGTGGAAGACGTGTTTGCTACACGCACTCTTGAGCGT<br>ATGGCCGACCTGTTGCAAAACAAACAGCAAGAGAAATGCGACAAACCACACGAAGCACCGACTGAACTG<br>CTTGAAGAAAACGCTGCGACTGATAACATCTACCTGGCGAACAGCCTGCAGCAAGGTTTCGTCTACCATTA<br>CCTGAAAAGCATGGAACAAAGTGATGCTTATGTAATGCAGAGCGTTCTGCGTTACAACACCACCCTTTCCC<br>GGATCTGTTCCAGCGTGCCTGGAAACACGCGCAGCCTGCGAACACATGACCCTGCGACCTGCTGGCAACA<br>GAATAGCAGAGGAT (SEQ ID NO: 167) | 399 |
| 4-b | CTAATTTGAATGCAGTCCGTCAGCAGCACCGACTAATGCAGGCTGGCAGTAAGCATGGAACAAAGTGATG<br>CTTATGTAATGCAGAGCGTTCTGCGTTACAACACCACCCTTTCCCCGGATCTGTTCCAGCGTGCCTGGAAA<br>CACGCGCAGCAAAGCTTCCCGGCTCTGCGTCTGCGCTTCTCTTGGGAAAAAGAAGTCTTCCAGCTGCTGGG<br>ATCAGGACCCGCCTCTGGACTGGCGTTTCCTCTACTTCACTGATGTGGTGGCAGGTGCAGATCCCCGTTNTC<br>AGTGGGCGAACCAGTGACAGCTGGGTATCTTCGTTGATGCCTCAGCGCTCAGTTCGGACAGCTGACGCAG<br>AAGGTACACTGCGAACACATGACCCTTCGACCTGCTTGGTTTTTTCCAAAGGTAATGT<br>(SEQ ID NO: 168) | 413 |
| 4-c | TTAAGTATGATTAATGCTGTCAGCAGCACCGACTAATGCAGGCTGGCGTGCAAAGCTTCCCGGCTCTGCGT<br>CTGCGCTTCTCTTGGGAAAAAGAAGTCTTCCAGCTGCTGGATCAGGACCCGCCTCTGGACTGGCGTTTCCT<br>CTACTTCACTGATGTGGCGGCTGGTGCAGTAGAAGACCGTAAACTGGAAGATTTACGCCACCAGGACCTC<br>ACCGAGCGTTTTAAACTGGATGTGGGCCGTCTGTTTCGCGTTTACCTGATCAAACACAGCGAAAACCGTTT<br>CACTTGTCTGTTCTCTTGTCACCCGCTATCCTGGACGGCTGGTCCTTACCGCTTCTGTTCGAAAACCCTGCG<br>AACACATGACCCTGCGACCTGCTGACATATTATGAACAATATCG (SEQ ID NO: 169) | 399 |
| 4-d | GTGGTATGCACGTTGGTCCTCAGCAGCACCGACTAATGCAGGCTGGCAGTCCAAAGCTTCCCGGCTCTGCG<br>TCTGCGCTTCTCTTGGGAAAAAGAAGTCTTCCAGCTGCTGGATCAGGACCCGCCTCTGGACTGGCGTTTCC<br>TCTACTTCACTGATGTGGCGCTGGTGCAGTAGAAGACCGTAAACTGGAAGATTTACGCCGCCAGGACCTCA<br>CCGAGCGTTTTAAACTGGATGTGGGCCGTCTGTTTCGCGTTTACCTGATCAAACACAGCGAAACCGTTTC<br>ACTTGTCTGTTCTCTTGTCACCACGCTATCCTGGACGGCTGGTCCTTACCGCTTCTGTTCGAAAAACNCTGC<br>GAACACATGACCCTGCGACCTGCTGAAACGGNGATCACTCACATA (SEQ ID NO: 170) | 401 |
| 4-e | ATTACTTAGGGTATTGCGTTCAGCAGCACCGACTAATGCAGGCTGGCAGGCGTTTACCTGATCAAACACAG<br>CGAAAACCGTTTCACTTGTCTGTTCTCTTGTCACCACGCTATCCTGGACGGCTGGTCCTTACCGCTTCTGTT<br>CGAAAAAGTACACGAAACATACCTGCAACTGCTGCACGGCGATAACCTGACCTCCTCTATGGATGATCCAT<br>ACACCCGTACCCAACGCTACCTGCATGCGCACCGCGAAGATCACCTCGACTTTTGGGCTGGCGTGGTGCAG<br>AAAATCAACGAACGTTGCGATATGAATGCTCTGTTAAACGAACGCAGCCGCTATAAAGTGCAGCTCACTG<br>CGAACACATGACCCTGCGACCTGCTGATCGCAAAGACTGAAGGTCT (SEQ ID NO: 171) | 401 |
| 4-f | ATAGCGTTATTAATTTCTGTCAGCAGAGGGCATCTTAGGGGTCGCTCTTCTAAGATCACCTCGACTTTTGGG<br>CTGGCGTGGTGCAGAAAATCAACGAACGTTGCGATATGATGCTCTGTTAAACGAACGCAGCCGCTATAAA<br>GTGCAGCTGGCCGACTACGATCAGGTACAGGAACAGCGTCAGCTGACGATCGCTCTGAGCGGTGACGCGT<br>GGCTGGCGGATCTGCGCCAGACATGCAGTGCGCAGGGCATCACGCTGCACTCTATCCTGCAATTTGTATGG<br>CATGCAGTTCTGCATGCCTACGGTGGCGGTACTCACACTATCACTGGCACCACTATTTCTGGTCGCAAGAA<br>GCGCCACACATGGCACCTTTGCTGCTGAGGACTAGCCGAATAACTAT (SEQ ID NO: 172) | 401 |
| 5-a | TCATAGAGGAGGTGCTATGGCAGCAGGTCGCAGGGTCATGTGTTCGCAGTGCTACGGTGGCGGTACTCAC<br>ACTATCACTGGCACCACTATTTCTGGTCGCAACCTCCCGATCCTGGGTATCGAGCGTGCGGTAGGCCCGTA<br>CATTAACACCCTGCCGTTAGTGTTGGACCATTCTACTTTTAAAGACAAGACGATCATGGAAGCTATTGAAG<br>ACGTCCAAGCGAAGGTGAATGTTATGAACTCCCGTGGTAATGTAGAACTGGGTCGCCTGCACAAAACCGA<br>CCTGAAACATGGCCTGTTCGATTCTCTGTTTGTGCTGGAAAACTATCCAAACCTGGATAAATCCAGCCTGC<br>ATTAGTCGGTGCTGCTGAACAGTCAATAAACGATCCG (SEQ ID NO: 173) | 390 |
| 5-b | GATATTTCGCGGTTCTGTTGCAGCAGCACCGACTAATGCAGGCTGGCAGTAGCTATTGAAGACGTCCAAGC<br>GAAGGTGAATGTTATGAACTCCCGTGGTAATGTAGAACTGGGTCGCCTGCACAAAACCGACCTGAAACAT<br>GGCCTGTTCGATTCTCTGTTTGTGCTGGAAAACTATCCAAACCTGGATAAATCCCGTACTCGGAGCACCA | 401 |

TABLE 2-continued

Sequences of daughter fragments obtained after PCR recovery

| Fragment (Daughter fragment) | Sequences (5' → 3') | Expected length (bp) |
|---|---|---|
| | AACTGAACTGGGTTACTCCATCGAGGGTGGTACCGAAAAACTGAACTATCCGCTGGCGGTGATTGCTCGTG<br>AGGTTGAGACCACTGGCGGCTTTACTGTTAGCATCTGCTATGCGAGCGAACTGTTTGAAGAGGTGATCACT<br>GCGAACACATGACCCTGCGACCTGCTGAGTTTAAGTAACCTTTACCT (SEQ ID NO: 174) | |
| 5-c | TAGTCTTTGCCGGTTTATTACAGCAGCACCGACTAATGCAGGCTGGCAGTGAACTGAACTATCCGCTGGCG<br>GTGATTGCTCGTGAGGTTGAGACCACTGGCGGCTTTACTGTTAGCATCTGCTATGCGAGCGAACTGTTTGA<br>AGAGGTGATGATCAGCGAGCTTCTCCATATGGTACAGGATACCCTGATGCAGGTTGCACGCGGGCTCAAC<br>GAACCTGTGGGCTCCCTGGAATACCTGTCTTCCATCCAGTTAGAGCAGCTGGCAGCGTGGAACGCCACCGA<br>AGCGGAGTTCCCGGACACGACCCTGCATGAAATGTTCGAGAACGAAGCATCTCAAAAGCCGGATAAAACA<br>CTGCGAACACATGACCCTGCGACCTGCTGTCTGTAGAATCTTTGCAA (SEQ ID NO: 175) | 400 |
| 5-d | CTAAACTCTTTACTTCCTATCAGCAGAGGGAATCTTAGCGGTCGCTCTTCTTTAGAGCAGCTGGCAGCGTG<br>GAACGCCACCGAAGCGGAGTTCCCGGACACGACCCTGCATGAAATGTTCGAGAACGAAGCATCTCAAAAG<br>CCGGATAAAATTGCAGTCGTATACGAAGAAACCTCTCTGACCTATCGCGAGCTGAACGAACGTGCCAATC<br>GCATGGCGCACCAGCTGCGTTCCGACGTTTCTCCGAACCCGAACGAAGTGATCGCGCTGGTTATGGACAAG<br>AGTGAACACATGATCGTAAATATCTTGGCTGTGTGGAAATCTGGTGGCGCATACGTGCCGATCGATCCGAG<br>AAGATCCACACATGGCACCTTTGCTGCTGAAGCCACATAATAACGAGCT (SEQ ID NO: 176) | 402 |
| 5-e | TTATGAGAAATGTTTCACTGCAGCAGAGGGCATCTTAGCGGTCGCGGACAAGAGTGAACACATGATCGTA<br>AATATCTTGGCTGTGTGGAAATCTGGTGGCGCATACGTGCCGATCGATCCGGGCTACCCGAATGACCGTAT<br>TCAGTATATCCTCGAGGACACTCAGGCGTTGGCTGTTATCGCAGATTCTTGTTACCTGCCTCGTATCAAAGG<br>TATGGCCGCGTCTGGTACGCTGCTCTACCCGTCTGTCCTGCCGGCAAACCCAGACAGCAAATGGTCTGTGT<br>CAAACCCGTCGCCGCTGTCTCGTAGCACCGACCTGGCAGAAGAGCCACACATGGCACCTTTGCTGCTGCTA<br>GATTTGATAGTGTTCTA (SEQ ID NO: 177) | 372 |
| 5-f | TTTGTAATTTGACTCTGATGCAGCAGAGGGCATCTTAGCGGTCGCTCTTCTCGTCTGGTACGCTGCTCTACC<br>CGTCTGTCCTGCCGGCAAACCCAGACAGCAAATGGTCTGTGTCAAACCCGTCGCCGCTGTCTCGTAGCACC<br>GACCTGGCATACATCATCTACACCTCTGGCCACCACCGGCCGCCCGAAAGGCGTGACTGTGGAGCATCACG<br>GTGTGGTGAACCTGCAGGTATCCCTGAGCAAAGTTTTTGGTCTGCGTGACACCGACGACGAAGTCATCCTG<br>TCTTTTTTCTAACTACGTTTTCGATCACTTCGTAGAACAGATGACTGATGCTATCCTGAACGGGCAGAAGAA<br>GAGCCACACAAGGCACCTTTGCTGCTGTGAAAAGTCAAAAGATTCCTA (SEQ ID NO: 178) | 403 |
| 6-a | TACTGGGAGCAAACAATTCTCAGCAGCACCGACTAATGCAGGCTGGCAGTAGGTCTGCGTGACACCGACG<br>ACGAAGTCATCCTGTCTTTTCTAACTACGTTTTCGATCACTTCGTAGAACAGATGACTGATGCTATCCTGAA<br>CGGGCAGAGCGCTGCTGGTTCTGAACGATGGTATGCGTGGTGACAAAGAACGCCTGTACCGCTACATCGAA<br>AAGAACCGTGTAACTTATCTGTCTGGTACTCCATCTGTGGTGTCTATGTATGAGTTCAGCCGTTTCAAAGAC<br>CACCTGCGCCGCGTCGATTGCGTCGGTGAAGCTTTCAGCGAGCCGGTCTTCGACAAAATCCGTGAACACTA<br>CGAACACATGACCCAGCGACCTGCTGAGTGAAAACAGCAGACGAA (SEQ ID NO: 179) | 400 |
| 6-b | GTGGGATGGAAGCTCCTCGACAGCAGAGGGCATCTTAGCGGTCGCTCTCTACCTTCCACGGTTTGGTTATC<br>AATGGTTATGGCCCAACTGAAGTTAGCATCACTACCCATAAGCGTTTATACCCTTTCCCAGAGCGCCGTAT<br>GGATAAGTCGATCGGCCAGCAGGTCCACAACTCTACTAGCTACGTACTGAATGAAGATATGAAGCGTACC<br>CCGATCGGTGCTGTGGGTGAGCTGTACCTGGGCGGTGAAGGTGTTGTCCGCGGTTATCATAATCGTGCGGT<br>GTTACCGCCGAGCGCTTCATCCCGAACCCGTTCCAGTCTGAGGAAGATAAACGTGAAGGCCGTAACAGAA<br>GAACCACACATGGCACCTTTGCTGCTGGCAAAAAGGACATAATACA (SEQ ID NO: 180) | 399 |
| 6-c | TTGTTGGATATATAGGGTTACAAAAGAGGGCATCTTAGCGGTCGCTCTTCTCGATCGGCCAGCAGGTCCAC<br>AACTCTACTAGCTACGTACTGAATGAAGATATGAAGCGTACCCCGATCGGTGCTGTGGGTGAGCTGTACCT<br>GGGCGGTGAAGGTGTTGTCCGCGGTTATCATAATCGTGCGGATGTTACCGCCGAGCGCTTCATCCCGAACC<br>CGTTCCAGTCTGAGGAAGATAAACGTGAAGGCCGTAACAGTCGCCTGTACAAGACGGGTGATCTGGTTCG<br>CTGGATCCCGGGTAGCTCCGGCAAGTCGAATACCTGGGTCGCAATGACTTCCAGGTTAAGATTCGCGAG<br>AAGAACCACACATGGCACCTTTGCTGCTGAAGTACACATCATCCCCATG (SEQ ID NO: 181) | 402 |
| 6-d | AATTCACTCAGAATAATTTTTCAGCAGCAAAGGTGCCTTGTGTGGCTCTCTCGGCGAAGTCGAATACCTGGG<br>TCGCAATGACTTCCAGGTTAAGATTCGCGGCCTCCGTATCGAGCTGGGTGAAATCGAAGCGATCCTGAGCA<br>GCTACCACGGCATTAAACAGAGCGTAGTGATCGCAAAAGACTGCCGTGAGGGGGCACAGAAATTCCTGGT<br>CGGCTATTACGTTGCAGAGCGCTGCCCTGCCGTCCGCAGCGATCCGTCGTTTCATGCAGTCGCGCCTCCCGG<br>GTTACATGGTTCCGTCCCGTCTGATCCGTTTCTAAATTCCCTGTTACTCCGTCCGGGAAGCTGGAAGAAG<br>AGCGACCGCTAAGATGCCCTCTGCTGGAGATTAATTCCAACTAAAT (SEQ ID NO: 182) | 401 |
| 6-e | CTACTGTTCGTTCCCAATTACAGCAGAGGGCATCTTAGCGGTCGCTCTTCTCGTCTGATCCTGGTTTCTAAA<br>TTCCCTGTTACTCCGTCCGGGAAGCTGGACACCAAAGCACTGCCGCCGGCGGAGGAAGCGGAAATCG<br>ACGTTGTTCCACCGCGCTCCGAAATTGAGCGTTCTCTCTGCGACATCTGGGCTGAACTGCTGGAAATGCAC<br>CCGGAAGAAATCGGCATTTACTCTGACTTCTTCCTTGGGCGGCGACAGCCTGAAATCTACTAAGTTATC<br>CTTCATGATCCATGAGTCCTTTAACCGTGCTGTGAGCGTTAGCGCGTTATTCTGCCATCGCACAGTTAGAAG<br>AGCCACACATGGCACCTTTGCTGCTGTTCCCCCAGTTTTACACCAA (SEQ ID NO: 183) | 402 |
| 7-a | ATGTGTTATAGAAGTTGTTGCAGCAGAGGGCATCTTAGCGGTCCTAAGTTATCCTTCATGATCCATGAGTC<br>CTTTAACCGTGCTGTGAGCGTTAGCGCGTTATTCTGCCATCGCACAGTTGAAGCTCAAACTCACCTGATCTT<br>GAACGACGCAGCAGATGTACACGAAATTACCCCGATCGATTGCAACGACACCCAGATGATCCCGGTTTCC<br>CGTGCACAGGAACGTCTGCTGTTCATTCATGAATTCGAAAACGGTTCTAACGCTTACAACATTGACGCGGC | 371 |

TABLE 2-continued

Sequences of daughter fragments obtained after PCR recovery

| Fragment (Daughter fragment) | Sequences (5' → 3') | Expected length (bp) |
|---|---|---|
| | TTTCGAACTGCCAGGTTCTGTGGACGCGAGCCTGCTAGAAGAGCCACACATGGCACCTGTGCTGCTGAGCA GGGATAACACATGTCA (SEQ ID NO: 184) | |
| 7-b | TTTCAGAAACTTAAACTTACCAGCAGAGGGCATCTTAGCGGTCGCTCTTCTGAAGCTCAAACTCACCTGAT CTTGAACGACGCAGCAGATGTACACGAAATTACCCCGATCGATTGCAACGACACCCAGATGATCCCGGTTT CCCGTGCACAGGAACGTCTGCTGTTCATTCATGAATTCGAAAACGGTTCTAACGCTTACAACATTGACGCG GCTTTCGAACTGCCAGGTTCTGTGGACGCGAGCCTGCTGGAACAGGCCCTTCGTGGCAACCTGGCACGTCA CGAAGCACTGCGCACCCTGCTGGTTAAAGATCACGCCACTGGTATTTACCTGCAGAAAGTACTGAATAGA AGAGCCACACATGGCACCTTTGCTGCTGATTCCTATTACTTCTTATAA (SEQ ID NO: 185) | 402 |
| 7-c | TATACAATCTATTGGTAATCCAGCAGAGGGCATCTTAGCGGTCGCTCTTCTAGGAACGTCTGCTGTTCATTC ATGAATTCGAAAACGGTTCTAACGCTTACAACATTGACGCGGCTTTCGAACTGCCAGGTTCTGTGGACGCG AGCCTGCTGGAACAGGCCCTTCGTGGCAACCTGGCACGTCACGAAGCACTGCGCACCCTGCTGGTTAAAG ATCACGCCACTGGTATTTACCTGCAGAAAGTACTGAGTCCGGACGAAGCGCAAGGTATGTTTTCTGTTAAT GTAGATACTGCTAAACAGGTTGAACGTCTGGATCAGGAAATTGCTTCTCTGTCTCAGCACGTCTTCCAGAA GAGCCACACATGGCACCTTTGCTGCTGGAAAGGATTAAAGTATTCCA (SEQ ID NO: 186) | 402 |
| 7-d | TTACATGCTTTCGACACATACAGCAGGTCGCAGGGTCATGTGTTCGCAGTGGGTTGAACGTCTGGATCAGG AAATTGCTTCTCTGTCTCAGCACGTCTTCCGCCTGGACGACGAACTGCCGTGGGAGGCGCGCATCCTGAAA CTGGAATCTGGCGGTCTGTACCTGATCTTGGCCTTCCACCACACCTGCTTCGATGCATGGAGCCTGAAAGT TTTCGAACAGGAGCTGCGCGCGTGTACGCAGCGCTTCAGAAAACGAAATCTGCAGCGAACTTACCGGCA TTAAAAGCACAGTATAAGGAATACGCTCTGTACCACCGCCGCCAGCTTAGCGGCGACCGCATGCGTAACA CAGCCAGCCTGCATTAGTCGGTGCTGCTGAAAGATCCTCACACTATACA (SEQ ID NO: 187) | 402 |
| 7-e | GTTAATTTCTGGGGATACGTCAGCAGAGGGCATCTTAGCGGTCGTTCTTCTGAATACGCTCTGTACCACCG CCGCCAGCTTAGCGGCGACCGCATGCGTAACCTGTCCGATTTCTGGTTACGTAAACTGATCGGTCTGGAAC CACTGCAGCTGATCACCGATCGTCCGCGTCCGGTTCAGTTCAAATACGACGGTGACGATCTGAGCATCGAA CTGTCCAAGAAAGAGACCGAAAACCTGCGCGGCGTTGCAAAACGTTGTAAGTCTTCCTTATATGTTGTACT GGTATCTGTTTACTGTGTCATGCTGGCAAGCTACGCCAACCAGAGCGATGTTAGCGTGGGCATCCCAAGAA GACCACACATGGTCACCTTTGCTGCTGCTTATAAAAAGCGTGAGTTA (SEQ ID NO: 188) | 401 |
| 7-f | TACCTGTGATCTGCGTCGTACAGCAGAGGGCATCTTAGCGGTCGCTCTTCTTGATCACCGATCGTCCGCGTC CGGTTCAGTTCAAATACGACGGTGACGATCTGAGCATCGAACTGTCCAAGAAAGAGACCGAAAACCTGCG CGGCGTTGCAAAACGTTGTAAGTCTTCCTTATATGTTGTACTGGTATCTGTTTACTGTGTCATGCTGGCAAG CTACGCCAACCAGAGCGATGTTAGCGTGGGCATCCCAGTATCACACCGTACGCACCCGCAGTTCCAGTCTG TTATCGGCTTTTTCGTTAACCTGGTCGTTCTGCGTGTAGATATCAGCCAGTCCGCTATTTGCGGTTAGAAGA GCCACACATGGCACCTTTGCTGCTGTCTTCATCGATAAATACAAA (SEQ ID NO: 189) | 402 |
| 8-a | GAAGCACCTGTCTTATTTAACAGCAGCACCGACTAATGCAGGCTGGCATGAAAACGTTGTAAGTCTTCCTT ATATGTTCTGGTATCTGTTTACTGTGTCATGCTGGCAAGCTACGCCACCAGAGCGATGTTAGCGTGGGCAT CCCAGTATCACACCGTACGCACCCGCAGTTCCAGTCTGTTATCGGCTTTTTCGTTAACCTGGTCGTTCTGCG TGTAGATATCAGCCAGTCCGCTATTTGCGGTTTAATCCGTCGCGTCATGAAAGAACTGGTTGACGCGCAGC TGCACCAGGATATGCCGTTCCAGGAAGTTACGAAACTGCTGCAGGTGGATAACGATCCTAGCACTGCGAA CACATGACCCTGCGACCTGCTGAAGCCTACCCGGGAAGATCA (SEQ ID NO: 190) | 397 |
| 8-b | TCATCCTATTACGATGCCCGCAGCAGCAAAGGTGCCATGTGTGGCTCTTTATGCCGTTCCAGGAAGTTACG AAACTGCTGCAGGTGGATAACGATCCTAGCCGTCACCCGTTGGTTCAGAACGTATTTAACTTTGAGTCTCG CGCGAACGGTGAACACGATGCCCGCTCTGAAGACGAGGGCTCTCTTGCATTCAATCAGTACCGTCCGGTTC AGCCGGTTGACAGCGTGGCCAAATTCGATCTGAACGCCACCGTCACCGAACTGGAATCCGGTCTGCGTGTT AATTTCAACTACGCGACCAGCTTATTCAATAAATCCACCATCCAGGGCTTCCTGCACACATATGAAAGAAG AGGACCGCTAAGATGCCCTCTGCTGCAATAAAAAGCTTCCAACGC (SEQ ID NO: 191) | 400 |
| 8-c | ATTTATAAGGACGGGCCAGCCAGCAGAGGGCATCTTAGCGGTCGCTCTTCTCCAGCTTATTCAATAAATCC ACCATCCAGGGCTTCCTGCACACATATGAATACCTTCTGCGTCAGCTGTCCGAACTGAGCGCTGAAGGCAT CAACGAAGATACCCAGCTGTCACTGGTTCGCCCGACTGAGAACGGGGATCTGCACCTGCCACTGGCCCAG TCTCCGCTCGCGACCACTGCAGAAGAACAGAAAGTTGCTTCCCTGAACCAGGCTTTCGAACGTGAAGCCTT CCTGGCGGCGGAAAAAATCGCCGTTGTTCAAGGGGACCGCGCTCTGTCGTATGCCGACCTGAACGGTCAG AAACCACACATGGCACCTTTGCTGCTGTACCAATACGGGGANCGTTT (SEQ ID NO: 192) | 400 |
| 8-d | TAATCTGATCGATGCTAGGACAGCAGGTCGCAGGGTCATGTGTTCGTAGTGCGCCGTTGTTCAAGGGGACC GCGCTCTGTCGTATGCCGACCTGAACGGTCAGGCTAATCAACTGGCGCGTTATATCCAGTCCGTCTCCTGC ATCGGTGCCGACGACGGCATCGCCCTGATGCTGGAAAAGAGCATCGATACTATCATCTGCATTCTGGCAAT CTGGAAAGCAGGCGCGCGTATGTGCCGCTGGATCCGACCTACCCACCAGGCCGTGTACAACTGATCCTG GAGGAAATCAAAGCGAAAGCTGTGCTGGTACACTCTTCCCACGCCTCTAAATGTGAACGTCACGGTGCCA CTGCCAGCCTGCATTAGTCGGTGCTGCTGTTAGGAGGATTGAATCAAAA (SEQ ID NO: 193) | 402 |
| 9-a | TAGCCCTTTTCGTATTTGCATCAGCAGCAAAGGTGCCATGTGTGGCTCTTTCCTACCCACCAGGCCGTGTAC AACTGATCCTGGATGAAATCAAAGCGAAACTGTGCTGGTACACTCTTCCACGCCTCTAAATGTGAACGTCA CGGTGCCAAAGTCATTGCAGTAGACTCTCCGGCTATTGAAACGGCAGTGAGCCAGCAGTCTGCAGCTGATC | 400 |

TABLE 2-continued

Sequences of daughter fragments obtained after PCR recovery

| Fragment (Daughter fragment) | Sequences (5' → 3') | Expected length (bp) |
|---|---|---|
| | TGCCGACCATTGCTAGCCTGGGTAATCTGGCATATATCATCTTTACTAGCGGCACTTCTGGCAAACCGAAA<br>GGCGTTCTGGTAGAGCAAAAAGCCGTTCTGCTGCTGCGCGACGCCCTGCGTGAGCGTTACTTCGAGAAGA<br>GCGACCGCTAAGATGCCCTCTGCTGTAGACTGAGTTGAACAACTA (SEQ ID NO: 194) | |
| 9-b | ATCATTGCACTTGTTGTTCGCAGCAGCAAAGGTGCCATGTGTGGCTCTTCTATCATCTTTACTAGCGGCACT<br>TCTGGCAAACCGAAAGGCGTTCTGGTAGAGCAAAAAGCCGTTCTGCTGCTGCGCGACGCCCTGCGTGAGC<br>GTTACTTCGGTCGTGATTGTACCAAACATCACGGTGTTCTGTTCCTGAGCAACTACGTTTTCGACTTCTCCG<br>TAGAACAGCTGGTTCTGTCTGTACTCTCAGGCCACAAACTGATTGTCCCGCCGGCGGAGTTTGTGGCGGAT<br>GACGAATTCTATCGTATGGCCTCTACCCACGGTCTTTCTTACCTGTCTGGCACCCCGAGCCTGCTTAGAAGA<br>GCGACCGCTAAGATGCCCTCTGCTGAAATCAGTAAAAAACCTTCC (SEQ ID NO: 195) | 402 |
| 9-c | TTATTCGTGGATTGGTGTTCCAGCAGAGGGCATCTTAGCGGTCGCTCTTCTTTCGACTTCTCCGTAGAACAG<br>CTGGTTCTGTCTGTACTCTCAGGCCACAAACTGATTGTCCCGCCGGCGGAGTTTGTGGCGGATGACGAATT<br>CTATCGTATGGCCTCTACCCACGGTCTTTCTTACCTGTCTGGCACCCCGAGCCTGCTTCAAAAAATCGATCT<br>GGCACGTCTGGATCACCTGCAGGTTGTAACGCGGCGGGTGAGGAACTCCACGCGACCCAGTACGAAAAA<br>ATGCGTCGTCGTTTTAACGGTCCAATCTACAACGCTTATGGTGTTACCGAGACAACGGTGTACAACAGAAG<br>AACCACACATGGCACCTTTGCTGCTGTAATCAGAACCTAGAAAAAT (SEQ ID NO: 196) | 402 |
| 9-d | TGATTTCACCACTAAGTCTCAGCAGGTCGCAGGGTCATGTGTTCGCAGTGACGGTCCAATCTACAACGCTT<br>ATGGTGTTACCGAGACAACGGTGTACAACATCATCGTGAATTCACCACCAACTCCATCTTCGAAAACGCA<br>TTACGCGAAGTCCTGCCGGGCACCCGTGCGTACGTTCTGAACGCGGCGCTGCAGCCGGTTCCATTCGACGC<br>TGTGGGTGAACTGTATCTGGCCGGCGATAGCGTAACCCGTGGTTACCTGAACCAGCCGTTGCTGACCGATC<br>AGCGTTTCATCCCTAACCCGTTCTGCAAGGAAGAAGACATCGCGATGGGTCGTTTCGCTCGTCGTCACGC<br>CAGCCTGCATTAGTCGGTGCTGCTGGCACGAGAAATAAAGGAGG (SEQ ID NO: 197) | 399 |
| 9-e | TAAAGTTATCATGTGCTACCCAGCAGCAAAGGTGCCATGTGTGGCTCTTCTACAAAACCGGCGACCTGGTT<br>CGCTCTCGCTTCAACCGCCAGCAGCAGCCGCAGCTGGAATACCTGGGCCGTGGCGACCTGCAGATTAAAA<br>TGCGTGGTTACCGCATTGAAATTAGCGAAGTACAGAACGTGCTGACCTCCTCCCCGGGCGTACGCGAAGGT<br>GCGGTTGTGGCTAAATATGAAAACAACGACACGTATAGCGTACTGCACATTCCTTAGTCGGTTATTATAC<br>CACTGATAACGAAACAGTTTCAGAAGCTGATATCCTCACCTTCATGAAAGCGCGTCTGCCGACCTATAAGA<br>AGAGGACCGCTAAGATGCCCTCTGCTGGAGATGAATATAGGTTTACA (SEQ ID NO: 198) | 401 |
| 9-f | GTTCATTGCATAATGCTTCTCAGCAGCACCGACTAATGCAGGCTGGAGTGTTCCATTCGACGCTGTGGGTG<br>AACTGTATCTGGCCGGCGATAGCGTAACCCGTGGTTACCTGAACCAGCCGTTGCTGACCGATCAGCGTTTC<br>ATAACTAACCCGTTCTGCAAGGAAGAAGACATCGCGATGGGTCGTTTCGCTCGTCGTGTACAAAACCGGCG<br>ACCTGGTTCGCTCTCGCTTCAACCGCCAGCAGCAGCCGCAGCTGGAATACCTGGGCCGTGGCGACCTGCAG<br>ATTAAAATGCGTGGTTACCGCATTGAAATTAGCGAAGTACAGAACGTGCTGACCTCCTCCCGGGCGCATGC<br>GAACACATGACCCTGCGACCTGCTGCTGGATGTAAAGGGNTTTAA (SEQ ID NO: 199) | 399 |
| 9-g | ATTGATATGTAAGAGATTTCCAGCAGCAAAGGTGCCATGTGTGGCTCTTATCGTACTGCACATTCCTTAGT<br>CGGTTATTATACCACTGATAACGAAACAGTTTCAGAAGCTGATATCCTTCACCTTCATGAAAGCGCGTCT<br>CGACCTATATGGTGCCTTCTCACCTGTGCTGCCTGGAAGGTGCTCTGCCAGTCACTATTAACGGTAAACTG<br>GACGTTCGTCGTCTGCCTGAAATTATCAACGACAGTGCGCAATCCTCATATTCCCCGCCGCGCAACATTAT<br>CGAAGCGAAAATGCCGTTTATGGGAAAGCGCGCTGGGTATGGAACGCTGCGGTATTGACGATGACAGA<br>AGAGCGACCGCTAAGATGCCCTCTGCTGAACGAAAATGGTACCTATT (SEQ ID NO: 200) | 401 |
| 10-a | GATTACTACATTTTTCTCAACAGCAGCACCGACTAATGCAGGCTGGCAGTGAACGGTAAACTGGACGTTCG<br>TCGTCTGCCTGAAATTATCAACGACAGTGCGAATCCTCATATTCCCCGCCGCGCAACATTATCGAAGCGAA<br>AATGTGCGTTTATGGGAAAGCGCGCTGGGTATGGAACGCTGCGGTATTGACGATGACCTCTTCAAGCTGGG<br>GGGGGATTCTATCACCAGTCTGCACCTCGTCGCACAGATTCACAATCAGGTGGGCTGTAAGATTACCGTGC<br>GCGATATTTTCGAACACCGTACCGCGCGTGCTCTCCACGATCACGTTTTCATGAAGGATAGCGATCATGCG<br>AACACATGACCCTGCGACCTGCTGGCCCAACCCCCCCCAAAAG (SEQ ID NO: 201) | 398 |
| 10-b | AATTGGTTACCTCTATCCCCAGCAGCAAAGGTGCCATGTGTGGCTCTTCTACCGTACCGCGCGTGCTCTCC<br>ACGATCACGTTTTCATGAAGGATAGCGATCGCTCTAACGTCACCCAGTTCCGTACCGAGCAGGGGCCGGTC<br>ATTGGCGAAGCTCCGCTGCTGCCGATCCAGGATTGGTTCTTGAGCAAAGCTCTGCAGCACCCTATGTACTG<br>GAACCACACGTTCTACGTACGTACCCCGGAACTGGACGTTGATTCCCTGAGTGCGGCCGTTCGTGACCTGC<br>AGCAGTACCACGACGTTTCCGCATGCGCCTGAAACGCGAAGAAGTTGGCTTTGTACAGTCCTTTGAGAAG<br>AGCGACCGCTAAGATGCCCTCTGCTGAAATCGGATCCCAGTATGAG (SEQ ID NO: 202) | 402 |
| 10-c | GCATAAAGCGGGAGGCTTCTCAGCAGAGGGCATCTTAGCGGTCGCTCTTCTTTTCCGCATGCGCCTGAAAC<br>GCGAAGAAGTTGGCTTTGTACAGTCCTTTGCCGAAGACTTTTCCCGGCGCAGCTGCGTGTACTGAACGTG<br>AAGGACGTGGATGGTAGCGCGGCGGTTAACGAAATCCTGGACGTTGGCAAAGCGGCTTCAACCTGGAAA<br>ACGGTCCGATCGGCTCGATCGGTTATCTGCATGGCTATGAAGACCGCTCCGCACGTGTGTGGTTTTCTGTA<br>CACCACATGGCCATTGACACTGTTTCCTGGCAGATCCTGGTTCGTGATCTGCAGACTCTGTACCGTAAAGA<br>AGAACCACACATGGCACCTTTGCTGCTGGCACTATTCTATGACACAG (SEQ ID NO: 203) | 401 |
| 10-d | TTTCGACCGATTTCAGTCTGCAGCAGGTCGCAGGGTTATGTGTTCGCAGTGCAACCTGGAAAACGGTCCGA<br>TCGGCTCGATCGGTTATCTGCATGGCTATGAAGACCGCTCCGCACGTGTGTGGTTTTCTGTACACCACATG<br>GCCATTGACACTGTTTCCTGGCAGATCCTGGTTCGTGATCTGCAGACTCTGTACCGTAACGGTTCCCTGGGT<br>TCCAAAGGTTCTTCATTTCGCCAATGGGCCGAGGCAATCCAAAACTACAAAGCGAGCGACTCGGAACGTA | 399 |

TABLE 2-continued

Sequences of daughter fragments obtained after PCR recovery

| Fragment (Daughter fragment) | Sequences (5' → 3') | Expected length (bp) |
|---|---|---|
| | ACCATTGGAACAAGCTGGTTATGGAAACTGCATCGTCGATCAGCGCGCTGCCGACCTCCACTGGTTCCACT<br>ACCAGCCTGCATTAGTCGGTGCTGCTGTAATTACCGTCAAAAAA (SEQ ID NO: 204) | |
| 10-e | CTTCCTGTGGGTTTTCTACAGCAGCAAAGGTGCCATGTGTGGCTCTTCTTCCAAAACTACAAAGCGAGCGA<br>CTCGGAACGTAACCATTGGAACAAGCTGGTTATGGAAACTGCATCGTCGATCAGCGCGCTGCCGACCTCCA<br>CTGGTTCTCGCGTACGTCTCTCCCGTTCTCTGTCTCCTGAAAAAACTGCTTCTCTGATCCAGGGTGGCATCG<br>ATCGTCAGGATGTAAGCGTATACGATTCTCTGCTGACTTCTGTTGGCCTGGCTTTGCAACACATCGCGCCG<br>ACTGGCCCGTCTATGGTTACAATCGAGGGTCACGGCCGCGAAGAAGTTGACCAGACCCTGGATGAGAAGA<br>GCGACCGCTAAGATGCCCTCTGCTGAATACGCGAATGATGTAAAA (SEQ ID NO: 205) | 400 |
| 10-f | TTTTTGAGCTACGCTTTCGGCAGCAGCAAAGGTGCCATGTGTGGCTCTTCTACTTCTGTTGGCCTGGCTTTG<br>CAACACATCGCGCCGACTGGCCCGTCTATGGTTACAATCGAGGGTCACGGCCGCGAAGAAGTTGACCAGA<br>CCCTGGATGTTTTCTCGTACGATGGGCTGGTTCACTACCATGTATCCGTTCGAAATCCCGCGTCTGTCGACGG<br>AAAACATCGTGCAGGGTGTTGTTGCTGTAAGTGAACGCTTCCGCCAAGTTCCGGCTCGCGGTGTTGGTTAT<br>GGTACTCTGTACGGTTACACCCAGCACCCTCTGCCGCAGGTTACTGTTAACTACCTGGGCCAGCTGAGAAG<br>GACCGCTAAGATGCCCTCTGCTGCTGAAAGTAGAATGTATTGA (SEQ ID NO: 206) | 399 |
| 11-a | GTCAGTAGTATACCGTTCGTCAGCAGAGGGCATCTTAGCGGTCGCTCTTCTACACCCAGCACCCTCTGCCG<br>CAGGTTACTGTTAACTACCTGGGCCAGCTGGCTCGTAAACAGAGCAAGCCGAAAGAATGGGTTCTGGCAG<br>TTGGTGATAACGAGTTCGAGTACGGTCTGATGACCTCCCCGGAGGATAAGGACCGTTCGAGCTCCGCAGTG<br>GATGTTACGGCCGTCTGCATCGACGGGACGATGATCATCGATGTGGACTCGGCTTGGTCTTTGGAAGAATC<br>TGAACAGTTCATCTCGTCAATTGAAGAAGGTCTGAACAAAATCCTGGACGGTCGTGCATCCCAGCAGAAG<br>AAAGCCACACATGGCACCTTTGCTGCTGAGGAAGGCAATCTTAGATCG (SEQ ID NO: 207) | 401 |
| 11-b | TTCTGCAGAACGTTTTTGTAACAGCAGCAAAGGTGCCATGTGTGGCTCTTCTGCTCGTAAACAGAGCAAGC<br>CGAAAGAATGGGTTCTGGCAGTTGGTGATAACGAGTTCGAGTACGGTCTGATGACCTCCCCGGAGGATAA<br>GGACCGTTCGAGCTCCGCAGTGGATGTTACGGCCGTCTGCATCGACGGGACGATGATCATCGATGTGGACT<br>CGGCTTGGTCTTTGGAAGAATCTGAACAGTTCATCTCGTCAATTGAAGAAGGTCTGAACAAAATCCTGGAC<br>GGTCGTGCATCCCAGCAGACTAGCCGCTTTCCGGATGTGCCGCAGCCAGCAGAGACCTACACCCCATACA<br>GAAGAGTGACCGCTAAGATGCCCTCTGCTGGATGGGCCATAATACCGTCG (SEQ ID NO: 208) | 403 |
| 11-c | ATCTTTTATGTACTTTGTGACAGCAGAGGGCATCTTAGCGGTCGCTCTTCTGATGTGGACTCGGCTTGGTCT<br>TTGGAAGAATCTGAACAGTTCATCTCGTCAATTGAAGAAGGTCTGAACAAAATCCTGGACGGTCGTGCATC<br>CCAGCAGACTAGCCGCTTTCCGGATGTGCCGCAGCCAGCAGAGACCTACACCCCATACTTCGAATATCTGG<br>AACCGCCGCGCCAGGGCCCGACCCTGTTTCTGCTGCCACCGGGTGAAGGTGGTGCGGAATCTTACTTCAAC<br>AACATCGTCAAACGCTTGCGTCAAACTAACATGGTTGTCTTTAACAACTACTACCTGCACTCCAAAAGAAG<br>AGCCACACATGGCACCTTTGCTGCTGACACTAAAAGTGTTGAAAAA (SEQ ID NO: 209) | 402 |
| 11-d | TAATTTCCTGTGCAACTCAGCAGCAAAGGTGCCATGTGTGGCTCTTCTTTCGAATATCTGGAACCGCCGCG<br>CCAGGGCCCGACCCTGTTTCTGCTGCCACCGGGTGAAGGTGGTGCGGAATCTTACTTCAACAACATCGTCA<br>AACGCTTGCGTCAAACTAACATGGTTGTCTTTAACAACTACTACCTGCACTCCAAACGTCTGCGCACCTTC<br>GAGGAACTGGCTGAAATGTATCTGGACCAGGTACGCGGCATCCAACCGCACGGTCCATACCACTTCATCG<br>GCTGGAGCTTCGGGGCATTCTGGCGATGGAGATGTCCCGTCGTCTGGTTGCGAGC GACGAAAAAGAAGA<br>GCGACCGCTAAGATGCCCTCTGCTGACCCAAAGAAATAAACAAGA (SEQ ID NO: 210) | 398 |
| 11-e | ATGTATCCTCGCTCTTTAACCAGCATCACCGACTAATGCAGGCTGGCAGTGGCATTCTGGCGATGGAGATG<br>TCCCGTCGTCTGGTTGCGAGCGACGAAAAATTGGTTTCTGGGTATTATCGACACCTATTTCAACGTACGTG<br>GTGCCACTCGCACCATTGGCCTTGGTGATACTGAAATCCTGGATCCACCACATCTATAACCCGGAC<br>CCGGCAAACTTTCAGCGTCTGCCGTCTGCCACCGACCGTATCGTCCTGTTTAAGGCCATGCGTCCGAATAA<br>TAAATATGAATCAGAAACCAGCGTCGCCTGTATGAGTACTACGACACTGCGAACACATGACCCTGCGACC<br>TGCTGAGTAATAATCAAACCGGGTG (SEQ ID NO: 211) | 379 |
| 11-f | CTAACGCATTGTCAGGTTTCCAGCAGCACCGACTAATGCAGGCTGGCAGTGCGTATCGTCCTGTTTAAGGC<br>CATGCGTCCGAATAATAAATATGAATCAGAAACCAGCGTCGCCCTACGACGCGTTAGATTCCACGGACT<br>GGACCGCATGTTACCAGGCGATCCCTACCTCCTCATGGTCGCGCCTGCGCACGATCCACACCTTCCCGGGT<br>TCGGAAATCCACAACCGCTGGTCCCGTTGCGTTCGTCTGAGCCGTAACACCAGCCTTGCCATCGACCCGTC<br>TCTGGCAGCTCAGTACATCGGTCGTTGGAAGTAAGCAGAGTAAAGACCGTGCACTTATCACTGGAACACA<br>TGACCCTGCGACCTGCTGTTCTACACTGGTATCCGGAGT (SEQ ID NO: 212) | 392 |

The desired PCR amplification products were electrophoresed through an agarose gel to excise bands of the desired size, and DNA was purified using a gel purification kit (AccuPrep™, Bioneer, Korea). For the construction of ~1,000 bp DNA sequence, 3-8 gel-purified gene fragments were pooled. For each pool, restriction enzyme digestion was carried out as follows: when EarI or EcoP15I was used, 2 µl EarI or EcoP15I, 5 µl NEB buffer, 0.5 µl 100×BSA, 10 µl water, and 30 µl purified (and pooled) DNA fragments were mixed, followed by digestion at 37° C. for 3 h (for EcoP15I, 10 ATP was further added); and when BtsI was used, 2 µl BtsI, 5 µl NEB buffer, 0.5 µl 100×BSA, 10 µl water, and 30 µl PCR products were mixed, followed by digestion at 55° C. for 3 h. The restriction digest products were electrophoresed through 1.5% agarose gels to obtain expected bands (daughter fragments, 300 bp; FIG. 8h). The expected DNA fragment sequences after digestion (products obtained after Type IIS restriction enzyme digestion or error-correction PCR) are listed in Table 3.

TABLE 3

Sequences of daughter fragments obtained after Type IIS restriction enzyme digestion or nested PCR

| Fragment (Daughter fragment) | Sequence (5' → 3') | Expected length (bp) |
|---|---|---|
| 1-a | ATGACCCAATTGAAGCCGCCTAACGGGACCACTCCGATCGGCTTCAGCGCCACTACTAGCCTGAACGCTA GCGGCTCTTCCTCGGTTAAGAATGGTACCATCAAGCCTTCGAATGGTATCTTCAAACCTTCTACTCGTGAC ACCATGGACCCGTGCTCGGGCAACGCCGCTGACGGCTCCATTCGCGTACGTTTTCGCGGTGGCATCGAAC GTTGGAAAGAGTGTGTAAACCAAGTGCCGGAGCGTTGCGACCTGTCTGGTCTGACCACGGACAGCACCCG CTACCAGCTGGCTTCGA (SEQ ID NO: 213) | 298 |
| 1-b | CTGTCTGGTCTGACCACGGACAGCACCCGCTACCAGCTGGCTTCGACCGGCTTCGGCGACGCGAGCGCGG CTTACCAGGAACGTCTGATGACTGTGCCGGTAGATGTTCATGCTGCGCTCCAGGAGCTGTGCCTGGAACGC CGCGTCTCTGTGGGTTCTGTGATCAACTTCAGCGTTCACCAGATGCTGAAGGGTTTTGGCAACGGTACTCA CACTATCACCGCGAGCCTGCACCGCGAACAGAATCTGCAGAACTCCTCTCCGTCTTGGGTCGTTTCCCCTA CTATCGTGACCCATG (SEQ ID NO: 214) | 298 |
| 1-c | AACGGTACTCACACTATCACCGCGAGCCTGCACCGCGAACAGAATCTGCAGAACTCCTCTCCGTCTTGGGT CGTTTCCCCTACTATCGTGACCCATGAAAACCGCGATGGCTGGTCAGTGGCGCAGGCAGTGGAGTCTATC GAGGCTGGTCGTGGCTCCGAAAAGGAATCTGTGACCGCGATTGATTCCGGCTCCTCCCTGGTCAAAATGG GTCTGTTCGATCTGCTGGTTTCCTTCGTCGATGCGGATGACGCGCGTATCCCCTTGCTTCGACTTTCCGCTGG CTGTTATTGTGCGC (SEQ ID NO: 215) | 297 |
| 1-d | TGACGCGCGTATCCCTTGCTTCGACTTTCCGCTGGCTGTTATTGTGCGCGAGTGCGATGCAAACCTGTCTCT CACCCTTCGCTTCTCGGACTGCCTGTTCAACGAGGAAACCATTTGTAATTTCACGGATGCCCTCAATATCC TGTTGGCTGAGGCAGTTATCGGT (SEQ ID NO: 216) | 166 |
| 1-e | ACGAGGAAACCATTTGTAATTTCACGGATGCCCTCAATATCCTGTTGGCTGAGGCAGTTATCGGTCGTGTA ACTCCGGTAGCCGATATCGAGCTGCTGTCTGCAGAGCAGAAACAACAGCTGGAGGAATGGAACAACACC GATGGTGAATATCCGTCTAGCAAGCGTCTGCACCACCT (SEQ ID NO: 217) | 178 |
| 2-a | GTGAATATCCGTCTAGCAAGCGTCTGCACCACCTGATTGAAGAGGTGGTGGAACGTCACGAAGACAAAAT CGCTGTGGTGTGCGACGAACGTGAACTG (SEQ ID NO: 218) | 98 |
| 2-b | TCACGAAGACAAAATCGCTGTGGTGTGCGACGAACGTGAACTGACTTACGGTGAACTCAATGCCCAGGGC AACTCCCTGGCGCGTTACCTGCGCAGCATTGGTATTCTGCCTGAACAGCTGGTTGCGCTGTTTCTGGACAA ATCCGAAAAATTGATCGTAACCATCCTGGGCGTCTGGAAATCCGGTGCTGCTTACGTGCCAATTGACCCGA CCTACCCTGACGAACGTGTTCGTTTCGTTCTGGACGACACGAAAGCCCGTGCGATTATCGCTTCCAATCAG CATGTTGAACGCCT (SEQ ID NO: 219) | 297 |
| 2-c | TGATCGTAACCATCCTGGGCGTCTGGAAATCCGGTGCTGCTTACGTGCCAATTGACCCGACCTACCCTGAC GAACGTGTTCGTTTCGTTCTGGACGACACGAAAGCCCGTGCGATTATCGCTTCCAATCAGCATGTTGAACG CCTCCAGCGTGAAGTAATCGGTGATCGCAACCTGTGCATCATCCGTCTCGAACCACTGCTGGCGAGCCTTG CGCAGGATTCTTCTAAATTCCCTGCCCACAACCTGGATGATTTGCCGCTGACCAGCCAGCAGCTGGCGTAC GTTACTTATACCA (SEQ ID NO: 220) | 297 |
| 2-d | AGCGTGAAGTAATCGGTGATCGCAACCTGTGCATCATCCGTCTCGAACCACTGCTGGCGAGCCTTGCGCA GGATTCTTCTAAATTCCCTGCCCACAACCTGGATGATTTGCCGCTGACCAGCCAGCAGCTGGCGTACGTTA CTTATACCAGCGGTACCACCGGCTTTCCGAAAGGCATTTTCAAACAGCACACTAACGTTGTTAACTCCATC ACAGACCTGTCCGCTCGTTACGGTGTTGCAGGTCAACACCATGAAGCTATCCTGCTCTTCAGTGCTTGCGT TTTCGAACCGTTCG (SEQ ID NO: 221) | 297 |
| 2-e | GTTAACTCCATCACAGACCTGTCCGCTCGTTACGGTGTTGCAGGTCAACACCATGAAGCTATCCTGCTCTT CAGTGCTTGCGTTTTCGAACCGTTCGTTCGTCAGACTCTGATGGCCCTGGTGAACGGTCACCTGCTCGCCG TGATTAACGATGTAGAAAAATATGACGCTGACACCCTCCTCCCATTTATCCGCCGTCACTCTATCACCTAT CTGAACGGTACTGCGTCGGTTCTCCAAGAGTATGACTTCTCTGACTGTCCGAGCCTGAACCGTATCAT (SEQ ID NO: 222) | 281 |

TABLE 3-continued

Sequences of daughter fragments obtained after Type IIS restriction enzyme digestion or nested PCR

| Fragment (Daughter fragment) | Sequence (5' → 3') | Expected length (bp) |
|---|---|---|
| 2-f | CTATCACCTATCTGAACGGTACTGCGTCGGTTCTCCAAGAGTATGACTTCTCTGACTGTCCGAGCCTGAAC CGTATCATCCTGGTGGGCGAGAACCTGACCGAAGCACGTTACCTGGCACTGCGTCAGCGTTTCAAAAATC GTATTCTGAACGAGTACGGTTTCACCGAGTCTGCGTTCGTGACTGCGCTGAAAATTTTCGATCCGGAAAGC ACCCGCAAAGATACCTCCCTGGGGCGTCCGGTGCGCAATGTTAAATGCTATATCTTGAACCCTAGCCTGAA ACGCGTGCCAAT (SEQ ID NO: 223) | 295 |
| 2-g | ACGAGTACGGTTTCACCGAGTCTGCGTTCGTGACTGCGCTGAAAATTTTCGATCCGGAAAGCACCCGCAA AGATACCTCCCTGGGGCGTCCGGTGCGCAATGTTAAATGCTATATCTTGAACCCTAGCCTGAAACGCGTGC CAATTGGTGCTACAGGTGAGCTGCATATTGGCGGCCTGGGTATCTCCAAGGGTTACTTGAATCGTCCGGAA CTGACGCCGCACCGCTTCATCCCGAACCCGTTTCAGACCGATTGCGAAAAACAGCTGGGTATCAACTCTCT GATGTACAAAACCG (SEQ ID NO: 224) | 297 |
| 3-a | ATCGTCCGGAACTGACGCCGCACCGCTTCATCCCGAACCCGTTTCAGACCGATTGCGAAAAACAGCTGGG TATCAACTCTCTGATGTACAAAACCGGTGATCTGGCTCGCTGGCTCCCGAACGGTGAAGTTGAATACCTGG GCCGTGCGGATTTCCAGATCAAACTGCGCGGTATTCGTATTGAGCGGGCGAAATCGAGACTATGCTGGC GATGTATCCGCGCGTTCGTACCTCCCTGGTGGTTTCCAAGAAATTACGTAACGGTCCTGAAGAAACAACG AACGAACACCTGGTAG (SEQ ID NO: 225) | 297 |
| 3-b | CGGATTTCCAGATCAAACTGCGCGGTATTCGTATTGAGCCGGGCGAAATCGAGACTATGCTGGCGATGTA TCCGCGCGTTCGTACCTCCCTGGTGGTTTCCAAGAAATTACGTAACGGTCCTGAAGAAACAACGAACGAA CACCTGGTAGGCTACTACGTATGCGACTCCGCATCTGTTTCCGAAGCGGATCTGCTGTCCTTCCTGGAGAA GAAGCTGCCGCGTTATATGATTCCGACTCGTCTGGTACAGCTGAGCCAGATCCCGGTTAACGTCAACGGTA AAGCCGATCTGCGTG (SEQ ID NO: 226) | 297 |
| 3-c | TTCCTGGAGAAGAAGCTGCCGCGTTATATGATTCCGACTCGTCTGGTACAGCTGAGCCAGATCCCGGTTAA CGTCAACGGTAAAGCCGATCTGCGTGCTCTGCCGGCGGTTGATATCTCCAACAGCACCGAAGTTCGTTCTG ATCTGCGTGGTGATACCGAAATTGCCCTCGGCGAAATCTGGGCGGACGTGCTGGGCGCGCGTCAGCGTTC GGTTAGCCCGTAACGATAACTTTTTCCGCCTCGGTGGCCACTCTATCACCTGCATCCAGCTGATTGCGCGTA TCCGTCAGCGTCAGC (SEQ ID NO: 227) | 298 |
| 4-a | ACCTGCATCCAGCTGATTGCGCGTATCCGTCAGCGTCAGCGTTTGTCTGTGTCTATCTCTGTGGAAGACGT GTTTGCTACACGCACTCTTGAGCGTATGGCCGACCTGTTGCAAAACAAACAGCAAGAGAAATGCGACAAA CCACACGAAGCACCGACTGAACTGCTTGAAGAAAACGCTGCGACTGATAACATCTACCTGGCGAACAGCC TGCAGCAAGGTTTCGTCTACCATTACCTGAAAAGCATGAACAAAGTGATGCTTATGTAATGCAGAGCGT TCTGCGTTACAACACCACCCTTTCCC (SEQ ID NO: 228) | 307 |
| 4-b | CATGGAACAAAGTGATGCTTATGTAATGCAGAGCGTTCTGCGTTACAACACCACCCTTTCCCCGGATCTGT TCCAGCGTGCCTGGAAACACGCGCAGCAAAGCTTCCCGGCTCTGCGTCTGCGCTTCTCTTGGGAAAAAGA AGTCTTCCAGCTGCTGGA (SEQ ID NO: 229) | 159 |
| 4-c | AAAGCTTCCCGGCTCTGCGTCTGCGCTTCTCTTGGGAAAAAGAAGTCTTCCAGCTGCTGGATCAGGACCCG CCTCTGGACTGGCGTTTCCTCTACTTCACTGATGTGGCGGCTGGTGCAGTAGAAGACCGTAAACTGGAAGA TTTACGCC (SEQ ID NO: 230) | 150 |
| 4-d | CTGGTGCAGTAGAAGACCGTAAACTGGAAGATTTACGCCGCCAGGACCTCACCGAGCGTTTTAAACTGGA TGTGGGCCGTCTGTTTCGCGTTTACCTGATCAAACACAGCGAAAACCGTTTCACTTGTCTGTTCTCTTGTCA CCACGCTATCCTGGACGGCTGGTCCTTACCGCTTCTGTTCGAAAAA (SEQ ID NO: 231) | 188 |
| 4-e | CGTTTACCTGATCAAACACAGCGAAAACCGTTTCACTTGTCTGTTCTCTTGTCACCACGCTATCCTGGACG GCTGGTCCTTACCGCTTCTGTTCGAAAAAGTACACGAAACATACCTGCAACTGCTGCACGGCGATAACCTG ACCTCCTCTATGGATGATCCATACACCCGTACCCAACGCTACCTGCATGCGCACCGCGAAGATCACCTCGA CTTTTGGGCTGGCGTGGTGCAGAAAATCAACGAACGTTGCGATATGAATGCTCTGTTAAACGAACGCAGC CGCTATAAAGTGCAGCT (SEQ ID NO: 232) | 300 |
| 4-f | TGCTCTGTTAAACGAACGCAGCCGCTATAAAGTGCAGCTGGCCGACTACGATCAGGTACAGGAACAGCGT CAGCTGACGATCGCTCTGAGCGGTGACGCGTGGCTGGCGGATCTGCGCCAGACATGCAGTGCGCAGGGCA TCAGCTGCACTCTATCCTGCAATTTGTATGGCATGCAGTTCTGCATGCCTACGGTGGCGGTACTCACACT ATCACTGGCACCACTATTTCTGGTCGCAA (SEQ ID NO: 233) | 240 |
| 5-a | ACGGTGGCGGTACTCACACTATCACTGGCACCACTATTTCTGGTCGCAACCTCCCGATCCTGGGTATCGAG CGTGCGGTAGGCCCGTACATTAACACCCTGCCGTTAGTGTTGGACCATTCTACTTTTAAAGACAAGACGAT CATGGAAGCTATTGAAGACGTCCAAGCGAAGGTGAATGTTATGAACTCCCGTGGTAATGTAGAACTGGGT CGCCTGCACAAAACCGACCTGAAACATGGCCTGTTCGATTCTCTGTTTGTGCTGGAAAACTATCCAAACC (SEQ ID NO: 234) | 282 |

TABLE 3-continued

Sequences of daughter fragments obtained after Type IIS restriction enzyme digestion or nested PCR

| Fragment (Daughter fragment) | Sequence (5' → 3') | Expected length (bp) |
|---|---|---|
| 5-b | GCTATTGAAGACGTCCAAGCGAAGGTGAATGTTATGAACTCCCGTGGTAATGTAGAACTGGGTCGCCTGC ACAAAACCGACCTGAAACATGGCCTGTTCGATTCTCTGTTTGTGCTGGAAAACTATCCAAACCTGGATAAA TCCCGTACTCTGGAGCACCAAACTGAACTGGGTTACTCCATCGAGGGTGGTACCGAAAAACTGAACTATC CGCTGGCGGTGATTGCTCGTGAGGTTGAGACCACTGGCGGCTTTACTGTTAGCATCTGCTATGCGAGCGAA CTGTTTGAAGAGGTGA (SEQ ID NO: 235) | 298 |
| 5-c | AACTGAACTATCCGCTGGCGGTGATTGCTCGTGAGGTTGAGACCACTGGCGGCTTTACTGTTAGCATCTGC TATGCGAGCGAACTGTTTGAAGAGGTGATGATCAGCGAGCTTCTCCATATGGTACAGGATACCCTGATGC AGGTTGCACGCGGGCTCAACGAACCTGTGGGCTCCCTGGAATACCTGTCTTCCATCCAGTTAGAGCAGCTG GCAGCGTGGAACGCCACCGAAGCGGAGTTCCCGGACACGACCCTGCATGAAATGTTCGAGAACGAAGCA TCTCAAAAGCCGGATAA (SEQ ID NO: 236) | 298 |
| 5-d | TTAGAGCAGCTGGCAGCGTGGAACGCCACCGAAGCGGAGTTCCCGGACACGACCCTGCATGAAATGTTCG AGAACGAAGCATCTCAAAAGCCGGATAAAATTGCAGTCGTGTACGAAGAAACCTCTCTGACCTATCGCGA GCTGAACGAACGTGCCAATCGCATGGCGCACCAGCTGCGTTCCGACGTTTCTCCGAACCCGAACGAAGTG ATCGCGCTGGTTATGGACAAGAGTGAACACATGATCGTAAATATCTTGGCTGTGTGGAAATCTGGTGGCG CATACGTGCCGATCGATC (SEQ ID NO: 237) | 298 |
| 5-e | GAGTGAACACATGATCGTAAATATCTTGGCTGTGTGGAAATCTGGTGGCGCATACGTGCCGATCGATCCG GCTACCCGAATGACCGTATTCAGTATATCCTCGAGGACACTCAGGCGTTGGCTGTTATCGCAGATTCTTG TTACCTGCCTCGTATCAAAGGTATGGCCGCGTCTGGTACGCTGCTCTACCCGTCTGTCCTGCCGGCAAACC CAGACAGCAAATGGTCTGTGTCAAACCCGTCGCCGCTGTCTCGTAGCACCGACCTG (SEQ ID NO: 238) | 268 |
| 5-f | CGTCTGGTACGCTGCTCTACCCGTCTGTCCTGCCGGCAAACCCAGACAGCAAATGGTCTGTGTCAAACCCG TCGCCGCTGTCTCGTAGCACCGACCTGGCATACATCATCTACACCTCTGGCACCACCGGCCGCCCGAAAGG CGTGACTGTGGAGCATCACGGTGTGGTGAACCTGCAGGTATCCTGAGCAAAGTTTTTGGTCTGCGTGACA CCGACGACGAAGTCATCCTGTCTTTTTTCTAACTACGTTTTCGATCACTTCGTAGAACAGATGACTGATGCT ATCCTGAACGGGC (SEQ ID NO: 239) | 297 |
| 6-a | CTAACTACGTTTTCGATCACTTCGTAGAACAGATGACTGATGCTATCCTGAACGGGCAGAGCTGCTGGTT CTGAACGATGGTATGCGTGGTGACAAAGAACGCCTGTACCGCTACATCGAAAAGAACCGTGTAACTTATC TGTCTGGTACTCCATCTGTGGTGTCTATGTATGAGTTCAGCCGTTTCAAAGACCACCTGCGCCGCGTCGAT TGCGTCGGTGAAGCTTTCAGCGAGCCGGTCTTCGACAAAATCCGTGAA (SEQ ID NO: 240) | 260 |
| 6-b | ACCTTCCACGGTTTGGTTATCAATGGTTATGGCCCAACTGAAGTTAGCATCACTACCCATAAGCGTTTATA CCCTTTCCCAGAGCGCCGCATGGATAAGTCGATCGGCCAGCAGGTCCACAACTCTACTAGCTACGTACTG AATGAAGATATGAAGCGTACCCCGATCGGTGCTGTGGGTGAGCTGTACCTG (SEQ ID NO: 241) | 192 |
| 6-c | TGAATGAAGATATGAAGCGTACCCCGATCGGTGCTGTGGGTGAGCTGTACCTGGGCGGTGAAGGTGTTGT CCGCGGTTATCATAATCGTGCGGATGTTACCGCGAGCGCTTCATCCCGAACCCGTTCCAGTCTGAGGAAG ATAAACGTGAAGGCCGTAACAGTCGCCTGTACAAGACGGGTGATCTGGTTCGCTGGATCCCGGGTAGCTC CGGCGAAGTCGAATACCTGGGTCGCAATGACTTCCAGGTTAAGATTCG (SEQ ID NO: 242) | 259 |
| 6-d | CGAAGTCGAATACCTGGGTCGCAATGACTTCCAGGTTAAGATTCGCGGCCTCCGTATCGAGCTGGGTGAA ATCGAAGCGATCCTGAGCAGCTACCACGGCATTAAACAGAGCGTAGTGATCGCAAAAGACTGCCGTGAG GGGGCACAGAAATTCCTGGTCGGCTATTACGTTGCAGACGCTGCCCTGCCGTCCGCAGCGATCCGTCGTTT CATGCAGTCGCGCCTCCCGGGTTACATGGTTCCGTCCCGTCTGATCCTGGTTTCTAAATTCCCTGTTACTCC GTCCGGGAAGCTGGA (SEQ ID NO: 243) | 297 |
| 6-e | CGTCTGATCCTGGTTTCTAAATTCCCTGTTACTCCGTCCGGGAAGCTGGACACCAAAGCACTGCCGCCGGC GGAGGAAGAAAGCGAAATCGACGTTGTTCCACCGCGCTCCGAAATTGAGCGTTCTCTCTGCGACATCTGG GCTGAACTGCTGGAAATGCACCCGGAAGAAATCGGCATTTACTCTGACTTCTTCTCCTTGGGCGGCGACAG CCTGAAATCTACTAAGTTATCCTTCATGATCCATGAGTCCTTTAACCGTGCTGTGAGCGTTAGCGCGTTATT CTGCCATCGCACA (SEQ ID NO: 244) | 297 |
| 7-a | TCCTTCATGATCCATGAGTCCTTTAACCGTGCTGTGAGCGTTAGCGCGTTATTCTGCCATCGCACAGTTGA AGCTCAAACTCACCTGATCTTGAACGACGCAGCAGATGTACACGAAATTACCCCGATCGATTGCAACGAC ACCCAGATG (SEQ ID NO: 245) | 150 |
| 7-b | GAAGCTCAAACTCACCTGATCTTGAACGACGCAGCAGATGTACACGAAATTACCCCGATCGATTGCAACG ACACCCAGATGATCCCGGTTTCCCGTGCACAGGAACGTCTGCTGTTCATTCATGAATTCGAAAACGGTTCT AACGCTTACAACATTGACGCGGCTTTCGAACTGCCAGGTTCTGTGGACGCGAGCCTGCTGGAACAGGCCC TTCGTGGCAACCTGGCACGTCACGAAGCACTGCGCACCCTGCTGGTTAAAGATCACGCCACTGGTATTTAC CTGCAGAAAGTACTG (SEQ ID NO: 246) | 297 |
| 7-c | AGGAACGTCTGCTGTTCATTCATGAATTCGAAAACGGTTCTAACGCTTACAACATTGACGCGGCTTTCGAA CTGCCAGGTTCTGTGGACGCGAGCCTGCTGGAACAGGCCCTTCGTGGCAACCTGGCACGTCACGAAGCAC TGCGCACCCTGCTGGTTAAAGATCACGCCACTGGTATTTACCTGCAGAAAGTACTGAGTCCGGACGAAGC | 297 |

TABLE 3-continued

Sequences of daughter fragments obtained after Type IIS restriction enzyme digestion or nested PCR

| Fragment (Daughter fragment) | Sequence (5' → 3') | Expected length (bp) |
|---|---|---|
| | GCAAGGTATGTTTTCTGTTAATGTAGATACTGCTAAACAGGTTGAACGTCTGGATCAGGAAATTGCTTCTC TGTCTCAGCACGTCT (SEQ ID NO: 247) | |
| 7-d | TTGAACGTCTGGATCAGGAAATTGCTTCTCTGTCTCAGCACGTCTTCCGCCTGGACGACGAACTGCCGTGG GAGGCGCGCATCCTGAAACTGGAATCTGGCGGTCTGTACCTGATCTTGGCCTTCCACCACACCTGCTTCGA TGCATGGAGCCTGAAAGTTTTCGAACAGGAGCTGCGCGCGTCTGTACGCAGCGCTTCAGAAAACGAAATCT GCAGCGAACTTACCGGCATTAAAAGCACAGTATAAGGAATACGCTCTGTACCACCGCCGCCAGCTTAGCG GCGACCGCATGCGTAA (SEQ ID NO: 248) | 298 |
| 7-e | AATACGCTCTGTACCACCGCCGCCAGCTTAGCGGCGACCGCATGCGTAACCTGTCCGATTTCTGGTTACGT AAACTGATCGGTCTGGAACCACTGCAGCTGATCACCGATCGTCCGCGTCCGGTTCAGTTCAAATACGACG GTGACGATCTGAGCATCGAACTGTCCAAGAAAGAGACCGAAAACCTGCGCGGCGTTGCAAAACGTTGTAA GTCTTCCTTATATGTTGTACTGGTATCTGTTTACTGTGTCATGCTGGCAAGCTACGCCAACCAGAGCGATGT TAGCGTGGGCAT (SEQ ID NO: 249) | 295 |
| 7-f | TGATCACCGATCGTCCGCGTCCGGTTCAGTTCAAATACGACGGTGACGATCTGAGCATCGAACTGTCCAA GAAAGAGACCGAAAACCTGCGCGGCGTTGCAAAACGTTGTAAGTCTTCCTTATATGTTGTACTGGTATCTG TTTACTGTGTCATGCTGGCAAGCTACGCCAACCAGAGCGATGTTAGCGTGGGCATCCCAGTATCACACCGT ACGCACCCGCAGTTCCAGTCTGTTATCGGCTTTTTCGTTAACCTGGTCGTTCTGCGTGTAGATATCAGCCAG TCCGCTATTTGCG (SEQ ID NO: 250) | 297 |
| 8-a | GGTCGTTCTGCGTGTAGATATCAGCCAGTCCGCTATTTGCGGTTTAATCCGTCGCGTCATGAAAGAACTGG TTGACGCGCAGCTGCACCAGGATATGCCGTTCCAGGAAGTTACGAAACTGCTGCAG (SEQ ID NO: 251) | 127 |
| 8-b | GCCGTTCCAGGAAGTTACGAAACTGCTGCAGGTGGATAACGATCCTAGCCGTCACCCGTTGGTTCAGAAC GTATTTAACTTTGAGTCTCGCGCGAACGGTGAACACGATGCCCGCTCTGAAGACGAGGGCTCTCTTGCATT CAATCAGTACCGTCCGGTTCAGCCGGTTGACAGCGTGGCCAAATTCGATCTGAACGCCACCGTCACCGAA CTGGAATCCGGTCTGCGTGTTAATTTCAACTACGCGACCAGCTTATTCAATAAATCCACCATCCAGGGCTT CCTGCACACATATGAA (SEQ ID NO: 252) | 298 |
| 8-c | CCAGCTTATTCAATAAATCCACCATCCAGGGCTTCCTGCACACATATGAATACCTTCTGCGTCAGCTGTCC GAACTGAGCGCTGAAGGCATCAACGAAGATACCCAGCTGTCACTGGTTCGCCCGACTGAGAACGGGGATC TGCACCTGCCACTGGCCCAGTCTCCGCTCGCGACCACTGCAGAAGAACAGAAAGTTGCTTCCCTGAACCA GGCTTTCGAACGTGAAGCCTTCCTGGCGGCGGAAAAAAATCGCCGTTGTTCAAGGGGACCGCGCTCTGTCG TATGCCGACCTGAAC (SEQ ID NO: 253) | 296 |
| 8-d | GCCGTTGTTCAAGGGGACCGCGCTCTGTCGTATGCCGACCTGAACGGTCAGGCTAATCAACTGGCGCGTT ATATCCAGTCCGTCTCCTGCATCGGTGCCGACGACGGCATCGCCCTGATGCTGGAAAAGAGCATCGATAC TATCATCTGCATTCTGGCAATCTGGAAAGCAGGCGCCGCGTATGTGCCGCTGGATCCGACCTACCCACCAG GCCGTGTACAACTGATCCTGGAGGAAATCAAAGCGAAAGCTGTGCTGGTACACTCTTCCCACGCCTCTAA ATGTGAACGTCACGGTGC (SEQ ID NO: 254) | 299 |
| 9-a | CCTCTAAATGTGAACGTCACGGTGCCAAAGTCATTGCAGTAGACTCTCGGCTATTGAAACGGCAGTGAG CCAGCAGTCTGCAGCTGATCTGCCGACCATTGCTAGCCTGGGTAATCTGGCATATATCATCTTTACTAGCG GCACTTCTGGCAAACCGAAAGGCGTTCTGGTAGAGCAAAAAGCCGTTCTGCTGCTGCGCGACGCCCTGCG TGAGCGTTACTTCG (SEQ ID NO: 255) | 225 |
| 9-b | ATCTTTACTAGCGGCACTTCTGGCAAACCGAAAGGCGTTCTGGTAGAGCAAAAAGCCGTTCTGCTGCTGC GCGACGCCCTGCGTGAGCGTTACTTCGGTCGTGATTGTACCAAACATCACGGTGTTCTGTTCCTGAGCAAC TACGTTTTCGACTTCTCCGTAGAACAGCTGGTTCTGTCTGTACTCTCAGGCCACAAACTGATTGTCCCGCCG GCGGAGTTTGTGGCGGATGACGAATTCTATCGTATGGCCTCTACCCACGGTCTTTCTTACCTGTCTGGCAC CCCGAGCCTGCTT (SEQ ID NO: 256) | 297 |
| 9-c | TTCGACTTCTCCGTAGAACAGCTGGTTCTGTCTGTACTCTCAGGCCACAAACTGATTGTCCCGCCGGCGGA GTTTGTGGCGGATGACGAATTCTATCGTATGGCCTCTACCCACGGTCTTTCTTACCTGTCTGGCACCCCGA GCCTGCTTCAAAAAATCGATCTGGCACGTCTGGATCACCTGCAGGTTGTAACCGCGGCGGGTGAGGAACT CCACGCGACCCAGTACGAAAAAATGCGTCGTCGTTTTAACGGTCCAATCTACAACGCTTATGGTGTTACCG AGACAACGGTGTAC (SEQ ID NO: 257) | 297 |
| 9-d | GGTCCAATCTACAACGCTTATGGTGTTACCGAGACAACGGTGTACAACATCATCGCTGAATTCACCACCA ACTCCATCTTCGAAAACGCATTACGCGAAGTCCTGCCGGGCACCCGTGCGTACGTTCTGAACGCGGCGCT GCAGCCGGTTCCATTCGACGCGTGTGGGTGAACTGTATCTGGCCGGCGATAGCGTAACCCGTGGTTACCTGA ACCAGCCGTTGCTGACCGATCAGCGTTTCATCCCTAACCCGTTCTGCAAGGAAGAAGACATCGCGATGGG TCGTTTCGCTCGTCGTCTGT (SEQ ID NO: 258) | 298 |

TABLE 3-continued

Sequences of daughter fragments obtained after Type IIS restriction enzyme digestion or nested PCR

| Fragment (Daughter fragment) | Sequence (5' → 3') | Expected length (bp) |
|---|---|---|
| 9-e | AAACCGGCGACCTGGTTCGCTCTCGCTTCAACCGCCAGCAGCAGCCGCAGCTGGAATACCTGGGCCGTGG CGACCTGCAGATTAAAATGCGTGGTTACCGCATTGAAATTAGCGAAGTACAGAACGTGCTGACCTCCTCC CCGGGCGTACGCGAAGGTGCGGTTGTGGCTAAATATGAAAACAACGACACGTATAGCCGTACTGCACATT CCTTAGTCGGTTATTATACCACTGATAACGAAACAGTTTCAGAAGCTGATATCCTCACCTTCATGAAAGCG CGTCTGCCGACCTATA (SEQ ID NO: 259) | 297 |
| 9-f | CTAACCCGTTCTGCAAGGAAGAAGACATCGCGATGGGTCGTTTCGCTCGTCTGTACAAAACCGGCGACCT GGTTCGCTCTCGCTTCAACCGCCAGCAGCAGCCG (SEQ ID NO: 260) | 104 |
| 9-g | TACTGCACATTCCTTAGTCGGTTATTATACCACTGATAACGAAACAGTTTCAGAAGCTGATATCCTCACCT TCATGAAAGCGCGTCTGCCGACCTATATGGTGCCTTCTCACCTGTGCTGCCTGGAAGGTGCTCTGCCAGTC ACTATTAACGGTAAACTGGACGTTCGTCGTCTGCCTGAAATTATCAACGACAGTGCGCAATCCTCATATTC CCCGCCGCGCAACATTATCGAAGCGAAAATGTGCCGTTTATGGGAAAGCGCGCTGGGTATGGAACGCTGC GGTATTGACGATGAC (SEQ ID NO: 261) | 298 |
| 10-a | CGTTTATGGGAAAGCGCGCTGGGTATGGAACGCTGCGGTATTGACGATGACCTCTTCAAGCTGGGGGGGG ATTCTATCACCAGTCTGCACCTCGTCGCACAGATTCACAATCAGGTGGGCTGTAAGATTACCGTGCGCGAT ATTTTCGAACACCGTACCGCGCGTGCTCTCCACGATCACGTTTTCATGAAGGATAGC (SEQ ID NO: 262) | 198 |
| 10-b | GTACCGCGCGTGCTCTCCACGATCACGTTTTCATGAAGGATAGCGATCGCTCTAACGTCACCCAGTTCCGT ACCGAGCAGGGGCGGTCATTGGCGAAGCTCCGCTGCTGCCGATCCAGGATTGGTTCTTGAGCAAAGCTC TGCAGCACCCTATGTACTGGAACCACACGTTCTACGTACGTACCCCGGAACTGGACGTTGATTCCCTGAGT GCGGCCGTTCGTGACCTGCAGCAGTACCACGACGTTTTCCGCATGCGCCTGAAACGCGAAGAAGTTGGCT TTGTACAGTCCTTTG (SEQ ID NO: 263) | 297 |
| 10-c | TTTCCGCATGCGCCTGAAACGCGAAGAAGTTGGCTTTGTACAGTCCTTTGCCGAAGACTTTTCCCCGGCGC AGCTGCGTGTACTGAACGTGAAGGACGTGGATGGTAGCGCGGCGGTTAACGAAATCCTGGACGGTTGGCA AAGCGGCTTCAACCTGGAAAACGGTCCGATCGGCTCGATCGGTTATCTGCATGGCTATGAAGACCGCTCC GCACGTGTGTGGTTTTCTGTACACCACATGGCCATTGACACTGTTTCCTGGCAGATCCTGGTTCGTGATCTG CAGACTCTGTACCGT (SEQ ID NO: 264) | 298 |
| 10-d | ACCTGGAAAACGGTCCGATCGGCTCGATCGGTTATCTGCATGGCTATGAAGACCGCTCCGCACGTGTGTG GTTTTCTGTACACCACATGGCCATTGACACTGTTTCCTGGCAGATCCTGGTTCGTGATCTGCAGACTCTGTA CCGTAACGGTTCCCTGGGTTCCAAAGGTTCTTCATTTCGCCAATGGGCCGAGGCAATCCAAAACTACAAA GCGAGCGACTCGAACGTAACCATTGGAACAAGCTGGTTATGGAAACTGCATCGTCGATCAGCGCGCTGC CGACCTCCACTGGTTC (SEQ ID NO: 265) | 298 |
| 10-e | AAAACTACAAAGCGAGCGACTCGGAACGTAACCATTGGAACAAGCTGGTTATGGAAACTGCATCGTCGAT CAGCGCGCTGCCGACCTCCACTGGTTCTCGCGTACGTCTCTCCCGTTCTCTGTCTCCTGAAAAAACTGCTTC TCTGATCCAGGGTGGCATCGATCGTCAGGATGTAAGCGTATACGATTCTCTGCTGACTTCTGTTGGCCTGG CTTTGCAACACATCGCGCCGACTGGCCCGTCTATGGTTACAATCGAGGGTCACGGCCGCGAAGAAGTTGA CCAGACCCTGGATG (SEQ ID NO: 266) | 297 |
| 10-f | TTCTGTTGGCCTGGCTTTGCAACACATCGCGCCGACTGGCCCGTCTATGGTTACAATCGAGGGTCACGGCC GCGAAGAAGTTGACCAGACCCTGGATGTTTCTCGTACGATGGGCTGGTTCACTACCATGTATCCGTTCGAA ATCCCGCGTCTGTCGACGGAAAACATCGTGCAGGGTGTTGTTGCTGTAAGTGAACGCTTCCGCCAAGTTCC GGCTCGCGGTGTTGGTTATGGTACTCTGTACGGTTACACCCAGCACCCTCTGCCGCAGGTTACTGTTAACT ACCTGGGCCAGCTG (SEQ ID NO: 267) | 298 |
| 11-a | ACACCCAGCACCCTCTGCCGCAGGTTACTGTTAACTACCTGGGCCAGCTGGCTCGTAAACAGAGCAAGCC GAAAGAATGGGTTCTGGCAGTTGGTGATAACGAGTTCGAGTACGGTCTGATGACCTCCCCGGAGGATAAG GACCGTTCGAGCTCCGCAGTGGATGTTACGGCCGTCTGCATCGACGGGACGATGATCATCGATGTGGACT CGGCTTGGTCTTTGGAAGAATCTGAACAGTTCATCTCGTCAATTGAAGAAGGTCTGAACAAATCCTGGA CGGTCGTGCATCCCAGC (SEQ ID NO: 268) | 297 |
| 11-b | CGTAAACAGAGCAAGCCGAAAGAATGGGTTCTGGCAGTTGGTGATAACGAGTTCGAGTACGGTCTGATGA CCTCCCCGGAGGATAAGGACCGTTCGAGCTCCGCAGTGGATGTTACGGCCGTCTGCATCGACGGGACGAT GATCATCGATGTGGACTCGGCTTGGTCTTTGGAAGAATCTGAACAGTTCATCTCGTCAATTGAAGAAGGTC TGAACAAATCCTGGACGGTCGTGCATCCCAGCAGACTAGCCGCTTTCCGGATGTGCCGCAGCCAGCAGA GACCTACACCCCATAC (SEQ ID NO: 269) | 297 |
| 11-c | GATGTGGACTCGGCTTGGTCTTTGGAAGAATCTGAACAGTTCATCTCGTCAATTGAAGAAGGTCTGAACA AATCCTGGACGGTCGTGCATCCCAGCAGACTAGCCGCTTTCCGGATGTGCCGCAGCCAGCAGAGACCTA CACCCCATACTTCGAATATCTGGAACCGCCGCGCCAGGGCCCGACCCTGTTTCTGCTGCCACCGGGTGAAG GTGGTGCGGAATCTTACTTCAACAACATCGTCAAACGCTTGCGTCAAACTAACATGGTTGTCTTTAACAAC TACTACCTGCACTCC (SEQ ID NO: 270) | 297 |

TABLE 3-continued

Sequences of daughter fragments obtained after Type IIS restriction enzyme digestion or nested PCR

| Fragment (Daughter fragment) | Sequence (5' → 3') | Expected length (bp) |
|---|---|---|
| 11-d | GAATATCTGGAACCGCCGCGCCAGGGCCCGACCCTGTTTCTGCTGCCACCGGGTGAAGGTGGTGCGGAAT CTTACTTCAACAACATCGTCAAACGCTTGCGTCAAACTAACATGGTTGTCTTTAACAACTACTACCTGCAC TCCAAACGTCTGCGCACCTTCGAGGAACTGGCTGAAATGTATCTGGACCAGGTACGCGGCATCCAACCGC ACGGTCCATACCACTTCATCGGCTGGAGCTTCGGGGGCATTCTGGCGATGGAGATGTCCCGTCGTCTGGTT GCGAGCGACGAAAA (SEQ ID NO: 271) | 296 |
| 11-e | GGCATTCTGGCGATGGAGATGTCCCGTCGTCTGGTTGCGAGCGACGAAAAAATTGGTTTTCTGGGTATTAT CGACACCTATTTCAACGTACGTGGTGCCACTCGCACCATTGGCCTTGGTGATACTGAAATCCTGGATCCGA TCCACCACATCTATAACCCGGACCCGGCAAACTTTCAGCGTCTGCCGTCTGCCACCGACCGTATCGTCCTG TTTAAGGCCATGCGTCCGAATAATAAATATGAATCAGAAAACCAGCGTCGCCTGTATGAGTACTACGAC (SEQ ID NO: 272) | 282 |
| 11-f | CTACGACGCGTTAGATTCCACGGACTGGACCGCATGTTACCAGGCGATCCCTACCTCCTCATGGTCGCGCC TGCGCACGATCCACACCTTCCCGGGTTCGGAAATCCACAACCGCTGGTCCCGTTGCGTTCGTCTGAGCCGT AACACCAGCCTTGCCATCGACCCGTCTCTGGCGGCTCAGTACATCGGTCGTTGGAAGTAA (SEQ ID NO: 273) | 202 |

Nested PCR for 1 kb DNA Synthesis Using Flanking Sequence Removed Shotgun Assembly Products The flanking sequence removed shotgun assembly products were assembled to make 11 gene cluster fragments (645-1,325 bp). The target DNA sequences are listed in Table 4.

TABLE 4

Sequences of 11 gene cluster fragments prepared by the methods of the present disclosure

| Fragment | Targeted sequence after restriction enzyme or nested PCR (5' → 3') | Expected length (bp) |
|---|---|---|
| 1 | ATGACCCAATTGAAGCCGCCTAACGGGACCACTCCGATCGGCTTCAGCGCCACTACTAGCCTGAACGCTA GCGGCTCTTCCTCGGTTAAGAATGGTACCATCAAGCCTTCGAATGGTATCTTCAAACCTTCTACTCGTGAC ACCATGGACCCGTGCTCGGGCAACGCCGCTGACGGCTCCATTCGCGTACGTTTTCGCGGTGGCATCGAAC GTTGGAAAGAGTGTGTAAACCAAGTGCCGGAGCGTTGCGACCTGTCTGGTCTGACCACGGACAGCACCCG CTACCAGCTGGCTTCGACCGGCTTCGGCGACGCGAGCGCGGCTTACCAGGAACGTCTGATGACTGTGCCG GTAGATGTTCATGCTGCGCTCCAGGAGCTGTGCCTGGAACGCCGCGTCTCTGTGGGTTCTGTGATCAACTT CAGCGTTCACCAGATGCTGAAGGGTTTTGGCAACGGTACTCACACTATCACCGCGAGCCTGCACCGCGAA CAGAATCTGCAGAACTCCTCTCCGTCTTGGGTCGTTTCCCCTACTATCGTGACCCATGAAAACCGCGATGG CTGGTCAGTGGCGCAGGCAGTGGAGTCTATCGAGGCTGGTCGTGGCTCCGAAAAGGAATCTGTGACCGCG ATTGATTCCGGCTCCTCCCTGGTCAAAATGGGTCTGTTCGATCTGCTGGTTTCCTTCGTCGATGCGGATGAC GCGCGTATCCCTTGCTTCGACTTTCCGCTGGCTGTTATTGTGCGCGAGTGCGATGCAAACCTGTCTCTCACC CTTCGCTTCTCGGACTGCCTGTTCAACGAGGAAACCATTTGTAATTTCACGGATGCCCTCAATATCCTGTTG GCTGAGGCAGTTATCGGTCGTGTAACTCCGGTAGCCGATATCGAGCTGCTGTCTGCAGAGCAGAAACAAC AGCTGGAGGAATGGAACAACACCGATGGTGAATATCCGTCTAGCAAGCGTCTGCACCACCT (SEQ ID NO: 274) | 980 |
| 2 | GTGAATATCCGTCTAGCAAGCGTCTGCACCACCTGATTGAAGAGGTGGTGGAACGTCACGAAGACAAAAT CGCTGTGGTGTGCGACGAACGTGAACTGACTTACGGTGAACTCAATGCCCAGGGCAACTCCCTGGCGCGT TACCTGCGCAGCATTGGTATTCTGCCTGAACAGCTGGTTGCGCTGTTTCTGGACAAATCCGAAAAATTGAT CGTAACCATCCTGGGCGTCTGGAAATCCGGTGCTGCTTACGTGCCAATTGACCCGACCTACCCTGACGAAC GTGTTCGTTTCGTTCTGGACGACACGAAAGCCCGTGCGATTATCGCTTCCAATCAGCATGTTGAACGCCTC CAGCGTGAAGTAATCGGTGATCGCAACCTGTGCATCATCCGTCTCGAACCACTGCTGGCGAGCCTTGCGC AGGATTCTTCTAAATTCCCTGCCCACAACCTGGATGATTTGCCGCTGACCAGCCAGCAGCTGGCGTACGTT ACTTATACCAGCGGTACCACCGGCTTTCCGAAAGGCATTTTCAAACAGCACACTAACGTTGTTAACTCCAT CACAGACCTGTCCGCTCGTTACGGTGTTGCAGGTCAACACCATGAAGCTATCCTGCTCTTCAGTGCTTGCG TTTTCGAACCGTTCGTTCGTCAGACTCTGATGGCCCTGGTGAACGGTCACCTGCTCGCCGTGATTAACGAT GTAGAAAAATATGACGCTGACACCCTCCTCCCATTTATCCGCCGTCACTCTATCACCTATCTGAACGGTAC TGCGTCGGTTCTCCAAGAGTATGACTTCTCTGACTGTCCGAGCCTGAACCGTATCATCCTGGTGGGCGAGA ACCTGACCGAAGCACGTTACCTGGCACTGCGTCAGCGTTTCAAAAATCGTATTCTGAACGAGTACGGTTTC ACCGAGTCTGCGTTCGTGACTGCGCTGAAAATTTTCGATCCGGAAAGCACCCGCAAAGATACCTCCCTGG GGCGTCCGGTGCGCAATGTTAAATGCTATATCTTGAACCCTAGCCCTGAAACGCGTGCCAATTGGTGCTACA | 1203 |

TABLE 4-continued

Sequences of 11 gene cluster fragments prepared by the
methods of the present disclosure

| Fragment | Targeted sequence after restriction enzyme or nested PCR (5' → 3') | Expected length (bp) |
|---|---|---|
| | GGTGAGCTGCATATTGGCGGCCTGGGTATCTCCAAGGGTTACTTGAATCGTCCGGAACTGACGCCGCACC<br>GCTTCATCCCGAACCCGTTTCAGACCGATTGCGAAAAACAGCTGGGTATCAACTCTCTGATGTACAAAACC<br>G (SEQ ID NO: 275) | |
| 3 | ATCGTCCGGAACTGACGCCGCACCGCTTCATCCCGAACCCGTTTCAGACCGATTGCGAAAAACAGCTGGG<br>TATCAACTCTCTGATGTACAAAACCGGTGATCTGGCTCGCTGGCTCCCGAACGGTGAAGTTGAATACCTGG<br>GCCGTGCGGATTTCCAGATCAAACTGCGCGGTATTCGTATTGAGCCGGGCGAAATCGAGACTATGCTGGC<br>GATGTATCCGCGCGTTCGTACCTCCCTGGTGGTTTCCAAGAAATTACGTAACGGTCCTGAAGAAACAACG<br>AACGAACACCTGGTAGGCTACTACGTATGCGACTCCGCATCGTGTTTCCGAAGCGGATCTGCTGTCCTTCCT<br>GGGAGAAGAAGCTGCCGCGTTATATGATTCCGACTCGTCTGGTACAGCTGAGCCAGATCCCGGTTAACGTC<br>AACGGTAAAGCCGATCTGCGTGCTCTGCCGGCGGTTGATATCTCCAACAGCACCGAAGTTCGTTCTGATCT<br>GCGTGGTGATACCGAAATTGCCCTCGGCGAAATCTGGGCGGACGTGCTGGGCGCGCGTCAGCGTTCGGTT<br>AGCCGTAACGATAACTTTTTCCGCCTCGGTGGCCACTCTATCACCTGCATCCAGCTGATTGCGCGTATCCG<br>TCAGCGTCAGC (SEQ ID NO: 276) | 645 |
| 4 | ACCTGCATCCAGCTGATTGCGCGTATCCGTCAGCGTCAGCGTTTGTCTGTGTCTATCTCTGTGGAAGACGT<br>GTTTGCTACACGCACTCTTGAGCGTATGGCCGACCTGTTGCAAAACAAACAGCAAGAGAAATGCGACAAA<br>CCACACGAAGCACCGACTGAACTGCTTGAAGAAAACGCTGCGACTGATAACATCTACCTGGCGAACAGCC<br>TGCAGCAAGGTTTCGTCTACCATTACCTGAAAAGCATGGAACAAAGTGATGCTTATGTAATGCAGAGCGT<br>TCTGCGTTACAACACCACCCTTTCCCCGGATCTGTTCCAGCGTGCCTGGAAACACGCGCAGCAAAGCTTCC<br>CGGCTCTGCGTCTGCGCTTCTCTTGGGAAAAAGAAGTCTTCCAGCTGCTGGATCAGGACCCGCCTCTGGAC<br>TGGCGTTTCCTCTACTTCACTGATGTGGCGGCTGGTGCAGTAGAAGACCGTAAACTGGAAGATTTACGCCG<br>CCAGGACCTCACCGAGCGTTTTAAACTGGATGTGGGCCGTCGTGTTTCGCGTTTACCTGATCAAACACAGCG<br>AAAACCGTTTCACTTGTCTGTTCTCTTGTCACCACGCTATCCTGGACGGCTGGTCCTTACCGCTTCTGTTCG<br>AAAAAGTACACGAAACATACCTGCAACTGCTGCACGGCGATAACCTGACCTCCTCTATGGATGATCCATA<br>CACCCGTACCCAACGCTACCTGCATGCGCACCGCGAAGATCACCTCGACTTTTGGGCTGGCGTGGTGCAG<br>AAAATCAACGAACGTTGCGATATGAATGCTCTGTTAAACGAACGCAGCCGCTATAAAGTGCAGCTGGCCG<br>ACTACGATCAGGTACAGGAACAGCGTCAGCTGACGATCGCTCTGAGCGGTGACGCGTGGCTGGCGGATCT<br>GCGCCAGACATGCAGTGCGCAGGGCATCACGCTGCACTCTATCCTGCAATTTGTATGGCATGCAGTTCTGC<br>ATGCCTACGGTGGCGGTACTCACACTATCACTGGCACCACTATTTCTGGTCGCAA<br>(SEQ ID NO: 277) | 1043 |
| 5 | ACGGTGGCGGTACTCACACTATCACTGGCACCACTATTTCTGGTCGCAACCTCCCGATCCTGGGTATCGAG<br>CGTGCGGTAGGCCCGTACATTAACACCCTGCCGTTAGTGTTGGACCATTCTACTTTTAAAGACAAGACGAT<br>CATGGAAGCTATTGAAGACGTCCAAGCGAAGGTGAATGTTATGAACTCCCGTGGTAATGTAGAACTGGGT<br>CGCCTGCACAAAACCGACCTGAAACATGGCCTGTTCGATTCTCTGTTTGTGCTGGAAAACTATCCAAACCT<br>GGATAAATCCCGTACTCTGGAGCACCAAACTGAACTGGGTTACTCCATCGAGGGTGGTACCGAAAAACTG<br>AACTATCCGCTGGCGGTGATTGCTCGTGAGGTTGAGACCACTGGCGGCTTTACTGTTAGCATCTGCTATGC<br>GAGCGAACTGTTTGAAGAGGTGATGATCAGCGAGCTTCTCCATATGGTACAGGATACCCTGATGCAGGTT<br>GCACGCGGGCTCAACGAACCTGTGGGCTCCCTGGAATACCTGTCTTCCATCCAGTTAGAGCAGCTGGCAG<br>CGTGGAACGCCACCGAAGCGGAGTTCCCGGACACGACCCTGCATGAAATGTTCGAGAACGAAGCATCTCA<br>AAAGCCGGATAAAATTGCAGTCGTGTACGAAGAAACCTCTCTGACCTATCGCGAGCTGAACGAACGTGCC<br>AATCGCATGGCGCACCAGCTGCGTTCCGACGTTTCTCCGAACCCGAACGAAGTGATCGCGCTGGTTATGG<br>ACAAGAGTGAACACATGATCGTAAATATCTTGGCTGTGTGGAAATCTGGTGGCGCATACGTGCCGATCGA<br>TCCGGGCTACCCGAATGACCGTATTCAGTATATCCTCGAGGACACTCAGGCGTTGGCTGTTATCGCAGATT<br>CTTGTTACCTGCCTCGTATCAAAGGTATGGCCGCGTCTGGTACGCTGCTCTACCCGTCTGTCCTGCCGGCA<br>AACCCAGACAGCAAATGGTCTGTGTCAAACCCGTCGCCGCTGTCTCGTAGCACCGACCTGGCATACATCA<br>TCTACACCTCTGGCACCACCGGCCGCCCGAAAGGCGTGACTGTGGAGCATCACGGTGTGGTGAACCTGCA<br>GGTATCCCTGAGCAAAGTTTTTGGTCTGCGTGACACCGACGACGAAGTCATCCTGTCTTTTTCTAACTACG<br>TTTTCGATCACTTCGTAGAACAGATGACTGATGCTATCCTGAACGGGC (SEQ ID NO: 278) | 1245 |
| 6 | CTAACTACGTTTTCGATCACTTCGTAGAACAGATGACTGATGCTATCCTGAACGGGCAGACGCTGCTGGTT<br>CTGAACGATGGTATGCGTGGTGACAAAGAACGCCTGTACCGCTACATCGAAAAGAACCGTGTAACTTATC<br>TGTCTGGTACTCCATCTGTGGTGTCTATGTATGAGTTCAGCCGTTTCAAAGACCACCTGCGCCGCGTCGAT<br>TGCGTCGGTGAAGCTTTCAGCGAGCCGGTCTTCGACAAAATCCGTGAAACCTTCCACGGTTTGGTTATCAA<br>TGGTTATGGCCCAACTGAAGTTAGCATCACTACCCATAAGCGTTTATACCCTTTCCCAGAGCGCCGCATGG<br>ATAAGTCGATCGGCCAGCAGGTCCACAACTCTACTAGCTACGTACTGAATGAAGATATGAAGCGTACCCC<br>GATCGGTGCTGTGGGTGAGCTGTACCTGGGCGGTGAAGGTGTTGTCCGCGGTTATCATAATCGTGCGGAT<br>GTTACCGCCGAGCGCTTCATCCCGAACCCGTTCCAGTCTGAGGAAGATAAACGTGAAGGCCGTAACAGTC<br>GCCTGTACAAGACGGGTGATCTGGTTCGCTGGATCCCGGGTAGCTCCGGCGAAGTCGAATACCTGGGTCG<br>CAATGACTTCCAGGTTAAGATTCGCGGCCTCCGTATCGAGCTGGGTGAAATCGAAGCGATCCTGAGCAGC<br>TACCACGGCATTAAACAGAGCGTAGTGATCGCAAAAGACTGCCGTGAGGGGGCACAGAAATTCCTGGTCG<br>GCTATTACGTTGCAGACGCTGCCCTGCCGTCCGCAGCGATCCGTCGTTTCATGCAGTCGCGCTCCCGGGT<br>TACATGGTTCCGTCCCGTCTGATCCTGGTTTCTAAATTCCCTGTTACTCCGTCCGGGAAGCTGGACACCAA<br>AGCACTGCCGCCGGCGGAGGAAGAAAGCGAAATCGACGTTGTTCACCGCGCTCCGAAATTGAGCGTTCT<br>CTCTGCGACATCTGGGCTGAACTGCTGGAAATGCACCCGGAAGAAATCGGCATTTACTCTGACTTCTTCTC<br>CTTGGGCGGCAGCTGAAATCTACTAAGTTATCCTTCATGATCCATGAGTCCTTTAACCGTGCTGTGA<br>GCGTTAGCGCGTTATTCTGCCATCGCACA (SEQ ID NO: 279) | 1157 |
| 7 | TCCTTCATGATCCATGAGTCCTTTAACCGTGCTGTGAGCGTTAGCGCGTTATTCTGCCATCGCACAGTTGA<br>AGCTCAAAACTCACCTGATCTTGAACGACGCAGCAGATGTACACGAAATTACCCCGATCGATTGCAACGAC<br>ACCCAGATGATCCCGGTTTCCCGTGCACAGGAACGTCTGCTGTTCATTCATGAATTCGAAAACGGTTCTAA | 1066 |

TABLE 4-continued

Sequences of 11 gene cluster fragments prepared by the methods of the present disclosure

| Fragment | Targeted sequence after restriction enzyme or nested PCR (5' → 3') | Expected length (bp) |
|---|---|---|
|  | CGCTTACAACATTGACGCGGCTTTCGAACTGCCAGGTTCTGTGGACGCGAGCCTGCTGGAACAGGCCCTTC<br>GTGGCAACCTGGCACGTCACGAAGCACTGCGCACCCTGCTGGTTAAAGATCACGCCACTGGTATTTACCT<br>GCAGAAAGTACTGAGTCCGGACGAAGCGCAAGGTATGTTTTCTGTTAATGTAGATACTGCTAAACAGGTT<br>GAACGTCTGGATCAGGAAATTGCTTCTCTGTCTCAGCACGTCTTCCGCCTGGACGACGAACTGCCGTGGGA<br>GGCGCGCATCCTGAAACTGGAATCTGGCGGTCTGTACCTGATCTTGGCCTTCCACCACACCTGCTTCGATG<br>CATGGAGCCTGAAAGTTTTCGAACAGGAGCTGCGCGCGCTGTACGCAGCGCTTCAGAAAACGAAATCTGC<br>AGCGAACTTACCGGCATTAAAAGCACAGTATAAGGAATACGCTCTGTACCACCGCCGCCAGCTTAGCGGC<br>GACCGCATGCGTAACCTGTCCGATTTCTGGTTACGTAAACTGATCGGTCTGGAACCACTGCAGCTGATCAC<br>CGATCGTCCGCGTCCGGTTCAGTTCAAATACGACGGTGACGATCTGAGCATCGAACTGTCCAAGAAAGAG<br>ACCGAAAACCTGCGCGGCGTTGCAAAACGTTGTAAGTCTTCCTTATATGTTGTACTGGTATCTGTTTACTG<br>TGTCATGCTGGCAAGCTACGCCAACCAGAGCGATGTTAGCGTGGGCATCCCAGTATCACACCGTACGCAC<br>CCGCAGTTCCAGTCTGTTATCGGCTTTTTCGTTAACCTGGTCGTTCTGCGTGTAGATATCAGCCAGTCCGCT<br>ATTTGCG (SEQ ID NO: 280) |  |
| 8 | GGTCGTTCTGCGTGTAGATATCAGCCAGTCCGCTATTTGCGGTTTAATCCGTCGCGTCATGAAAGAACTGG<br>TTGACGCGCAGCTGCACCAGGATATGCCGTTCCAGGAAGTTACGAAACTGCTGCAGGTGGATAACGATCC<br>TAGCCGTCACCCGTTGGTTCAGAACGTATTTAACTTTGAGTCTCGCGCGAACGGTGAACACGATGCCCGCT<br>CTGAAGACGAGGGCTCTCTTGCATTCAATCAGTACCGTCCGGTTCAGCCGGTTGACAGCGTGGCCAAATTC<br>GATCTGAACGCCACCGTCACCGAACTGGAATCCGGTCTGCGTGTTAATTTCAACTACGCGACCAGCTTATT<br>CAATAAATCCACCATCCAGGGCTTCCTGCACACATATGAATACCTTCTGCGTCAGCTGTCCGAACTGAGCG<br>CTGAAGGCATCAACGAAGATACCCAGCTGTCACTGGTTCGCCCGACTGAGAACGGGGATCTGCACCTGCC<br>ACTGGCCCAGTCTCCGCTCGCGACCACTGCAGAAGAACAGAAAGTTGCTTCCCTGAACCAGGCTTTCGAA<br>CGTGAAGCCTTCCTGGCGGCGGAAAAAATCGCCGTTGTTCAAGGGGACCGCGCTCTGTCGTATGCCGACC<br>TGAACGGTCAGGCTAATCAACTGGCGCGTTATATCCAGTCCGTCTCCTGCATCGGTGCCGACGACGGCATC<br>GCCCTGATGCTGGAAAAGAGCATCGATACTATCATCTGCATTCTGGCAATCTGGAAAGCAGGCGCCGCGT<br>ATGTGCCGCTGGATCCGACCTACCCACCAGGCCGTGTACAACTGATCCTGGAGGAAATCAAAGCGAAAGC<br>TGTGCTGGTACACTCTTCCCACGCCTCTAAATGTGAACGTCACGGTGC (SEQ ID NO: 281) | 894 |
| 9 | CCTCTAAATGTGAACGTCACGGTGCCAAAGTCATTGCAGTAGACTCTCCGGCTATTGAAACGGCAGTGAG<br>CCAGCAGTCTGCAGCTGATCTGCCGACCATTGCTAGCGTGGGTAATCTGGCATATATCATCTTTACTAGCG<br>GCACTTCTGGCAAACCGAAAGGCGTTCTGGTAGAGCAAAAAGCCGTTCTGCTGCTGCGCGACGCCCTGCG<br>TGAGCGTTACTTCGGTCGTGATTGTACCAAACATCACGGTGTTCTGTTCCTGAGCAACTACGTTTTCGACTT<br>CTCCGTAGAACAGCTGGTTCTGTCTGTACTCTCAGGCCACAAACTGATTGTCCCGCCGGCGGAGTTTGTGG<br>CGGATGACGAATTCTATCGTATGGCCTCTACCCACGGTCTTTCTTACCTGTCTGGCACCCCGAGCCTGCTTC<br>AAAAAATCGATCTGGCACGTCTGGATCACCTGCAGGTTGTAACCGCGGCGGGTGAGGAACTCCACGCGAC<br>CCAGTACGAAAAATGCGTCGTCGTTTTAACGGTCCAATCTACAACGCTTATGGTGTTACCGAGACAACG<br>GTGTACAACATCATCGCTGAATTCACCACCAACTCCATCTTCGAAAACGCATTACGCGAAGTCCTGCCGGG<br>CACCCGTGCGTACGTTCTGAACGCGGCGCTGCAGCCGGTTCCATTCGACGCTGTGGGTGAACTGTATCTGG<br>CCGGCGATAGCGTAACCCGTGGTTACCTGAACCAGCCGTTGCTGACCGATCAGCGTTTCATCCCTAACCCG<br>TTCTGCAAGGAAGAAGACATCGCGATGGGTCGTTTCGCTCGTCTGTACAAAACCGGCGACCTGGTTCGCTC<br>TCGCTTCAACCGCCAGCAGCAGCCGCAGCTGGAATACCTGGGCCGTGGCGACCTGCAGATTAAAATGCGT<br>GGTTACCGCATTGAAATTAGCGAAGTACAGAACGTGCTGACCTCCTCCCCGGGCGTACGCGAAGGTGCGG<br>TTGTGGCTAAATATGAAAACAACGACACGTATAGCCGTACTGCACATTCCTTAGTCGGTTATTATACCACT<br>GATAACGAAACAGTTTCAGAAGCTGATATCCTCACCTTCATGAAAGCGCGTCTGCCGACCTATATGGTGCC<br>TTCTCACCTGTGCTGCCTGGAAGGTGCTCTGCCAGTCACTATTAACGGTAAACTGGACGTTCGTCGTCTGC<br>CTGAAATTATCAACGACAGTGCGCAATCCTCATATTCCCCGCCGCGCAACATTATCGAAGCGAAAATGTG<br>CCGTTTATGGGAAAGCGCGCTGGGTATGGAACGCTGCGGTATTGACGATGAC (SEQ ID NO: 282) | 1325 |
| 10 | CGTTTATGGGAAAGCGCGCTGGGTATGGAACGCTGCGGTATTGACGATGACCTCTTCAAGCTGGGGGGGG<br>ATTCTATCACCAGTCTGCACCTCGTCGCACAGATTCACAATCAGGTGGGCTGTAAGATTACCGTGCGCGAT<br>ATTTTCGAACACCGTACCGCGCGTGCTCTCCACGATCACGTTTTCATGAAGGATAGCGATCGCTCTAACGT<br>CACCCAGTTCCGTACCGAGCAGGGGCCGGTCATTGGCGAAGCTCCGCTGCTGCCGATCCAGGATTGGTTCT<br>TGAGCAAAGCTCTGCAGCACCCTATGTACTGGAACCACACGTTCTACGTACGTACCCCGGAACTGGACGT<br>TGATTCCCTGAGTGCGGCCGTTCGTGACCTGCAGCAGTACCACGACGTTTTCCGCATGCGCCTGAAACGCG<br>AAGAAGTTGGCTTTGTACAGTCCTTTGCCGAAGACTTTTCCCCGGCGCAGCTGCGTGTACTGAACGTGAAG<br>GACGTGGATGGTAGCGCGGCGGTTAACGAAATCCTGGACGGTTGGCAAAGCGGCTTCAACCTGGAAAAC<br>GGTCCGATCGGCTCGATCGGTTATCTGCATGGCTATGAAGACCGCTCCGCACGTGTGTGGTTTTCTGTACA<br>CCACATGGCCATTGACACTGTTTCCTGGCAGATCCTGGTTCGTGATCTGCAGACTCTGTACCGTAACGGTT<br>CCCTGGGTTCCAAAGGTTCTTCATTTCGCCAATGGCGCGAGGCAATCCAAAACTACAAAGCGGACGACTC<br>GGAACGTAACCATTGGAACAAGCTGGTTATGGAAACTGCATCGTCGATCAGCGCGCTGCCGACCTCCACT<br>GGTTCTCGCGTACGTCTCTCCCGTTCTCTGTCTCCTGAAAAAACTGCTTCTCTGATCCAGGGTGGCATCGAT<br>CGTCAGGATGTAAGCGTATACGATTCTCTGCTGACTTCTGTTGGCCTGGCTTTGCAACACATCGCGCCGAC<br>TGGCCCGTCTATGGTTACAATCGAGGGTCACGGCCGCGAAGAAGTTGACCAGACCCTGGATGTTTCTCGT<br>ACGATGGGCTGGTTCACTACCATGTATCCGTTCGAAATCCCGCGTCTGTCGACGGAAAACATCGTGCAGG<br>GTGTTGTTGCTGTAAGTGAACGCTTCCGCCAAGTTCCGGCTCGCGGTGTTGGTTATGGTACTCTGTACGGT<br>TACACCCAGCACCCTCTGCCGCAGGTTACTGTTAACTACCTGGGCCAGCTG (SEQ ID NO: 283) | 1251 |
| 11 | ACACCCAGCACCCTCTGCCGCAGGTTACTGTTAACTACCTGGGCCAGCTGGCTCGTAAACAGAGCAAGCC<br>GAAAGAATGGGTTCTGGCAGTTGGTGATAACGAGTTCGAGTACGGTCTGATGACCTCCCCGGAGGATAAG<br>GACCGTTCGAGCTCCGCAGTGGATGTTACGGCCGTCTGCATCGACGGGACGATGATCATCGATGTGGACT<br>CGGCTTGGTCTTTGGAAGAATCTGAACAGTTCATCTCGTCAATTGAAGAAGGTCTGAACAAAATCCTGGA<br>CGGTCGTGCATCCCAGCAGACTAGCCGCTTTCCGGATGTGCCGCAGCCAGCAGAGACCTACACCCCATAC | 1076 |

TABLE 4-continued

Sequences of 11 gene cluster fragments prepared by the methods of the present disclosure

| Frag-<br>ment | Targeted sequence after restriction enzyme or nested PCR (5' → 3') | Expected length (bp) |
|---|---|---|
| | TTCGAATATCTGGAACCGCCGCGCCAGGGCCCGACCCTGTTTCTGCTGCCACCGGGTGAAGGTGGTGCGG<br>AATCTTACTTCAACAACATCGTCAAACGCTTGCGTCAAACTAACATGGTTGTCTTTAACAACTACTACCTG<br>CACTCCAAACGTCTGCGCACCTTCGAGGAACTGGCTGAAATGTATCTGGACCAGGTACGCGGCATCCAAC<br>CGCACGGTCCATACCACTTCATCGGCTGGAGCTTCGGGGGCATTCTGGCGATGGAGATGTCCCGTCGTCTG<br>GTTGCGAGCGACGAAAAAATTGGTTTTCTGGGTATTATCGACACCTATTTCAACGTACGTGGTGCCACTCG<br>CACCATTGGCCTTGGTGATACTGAAATCCTGGATCCGATCCACCACATCTATAACCCGGACCCGGCAAACT<br>TTCAGCGTCTGCCGTCTGCCACCGACCGTATCGTCCTGTTTAAGGCCATGCGTCCGAATAATAAATATGAA<br>TCAGAAAACCAGCGTCGCCTGTATGAGTACTACGACGCGTTAGATTCCACGGACTGGACCGCATGTTACC<br>AGGCGATCCCTACCTCCTCATGGTCGCGCCTGCGCACGATCCACACCTTCCCGGGTTCGGAAATCCACAAC<br>CGCTGGTCCCGTTGCGTTCGTCTGAGCCGTAACACCAGCCTTGCCATCGACCCGTCTCTGGCGGCTCAGTA<br>CATCGGTCGTTGGAAGTAA (SEQ ID NO: 284) | |

The 11 gene cluster fragments were constructed using 3 μl water, 10 μl Phusion polymerase pre-mix (NEB, MA), 1 μl forward and reverse primers, and 5 μl of flanking sequence-cleaved shotgun assembly DNA fragments (FIG. 8i). The ~1 kb DNA fragments were cloned into the TOPO vector using the TOP Cloner™0 Blunt core kit (Enzynomics, Korea) and submitted for Sanger sequencing. A few colonies were chosen for colony PCR using M13 primer pairs (M13F-pUC and M13R-pUC universal primer pair). The Lasergene program (DNAstar, Madison, Wis.) was used to analyze the DNA sequence data.

Nested PCR Assembly of an 11.4 kb Gene Cluster Using Flanking Sequence Removed Shotgun Assembly Products A nested PCR method was used to assemble eleven ~1 kb fragments into the full-length target penicillin biosynthetic gene cluster.

The PCR was performed using eleven ~1 kb fragments (each 1 μl) and 15 μl of Phusion polymerase pre-mix (NEB, MA) in the absence of primers as follows: (a) a pre-denaturation step at 95° C. for 3 min; (b) a 10-cycle PCR step, each cycle consisting of 95° C. for 30 s, 70° C. for 30 s, and 72° C. for 3 min 30 s; and (c) a final elongation step at 72° C. for 5 min.

1 μl primer pairs containing restriction enzyme sites (BglII or NotI) were added to the mixture (~1 kb fragments (each 1 μl) and 15 μl of Phusion polymerase pre-mix) and 25 more PCR cycles were performed. The PCR products were used for cloning.

After gel-electrophoresis, bands of the desired size were excised and DNA was purified. The products were cloned into a pBK3 vector (Kim, H., et al., 2010) using BglII and NotI restriction enzymes, and C2566 E. coli competent cells were transformed with the vector. After overnight growth at 37° C., a few colonies were screened for pBK3 vector containing the desired DNA insert size using colony PCR. Several colonies were grown in LB media for plasmid extraction using an AccuPrep™ plasmid extraction kit (Bioneer, Korea). The extracted plasmid was submitted for sequencing. Sequencing data were analyzed using the Lasergene program (DNAstar, Madison, Wis., USA).

Results and Discussion

The shotgun DNA synthesis technology was developed to overcome the challenges of high-throughput DNA construction. 228 oligonucleotides were designed to construct a penicillin biosynthetic gene cluster [N-(5-amino-5-carboxypentanoyl)-L-cysteinyl-D-valine synthase, 11,376 bp]. Chip oligonucleotides were designed to contain generic flanking sequences and cleaved from a 55K Agilent DNA microchip. Selective amplification was carried out using flanking sequences and amplification primer sequences were removed using the Type IIS restriction enzymes to obtain a sub-pool of chip oligonucleotides (FIGS. 8a and 8b).

The key point for the success of the method of the present disclosure is based on the hypothesis that a pool of oligonucleotides can be shotgun assembled in one pot to produce heterogeneous assembly products, and that each one of these products can be identified by high-throughput sequencing. Thus, oligonucleotides, at least one end of which had been cleaved, were used for shotgun DNA synthesis. As expected, highly heterogeneous DNA fragments ranging in size from 100 bp to 1,000 bp were produced (FIG. 8c). DNA corresponding to the 300-500 bp region were isolated from the highly heterogeneous DNA fragments by agarose gel electrophoresis. The sizes of the DNA fragments were determined taking into consideration the limit (400-500 bp) of current 454 high-throughput sequencing read length.

The present inventors then focused on developing a method to identify random fragment compositions using high-throughput sequencing technology, as well as a method to obtain sequence-validated error-free fragments from the pool of DNA fragments (FIG. 7). In the attainment of the object stated above, DNA fragments tagged with barcodes were gel-purified through amplification with barcode primer sequences (FIG. 8). The present inventors assumed that the DNA fragments would contain generic flanking sequences at both ends of the fragments for the following reasons. The efficiency of the flanking sequence cleavage of the amplified chip oligonucleotides never reaches 100%. As a consequence, flanking sequences remaining uncut at both ends of chip oligonucleotides cause termination of the DNA assembly process. This termination creates intermediates containing generic flanking sequences at both ends. This pre-termination has been considered a critical drawback in developing chip DNA synthesis technology. However, the present inventors expected that the flanking sequences contained in the fragments could be greatly helpful in tagging the randomly assembled products with the sequence containing degenerate barcode sequences by PCR amplification using primers (connecting the flanking sequences contained in the fragments and the degenerate barcode sequences).

The tagging barcode primer sequences consisted of three parts containing the original primer sequences used for the amplification of DNA chip: (a) generic primer sequences used in designing oligonucleotides, (b) 20 bp degenerate-barcode sequences, and (c) 454 primer sequences. The barcode sequence-attached shotgun assembly fragments were further amplified using the 454 primer sequences to increase the concentration of the barcoded assembly products.

It was found that through 454 sequencing analysis of the shotgun assembly fragments, 3% of the DNA fragments (~400 bp) were error-free (FIG. 9a). An in-house Python computer program was developed to determine error-free sequences for use in the subsequent assembly process (FIGS. 9a and 9b). Briefly, the program scans the flanking sequences containing Type IIS enzyme regions in the sequencing data to align the internal sequences to the target reference sequence. When the internal sequences (<300 bp) match perfectly with the reference sequence, the program determines the optimal set of internal sequences that overlap by 20-50 bp with other fragments, which is then applied to the next round of the assembly process (FIG. 8g).

This analysis using the Python program resulted in error-free shotgun assembled DNA fragments (~300 bp) covering 88% of the 11,376 bp target sequence. For the remaining ~12% DNA sequences, the error containing sequences were analyzed to determine which sequences could be re-amplified using primers. 61 pairs of PCR barcode primers were selected from a pool of random assembly products.

The desired shotgun assembly fragments were selectively amplified from the DNA mixtures using degenerate-barcode primer sequences. Based on the gel data (~400 bp), 77% (47 out of 61) of selective amplification reactions resulted in the desired sequences. The non-amplified target sequences were re-evaluated through the Python program. As a result, alternative oligonucleotide sequences were ordered. The alternative primer sequences could be utilized to obtain 100% sequences, which could be used for target DNA synthesis. The sequences (~10%) were TOPO cloned for Sanger DNA sequencing to evaluate their effectiveness. About 99.98% of the Sanger sequencing-evaluated sequences matched with the target reference sequence.

Amplicons using selected DNA include flanking sequences containing Type IIS restriction enzyme recognition sequences used in the processing procedure of chip oligonucleotides. Accordingly, prior to assembly of the amplified error-free fragments into the target DNA, the barcode sequences of the amplified fragments were cleaved with Type II restriction enzymes (Type IIS restriction enzyme, EarI, BtsI or EcoP15I) (FIG. 7). For the second round of DNA assembly, 3-7 flanking sequence-cleaved fragments (each ~300 bp) were pooled and 11 fragments (each ~1 kb long) were constructed by nested PCR (FIG. 8i). As illustrated in FIG. 7, 5-end and 3-end primer sets of the 11 gene fragments, each of which contained the same base sequence as the target gene fragment, were used for DNA assembly. The chemically synthesized 1 kb DNA fragments were TOPO cloned and submitted for Sanger sequencing to validate their sequences. In summary, 1-3 colonies were chosen from each of the 11 constructs for sequencing, and as a result, nine of the constructs were confirmed to contain at least one desired DNA sequence (16 out of 21 colonies were error-free with an error rate of 0.022% (i.e. 5 errors per 22,903 bp). Final nested PCR assembly was performed using the 11 sequence-validated DNA fragments (FIG. 8j) to construct the penicillin biosynthetic gene cluster, and the products were cloned for sequencing. As a result of the sequencing, the desired penicillin gene cluster was successfully obtained (no error per 11,400 bp).

It is worth to further discuss various points in order to illustrate the creative features of the present disclosure. First, the shotgun synthesis of the present disclosure can provide a solution to the intrinsic challenges associated with low DNA assembly efficiency. DNA assembly processes occur less efficiently due to the increased number of oligonucleotides in a sub-pool (causing a low oligonucleotide concentration) and the presence of partially cleaved flanking sequences in the oligonucleotides. For example, highly heterogeneous by-products of ~100-500 bp corresponding to small-sized DNA fragments were observed continuously during assembly of target gene clusters. In contrast, the shotgun DNA synthesis of the present disclosure enables the use of highly heterogeneous by-products in subsequent DNA assembly processes and therefore has advantages over conventional gene synthesis methods.

Second, a method of identifying and isolating error-free DNA fragments from a number of random shotgun assembly products was successfully developed. Barcoded primer sequences of the synthetic DNA sequence were validated by high-throughput sequencing. The barcode sequences could be utilized in selective PCR amplification of desired DNA molecules from a pool of the DNA molecules. After removal of the amplification primer sequences from the selectively amplified target DNA fragments, the fragments were hierarchically used in the assembly of the target sequence. In addition, it is evident that when the size of the target DNA molecules is sufficient to be sequenced at one time by the next-generation sequencing technology, the products obtained in the first round of the shotgun synthesis can be directly used.

Third, a cost estimate for DNA synthesis using Agilent chip-oligonucleotides and high-throughput sequencing is provided below. The two major costs associated with synthesis of large DNA are the costs of oligonucleotides and sequencing. The synthesis cost of chip oligonucleotides is expected to be $0.00085/nt, which is 100 times cheaper than resin-based oligonucleotides (Kim et al., 2011). In addition, 454 sequencing reads were computationally analyzed for sequencing cost-analysis. As a result, it was confirmed that 3% of the 300 bp DNA fragments produced in the first round of shotgun synthesis were error-free. The sequencing reading was performed using ⅛ lane of Roche-454 sequencing, which costs about $ 1,500. That is, the cost of synthesizing the 10 kb gene cluster was close to $ 3,000 (the cost of synthesizing oligonucleotides=$0.00085/nt*2*228*150 nt=$60; and the cost of various primers=$0.1/nt*200*20 nt=$400; the cost of Sanger sequencing=$3*100 reaction=$300; Roche-454 sequencing cost=$1,500; the cost of various purification kits and enzymes=$800). The cost of DNA synthesis by the synthesis method of the present disclosure is at least five times lower than the current price ($0.5/bp) charged by DNA synthesis companies. The concern that the present inventors have with this approach is the uneven coverage of the DNA assembly fragments. From the repeated assembly experiments, the present inventors found that the coverage of certain regions from the DNA assembly processes was dependent on the DNA sequences. It would be ideal to develop a shotgun assembly process that provides more uniform coverage.

Although the particulars of the present disclosure has been described in detail, it will be obvious to those skilled in the art that such particulars are merely preferred embodiments and are not intended to limit the scope of the present disclosure. Therefore, the true scope of the present disclosure is defined by the appended claims and their equivalents.

What is claimed is:

1. A method of preparing nucleic acid molecules, comprising;
   (a) providing a pool of oligonucleotides, each of the oligonucleotides containing restriction enzyme digestion sequences and generic flanking sequences,
   (b) cleaving the restriction enzyme digestion sequences adjacent to the generic flanking sequences to form a pool of cleaved oligonucleotides such that the pool of the cleaved oligonucleotides consists of a first group of oligonucleotides and a second group of oligonucleotides, wherein each oligonucleotide in the first group contains the generic flanking sequences only at one end, and each oligonucleotide in the second group does not contain the generic flanking sequence at either end,
   (c) assembling the cleaved oligonucleotides using the generic flanking sequences to randomly synthesize nucleic acid fragments,
   (d) tagging the nucleic acid fragments by adding barcode sequences to the generic flanking sequences present at an end of the nucleic acid fragments,
   (e) validating sequences of the tagged nucleic acid fragments, and
   (f) recovering desired nucleic acid fragments from the validated nucleic acid fragments.

2. The method according to claim 1, wherein the nucleic acid fragments randomly synthesized in step (c) comprise nucleic acid fragments having 1,000 bp or more and containing the generic flanking sequences at least one end.

3. The method according to claim 1, further comprising amplifying the oligonucleotides provided in step (a) wherein the oligonucleotides are derived from a DNA microarray.

4. The method according to claim 1, wherein the oligonucleotides provided in step (a) have a size of 20 to 300 bp.

5. The method according to claim 1, further comprising amplifying the nucleic acid fragments provided in step (c).

6. The method according to claim 1, wherein the nucleic acid fragments provided in step (c) have a size of 50 to 3,000 bp.

* * * * *